United States Patent
Sabatini et al.

(10) Patent No.: US 11,499,981 B2
(45) Date of Patent: Nov. 15, 2022

(54) METHODS OF IDENTIFYING MODULATORS OF SAMTOR-GATOR1 INTERACTION AND USE OF SAME TO MODULATE MTORC1

(71) Applicant: Whitehead Institute for Biomedical Research, Cambridge, MA (US)

(72) Inventors: David M. Sabatini, Cambridge, MA (US); Xin Gu, Cambridge, MA (US); Jose M. Orozco, Boston, MA (US)

(73) Assignee: Whitehead Institute for Biomedical Research, Cambridge, MA (US)

( * ) Notice: Subject to any disclaimer, the term of this patent is extended or adjusted under 35 U.S.C. 154(b) by 570 days.

(21) Appl. No.: 16/164,644

(22) Filed: Oct. 18, 2018

(65) Prior Publication Data

US 2019/0234942 A1 Aug. 1, 2019

Related U.S. Application Data

(60) Provisional application No. 62/574,623, filed on Oct. 19, 2017.

(51) Int. Cl.
| | |
|---|---|
| *G01N 33/53* | (2006.01) |
| *G01N 33/68* | (2006.01) |
| *A61K 38/00* | (2006.01) |
| *G01N 33/48* | (2006.01) |
| *C12Q 1/00* | (2006.01) |
| *G01N 33/50* | (2006.01) |
| *C07K 19/00* | (2006.01) |
| *G01N 33/532* | (2006.01) |

(52) U.S. Cl.
CPC ......... *G01N 33/6872* (2013.01); *A61K 38/00* (2013.01); *C07K 19/00* (2013.01); *C12Q 1/00* (2013.01); *G01N 33/48* (2013.01); *G01N 33/50* (2013.01); *G01N 33/5032* (2013.01); *G01N 33/53* (2013.01); *G01N 33/532* (2013.01); *G01N 33/68* (2013.01); *G01N 33/6896* (2013.01); *G01N 2500/02* (2013.01); *G01N 2500/04* (2013.01); *G01N 2500/20* (2013.01); *G01N 2800/2821* (2013.01); *G01N 2800/2835* (2013.01)

(58) Field of Classification Search
None
See application file for complete search history.

(56) References Cited

U.S. PATENT DOCUMENTS

| | | |
|---|---|---|
| 2003/0050274 A1 | 3/2003 | Lee |
| 2004/0249128 A1 | 12/2004 | Thornton et al. |
| 2017/0082633 A1 | 3/2017 | Sabatini et al. |
| 2017/0285043 A1 | 10/2017 | Sabatini et al. |

FOREIGN PATENT DOCUMENTS

WO    WO 2017/117281 A1    7/2017

OTHER PUBLICATIONS

Gu, Xin, et al. "SAMTOR is an S-adenosylmethionine sensor for the mTORC1 pathway." Science 358.6364 (2017): 813-818.
Wolfson, Rachel L., et al. "KICSTOR recruits GATOR1 to the lysosome and is necessary for nutrients to regulate mTORC1." Nature 543.7645 (2017): 438.
Orozco, Jose Miguel, Abstract "Determining the Mechanism of Aspartate Sensing by the MTOR Pathway," National Institutes of Health Grant No. CA210373-02, funded on Sep. 1, 2016, through CA210373-04, funded on Sep. 1, 2018.
Sabatini, David M., Abstract "Regulation of the MTOR Growth Pathway By Nutrients," National Institutes of Health Grant No. CA103866-01, funded on Mar. 23, 2004, through CA103866-05, funded on Mar. 1, 2008.
Sabatini, David M., Abstract "Regulation of the MTOR Pathway By Nutrients," National Institutes of Health Grant No. CA103866-06A1, funded on Jul. 7, 2009, through CA103866-16, funded on Apr. 1, 2019.
Sabatini, David M., Abstract "Translational Control By Rapamycin-Sensitive Signaling," National Institutes of Health Grant No. AI047389-01, funded on Apr. 1, 2000, through AI047389-05, funded on Apr. 1, 2004.
Sabatini, David M., Abstract "Rapamycin-Insensitive Signaling by RICTOR-MTOR," National Institutes of Health Grant No. AI047389-06, funded on Apr. 1, 2005, through AI047389-10, funded on Apr. 1, 2009.
Sabatini, David M., Abstract "Novel Components of the MTORC1 and MTORC2 Pathway," National Institutes of Health Grant No. AI047389-11, funded on May 1, 2010, through AI047389-20, funded on May 1, 2019.
International Search Report in International Application No. PCT/US2018/056547, dated Feb. 19, 2019.

*Primary Examiner* — Michael D Pak
(74) *Attorney, Agent, or Firm* — Morse, Barnes-Brown & Pendleton, P.C.; Lisa M. Warren, Esq.; Erin E. Bryan, Esq.

(57) ABSTRACT

The invention relates to methods of identifying compounds that modulate mTORC1 activity in a cell by modulating the activity of SAMTOR, as well as to the use of such identified compounds in the modulation of mTORC1 and the treatment of diseases and conditions characterized by aberrant mTORC1 activity.

9 Claims, 15 Drawing Sheets

Specification includes a Sequence Listing.

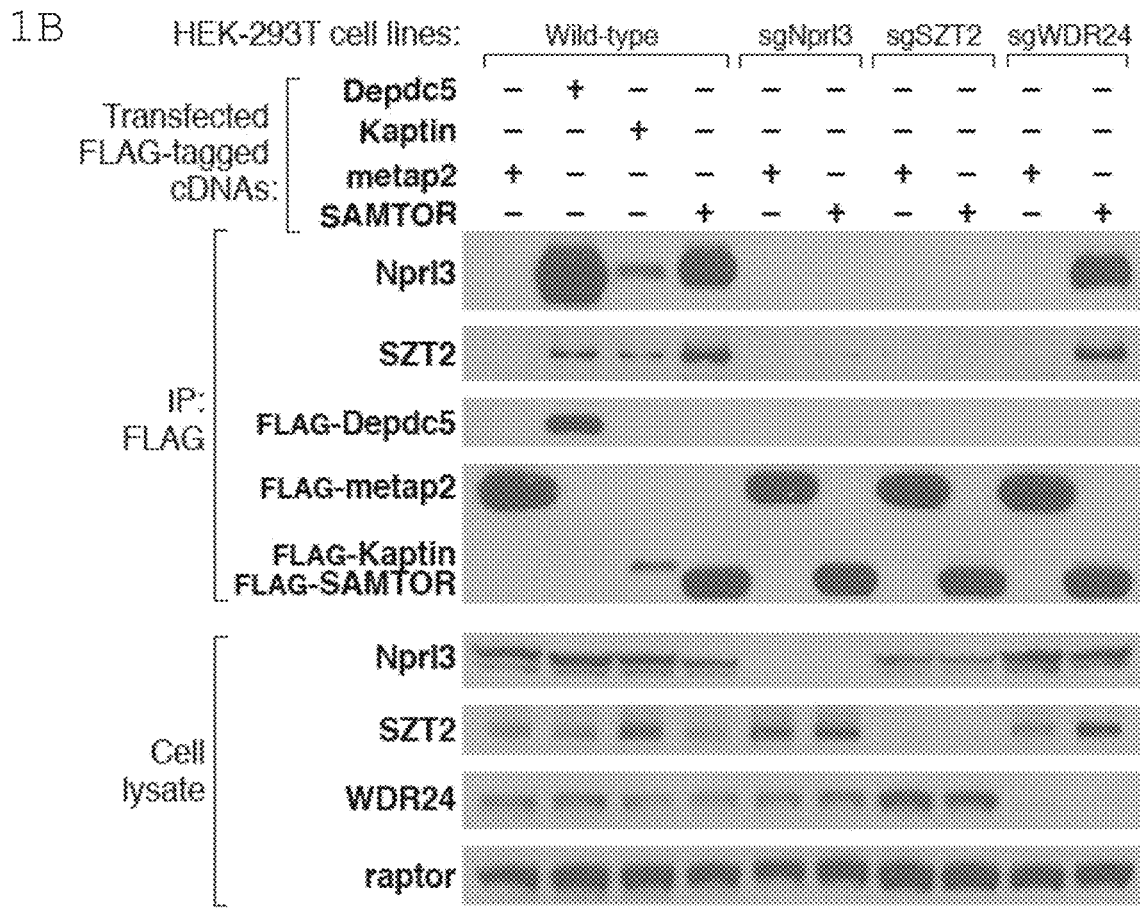
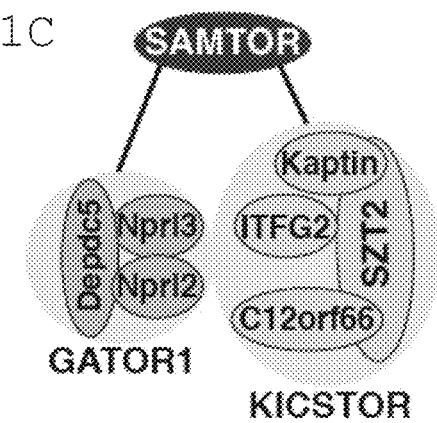
FIGS. 1B-1D

SEQUENCE LISTING

```
<160> NUMBER OF SEQ ID NOS: 50

<210> SEQ ID NO 1
<211> LENGTH: 49
<212> TYPE: DNA
<213> ORGANISM: Artificial
<220> FEATURE:
<223> OTHER INFORMATION: F-dsGFP primer

<400> SEQUENCE: 1
gaattaatac gactcactat agggagaagc tgaccctgaa gttcatctg          49

<210> SEQ ID NO 2
<211> LENGTH: 52
<212> TYPE: DNA
<213> ORGANISM: Artificial
<220> FEATURE:
<223> OTHER INFORMATION: R-dsGFP primer

<400> SEQUENCE: 2
gaattaatac gactcactat agggagatat agacgttgtg gctgttgtag tt       52

<210> SEQ ID NO 3
<211> LENGTH: 49
<212> TYPE: DNA
<213> ORGANISM: Artificial
<220> FEATURE:
<223> OTHER INFORMATION: F-dsdSamtor primer

<400> SEQUENCE: 3
gaattaatac gactcactat agggagatgg aatcctacag agccgaggg          49

<210> SEQ ID NO 4
<211> LENGTH: 51
<212> TYPE: DNA
<213> ORGANISM: Artificial
<220> FEATURE:
<223> OTHER INFORMATION: R-dsdSamtor primer

<400> SEQUENCE: 4
gaattaatac gactcactat agggagacgt acccgtagca gtccaatcct g        51

<210> SEQ ID NO 5
<211> LENGTH: 50
<212> TYPE: DNA
<213> ORGANISM: Artificial
<220> FEATURE:
<223> OTHER INFORMATION: F-dsdSesn primer

<400> SEQUENCE: 5
gaattaatac gactcactat agggagagac tacgactatg gcgaagtgaa         50

<210> SEQ ID NO 6
<211> LENGTH: 52
<212> TYPE: DNA
<213> ORGANISM: Artificial
<220> FEATURE:
```

<223> OTHER INFORMATION: R-dsdSesn primer

<400> SEQUENCE: 6
gaattaatac gactcactat agggagatca agtcatatag cgcattatct cg         52

<210> SEQ ID NO 7
<211> LENGTH: 20
<212> TYPE: DNA
<213> ORGANISM: Artificial
<220> FEATURE:
<223> OTHER INFORMATION: F-alpha-tubulin primer

<400> SEQUENCE: 7
caaccagatg gtcaagtgcg                                              20

<210> SEQ ID NO 8
<211> LENGTH: 20
<212> TYPE: DNA
<213> ORGANISM: Artificial
<220> FEATURE:
<223> OTHER INFORMATION: R-alpha-tubulin primer

<400> SEQUENCE: 8
acgtccttgg gcacaacatc                                              20

<210> SEQ ID NO 9
<211> LENGTH: 20
<212> TYPE: DNA
<213> ORGANISM: Artificial
<220> FEATURE:
<223> OTHER INFORMATION: F-dSamtor primer

<400> SEQUENCE: 9
gaccaacgat gggaaggtgg                                              20

<210> SEQ ID NO 10
<211> LENGTH: 21
<212> TYPE: DNA
<213> ORGANISM: Artificial
<220> FEATURE:
<223> OTHER INFORMATION: R-dSamtor primer

<400> SEQUENCE: 10
gctctgtagg attccaggag t                                            21

<210> SEQ ID NO 11
<211> LENGTH: 21
<212> TYPE: DNA
<213> ORGANISM: Artificial
<220> FEATURE:
<223> OTHER INFORMATION: F-dSesn primer

<400> SEQUENCE: 11
tccgctgcct aacgattaca g                                            21

<210> SEQ ID NO 12
<211> LENGTH: 21
<212> TYPE: DNA
<213> ORGANISM: Artificial
<220> FEATURE:
<223> OTHER INFORMATION: R-dSesn primer

<400> SEQUENCE: 12
ttcaccagat acggacactg a                                            21

```
<210> SEQ ID NO 13
<211> LENGTH: 25
<212> TYPE: DNA
<213> ORGANISM: Artificial
<220> FEATURE:
<223> OTHER INFORMATION: sgSAMTOR_guide1_S

<400> SEQUENCE: 13
caccggaaat actgctcgtg cgcag                                              25

<210> SEQ ID NO 14
<211> LENGTH: 25
<212> TYPE: DNA
<213> ORGANISM: Artificial
<220> FEATURE:
<223> OTHER INFORMATION: sgSAMTOR_guide1_AS

<400> SEQUENCE: 14
aaacctgcgc acgagcagta tttcc                                              25

<210> SEQ ID NO 15
<211> LENGTH: 25
<212> TYPE: DNA
<213> ORGANISM: Artificial
<220> FEATURE:
<223> OTHER INFORMATION: sgSAMTOR_1 (S)

<400> SEQUENCE: 15
caccggaaat actgctcgtg cgcag                                              25

<210> SEQ ID NO 16
<211> LENGTH: 25
<212> TYPE: DNA
<213> ORGANISM: Artificial
<220> FEATURE:
<223> OTHER INFORMATION: sgSAMTOR_1 (AS)

<400> SEQUENCE: 16
aaacctgcgc acgagcagta tttcc                                              25

<210> SEQ ID NO 17
<211> LENGTH: 25
<212> TYPE: DNA
<213> ORGANISM: Artificial
<220> FEATURE:
<223> OTHER INFORMATION: sgSAMTOR_2 (S)

<400> SEQUENCE: 17
caccggatat ggagccaggg gccgg                                              25

<210> SEQ ID NO 18
<211> LENGTH: 25
<212> TYPE: DNA
<213> ORGANISM: Artificial
<220> FEATURE:
<223> OTHER INFORMATION: sgSAMTOR_2 (AS)

<400> SEQUENCE: 18
aaacccggcc cctggctcca tatcc                                              25

<210> SEQ ID NO 19
<211> LENGTH: 25
<212> TYPE: DNA
<213> ORGANISM: Artificial
<220> FEATURE:
<223> OTHER INFORMATION: sgMmSamtor_1 (S)
```

<400> SEQUENCE: 19
caccggcagg agaagctgtc cgggg                          25

<210> SEQ ID NO 20
<211> LENGTH: 25
<212> TYPE: DNA
<213> ORGANISM: Artificial
<220> FEATURE:
<223> OTHER INFORMATION: sgMmSamtor_1 (AS)

<400> SEQUENCE: 20
aaaccgccac taagaccact ccagc                          25

<210> SEQ ID NO 21
<211> LENGTH: 25
<212> TYPE: DNA
<213> ORGANISM: Artificial
<220> FEATURE:
<223> OTHER INFORMATION: sgMmSamtor_2 (S)

<400> SEQUENCE: 21
caccgctccg caagaagtac cgcga                          25

<210> SEQ ID NO 22
<211> LENGTH: 25
<212> TYPE: DNA
<213> ORGANISM: Artificial
<220> FEATURE:
<223> OTHER INFORMATION: sgMmSamtor_2 (AS)

<400> SEQUENCE: 22
aaactcgcgg tacttcttgc ggagc                          25

<210> SEQ ID NO 23
<211> LENGTH: 25
<212> TYPE: DNA
<213> ORGANISM: Artificial
<220> FEATURE:
<223> OTHER INFORMATION: sgMmSamtor_3 (S)

<400> SEQUENCE: 23
caccgatgaa cgctcttcac caccc                          25

<210> SEQ ID NO 24
<211> LENGTH: 25
<212> TYPE: DNA
<213> ORGANISM: Artificial
<220> FEATURE:
<223> OTHER INFORMATION: sgMmSamtor_3 (AS)

<400> SEQUENCE: 24
aaacgggtgg tgaagagcgt tcatc                          25

<210> SEQ ID NO 25
<211> LENGTH: 25
<212> TYPE: DNA
<213> ORGANISM: Artificial
<220> FEATURE:
<223> OTHER INFORMATION: sgMAT2A_1 (S)

<400> SEQUENCE: 25
caccgttaaa ggaggtctgt gccgg                          25

<210> SEQ ID NO 26
<211> LENGTH: 25

```
<212> TYPE: DNA
<213> ORGANISM: Artificial
<220> FEATURE:
<223> OTHER INFORMATION: sgMAT2A_1 (AS)

<400> SEQUENCE: 26
aaacccggca cagacctcct ttaac                                    25

<210> SEQ ID NO 27
<211> LENGTH: 29
<212> TYPE: PRT
<213> ORGANISM: Homo sapiens

<400> SEQUENCE: 27

Ile Arg Leu Leu Asp Val Gly Ser Cys Phe Asn Pro Phe Leu Lys Phe
1               5                   10                  15

Glu Glu Phe Leu Thr Val Gly Ile Asp Ile Val Pro Ala
            20                  25

<210> SEQ ID NO 28
<211> LENGTH: 29
<212> TYPE: PRT
<213> ORGANISM: Pan troglodytes

<400> SEQUENCE: 28

Ile Arg Leu Leu Asp Val Gly Ser Cys Phe Asn Pro Phe Leu Lys Phe
1               5                   10                  15

Glu Glu Phe Leu Thr Val Gly Ile Asp Ile Val Pro Ala
            20                  25

<210> SEQ ID NO 29
<211> LENGTH: 29
<212> TYPE: PRT
<213> ORGANISM: Macaca mulatta

<400> SEQUENCE: 29

Ile Arg Leu Leu Asp Val Gly Ser Cys Phe Asn Pro Phe Leu Lys Phe
1               5                   10                  15

Glu Glu Phe Leu Thr Val Gly Ile Asp Ile Val Pro Ala
            20                  25

<210> SEQ ID NO 30
<211> LENGTH: 29
<212> TYPE: PRT
<213> ORGANISM: Callithrix jacchus

<400> SEQUENCE: 30

Ile Arg Leu Leu Asp Val Gly Ser Cys Phe Asn Pro Phe Leu Lys Phe
1               5                   10                  15

Glu Glu Phe Leu Thr Val Gly Ile Asp Ile Val Pro Ala
            20                  25

<210> SEQ ID NO 31
<211> LENGTH: 29
<212> TYPE: PRT
<213> ORGANISM: Mus musculus

<400> SEQUENCE: 31

Ile Arg Leu Leu Asp Val Gly Ser Cys Phe Asn Pro Phe Leu Lys Phe
1               5                   10                  15

Glu Glu Phe Leu Thr Val Gly Ile Asp Ile Val Pro Ala
            20                  25
```

<210> SEQ ID NO 32
<211> LENGTH: 29
<212> TYPE: PRT
<213> ORGANISM: Gallus gallus

<400> SEQUENCE: 32

Ile Arg Leu Leu Asp Val Gly Ser Cys Phe Asn Pro Phe Leu Lys Phe
1               5                   10                  15

Glu Glu Phe Leu Thr Val Gly Ile Asp Ile Val Pro Ala
            20                  25

<210> SEQ ID NO 33
<211> LENGTH: 29
<212> TYPE: PRT
<213> ORGANISM: Xenopus tropicalis

<400> SEQUENCE: 33

Ile Arg Leu Leu Asp Val Gly Ser Cys Tyr Asn Pro Phe Leu Lys Tyr
1               5                   10                  15

Glu Asp Phe Leu Ala Val Gly Ile Asp Ile Val Pro Ala
            20                  25

<210> SEQ ID NO 34
<211> LENGTH: 29
<212> TYPE: PRT
<213> ORGANISM: Danio rerio

<400> SEQUENCE: 34

Ile Arg Leu Leu Asp Val Gly Ser Cys Phe Asn Pro Phe Leu Lys Phe
1               5                   10                  15

Asp Glu Phe Leu Thr Val Gly Ile Asp Ile Val Pro Ala
            20                  25

<210> SEQ ID NO 35
<211> LENGTH: 29
<212> TYPE: PRT
<213> ORGANISM: Drosophila melanogaster

<400> SEQUENCE: 35

Leu His Val Leu Asp Val Gly Ser Cys Phe Asn Pro Phe Ser Ser Ala
1               5                   10                  15

Pro His Leu Glu Val Thr Ala Leu Asp Leu Cys Pro Ala
            20                  25

<210> SEQ ID NO 36
<211> LENGTH: 29
<212> TYPE: PRT
<213> ORGANISM: Hydra vulgaris

<400> SEQUENCE: 36

Ile Val Leu Leu Asp Val Gly Ser Cys Phe Asn Gly Phe Lys Glu Phe
1               5                   10                  15

Asn Glu Phe Leu Val Phe Pro Ile Asp Ile Ala Pro Ala
            20                  25

<210> SEQ ID NO 37
<211> LENGTH: 405
<212> TYPE: PRT
<213> ORGANISM: Homo sapiens -continued

<400> SEQUENCE: 37

Met Glu Pro Gly Ala Gly Gly Arg Asn Thr Ala Arg Ala Gln Arg Ala
1               5                   10                  15

Gly Ser Pro Asn Thr Pro Pro Arg Glu Gln Glu Arg Lys Leu Glu
            20                  25                  30

Gln Glu Lys Leu Ser Gly Val Val Lys Ser Val His Arg Arg Leu Arg
        35                  40                  45

Lys Lys Tyr Arg Glu Val Gly Asp Phe Asp Lys Ile Trp Arg Glu His
    50                  55                  60

Cys Glu Asp Glu Glu Thr Leu Cys Glu Tyr Ala Val Ala Met Lys Asn
65                  70                  75                  80

Leu Ala Asp Asn His Trp Ala Lys Thr Cys Glu Gly Glu Gly Arg Ile
                85                  90                  95

Glu Trp Cys Cys Ser Val Cys Arg Glu Tyr Phe Gln Asn Gly Gly Lys
            100                 105                 110

Arg Lys Ala Leu Glu Lys Asp Glu Lys Arg Ala Val Leu Ala Thr Lys
        115                 120                 125

Thr Thr Pro Ala Leu Asn Met His Glu Ser Ser Gln Leu Glu Gly His
    130                 135                 140

Leu Thr Asn Leu Ser Phe Thr Asn Pro Glu Phe Ile Thr Glu Leu Leu
145                 150                 155                 160

Gln Ala Ser Gly Lys Ile Arg Leu Leu Asp Val Gly Ser Cys Phe Asn
                165                 170                 175

Pro Phe Leu Lys Phe Glu Glu Phe Leu Thr Val Gly Ile Asp Ile Val
            180                 185                 190

Pro Ala Val Glu Ser Val Tyr Lys Cys Asp Phe Leu Asn Leu Gln Leu
        195                 200                 205

Gln Gln Pro Leu Gln Leu Ala Gln Asp Ala Ile Asp Ala Phe Leu Lys
    210                 215                 220

Gln Leu Lys Asn Pro Ile Asp Ser Leu Pro Gly Glu Leu Phe His Val
225                 230                 235                 240

Val Val Phe Ser Leu Leu Leu Ser Tyr Phe Pro Ser Pro Tyr Gln Arg
                245                 250                 255

Trp Ile Cys Cys Lys Lys Ala His Glu Leu Leu Val Leu Asn Gly Leu
            260                 265                 270

Leu Leu Ile Ile Thr Pro Asp Ser Ser His Gln Asn Arg His Ala Met
        275                 280                 285

Met Met Lys Ser Trp Lys Ile Ala Ile Glu Ser Leu Gly Phe Lys Arg
    290                 295                 300

Phe Lys Tyr Ser Lys Phe Ser His Met His Leu Met Ala Phe Arg Lys
305                 310                 315                 320

Ile Ser Leu Lys Thr Thr Ser Asp Leu Val Ser Arg Asn Tyr Pro Gly
                325                 330                 335

Met Leu Tyr Ile Pro Gln Asp Phe Asn Ser Ile Glu Asp Glu Glu Tyr
            340                 345                 350

Ser Asn Pro Ser Cys Tyr Val Arg Ser Asp Ile Glu Asp Glu Gln Leu
        355                 360                 365

Ala Tyr Gly Phe Thr Glu Leu Pro Asp Ala Pro Tyr Asp Ser Asp Ser
    370                 375                 380

Gly Glu Ser Gln Ala Ser Ser Ile Pro Phe Tyr Glu Leu Glu Asp Pro
385                 390                 395                 400

Ile Leu Leu Leu Ser
                405

<210> SEQ ID NO 38
<211> LENGTH: 405
<212> TYPE: PRT
<213> ORGANISM: Pan troglodytes

<400> SEQUENCE: 38

Met Glu Pro Gly Ala Gly Gly Arg Asn Thr Ala Arg Gly Gln Arg Ala
1               5                   10                  15

Gly Ser Pro Asn Thr Pro Pro Arg Glu Gln Glu Arg Lys Leu Glu
            20                  25                  30

Gln Glu Lys Leu Ser Gly Val Val Lys Ser Val His Arg Arg Leu Arg
            35                  40                  45

Lys Lys Tyr Arg Glu Val Gly Asp Phe Asp Lys Ile Trp Arg Glu His
50                  55                  60

Cys Glu Asp Glu Glu Thr Leu Cys Glu Tyr Ala Val Ala Met Lys Asn
65                  70                  75                  80

Leu Ala Asp Asn His Trp Ala Lys Thr Cys Glu Gly Glu Gly Arg Ile
                85                  90                  95

Glu Trp Cys Cys Ser Val Cys Arg Glu Tyr Phe Gln Asn Gly Gly Lys
            100                 105                 110

Arg Lys Ala Leu Glu Lys Asp Glu Lys Arg Ala Val Leu Ala Thr Lys
            115                 120                 125

Thr Thr Pro Ala Leu Asn Met His Glu Ser Ser Gln Leu Glu Gly His
130                 135                 140

Leu Thr Asn Leu Ser Phe Thr Asn Pro Glu Phe Ile Thr Glu Leu Leu
145                 150                 155                 160

Gln Ala Ser Gly Lys Ile Arg Leu Leu Asp Val Gly Ser Cys Phe Asn
                165                 170                 175

Pro Phe Leu Lys Phe Glu Glu Phe Leu Thr Val Gly Ile Asp Ile Val
            180                 185                 190

Pro Ala Val Glu Ser Val Tyr Lys Cys Asp Phe Leu Asn Leu Gln Leu
            195                 200                 205

Gln Gln Pro Leu Gln Leu Ala Gln Asp Ala Ile Asp Ala Phe Leu Lys
210                 215                 220

Gln Leu Lys Asn Pro Ile Asp Ser Leu Pro Gly Glu Leu Phe His Val
225                 230                 235                 240

Val Val Phe Ser Leu Leu Ser Tyr Phe Pro Ser Pro Tyr Gln Arg
                245                 250                 255

Trp Ile Cys Cys Lys Lys Ala His Glu Leu Leu Val Leu Asn Gly Leu
            260                 265                 270

Leu Leu Ile Ile Thr Pro Asp Ser Ser His Gln Asn Arg His Ala Met
            275                 280                 285

Met Met Lys Ser Trp Lys Ile Ala Ile Glu Ser Leu Gly Phe Lys Arg
290                 295                 300

Phe Lys Tyr Ser Lys Phe Ser His Met His Leu Met Ala Phe Arg Lys
305                 310                 315                 320

Ile Ser Leu Lys Thr Thr Ser Asp Leu Val Ser Arg Asn Tyr Pro Gly
                325                 330                 335

```
Met Leu Tyr Ile Pro Gln Asp Phe Asn Ser Ile Glu Asp Glu Tyr
            340                 345                 350

Ser Asn Pro Ser Cys Tyr Val Arg Ser Asp Ile Glu Asp Glu Gln Leu
            355                 360                 365

Ala Tyr Gly Phe Thr Glu Leu Pro Asp Ala Pro Tyr Asp Ser Asp Ser
            370                 375                 380

Gly Glu Ser Gln Ala Ser Ser Ile Pro Phe Tyr Glu Leu Glu Asp Pro
385                 390                 395                 400

Ile Leu Leu Leu Ser
                405

<210> SEQ ID NO 39
<211> LENGTH: 405
<212> TYPE: PRT
<213> ORGANISM: Macaca mulatta

<400> SEQUENCE: 39

Met Glu Pro Gly Ala Gly Gly Arg Ser Thr Ala Arg Gly Gln Arg Ala
1               5                   10                  15

Gly Pro Pro Asn Thr Pro Pro Arg Glu Gln Glu Arg Lys Leu Glu
            20                  25                  30

Gln Glu Lys Leu Ser Gly Val Val Lys Ser Val His Arg Arg Leu Arg
            35                  40                  45

Lys Lys Tyr Arg Glu Val Gly Asp Phe Asp Lys Ile Trp Arg Glu His
        50                  55                  60

Cys Glu Asp Glu Glu Thr Leu Cys Glu Tyr Ala Val Ala Met Lys Asn
65                  70                  75                  80

Leu Ala Asp Asn His Trp Ala Lys Thr Cys Gly Glu Gly Arg Ile
                85                  90                  95

Glu Trp Cys Cys Ser Val Cys Arg Glu Tyr Phe Gln Asn Gly Gly Lys
            100                 105                 110

Arg Lys Ala Leu Glu Lys Asp Glu Lys Arg Ala Val Leu Ala Thr Lys
            115                 120                 125

Thr Thr Pro Ala Leu Asn Met His Glu Ser Ser Lys Leu Glu Gly His
            130                 135                 140

Leu Thr Asn Leu Ser Phe Thr Asn Pro Glu Phe Ile Thr Glu Leu Leu
145                 150                 155                 160

Gln Ala Ser Gly Lys Ile Arg Leu Leu Asp Val Gly Ser Cys Phe Asn
                165                 170                 175

Pro Phe Leu Lys Phe Glu Glu Phe Leu Thr Val Gly Ile Asp Ile Val
            180                 185                 190

Pro Ala Val Glu Ser Val Tyr Lys Cys Asp Phe Leu Asn Leu Gln Leu
            195                 200                 205

Gln Gln Pro Leu Gln Leu Ala Gln Asp Ala Ile Asp Ala Phe Leu Lys
            210                 215                 220

Gln Leu Lys Asn Pro Ile Asp Ser Leu Pro Gly Glu Leu Phe His Val
225                 230                 235                 240

Val Val Phe Ser Leu Leu Leu Ser Tyr Phe Pro Ser Pro Tyr Gln Arg
                245                 250                 255

Trp Ile Cys Cys Lys Lys Ala His Glu Leu Leu Val Leu Asn Gly Leu
            260                 265                 270

Leu Leu Ile Ile Thr Pro Asp Ser Ser His Gln Asn Arg His Ala Met
            275                 280                 285
```

Met Met Lys Ser Trp Lys Ile Ala Ile Glu Ser Leu Gly Phe Lys Arg
            290                 295                 300

Phe Lys Tyr Ser Lys Phe Ser His Met His Leu Met Ala Phe Arg Lys
305                 310                 315                 320

Ile Ser Leu Lys Thr Thr Ser Asp Leu Val Ser Arg Asn Tyr Pro Gly
            325                 330                 335

Met Leu Tyr Ile Pro Gln Asp Phe Asn Ser Ile Glu Asp Glu Tyr
            340                 345                 350

Ser Asn Pro Ser Cys Tyr Val Arg Ser Asp Ile Glu Asp Glu Gln Leu
            355                 360                 365

Ala Tyr Gly Phe Thr Glu Leu Pro Asp Ala Pro Tyr Asp Ser Asp Ser
        370                 375                 380

Gly Glu Ser Gln Ala Ser Ser Ile Pro Phe Tyr Glu Leu Glu Asp Pro
385                 390                 395                 400

Ile Leu Leu Leu Ser
            405

<210> SEQ ID NO 40
<211> LENGTH: 405
<212> TYPE: PRT
<213> ORGANISM: Callithrix jacchus

<400> SEQUENCE: 40

Met Glu Pro Gly Ala Gly Gly Arg Ser Thr Ala Arg Gly Gln Lys Ala
1               5                   10                  15

Gly His Pro Asn Thr Pro Pro Arg Glu Gln Glu Arg Lys Leu Glu
            20                  25                  30

Gln Glu Lys Leu Ser Gly Val Val Lys Ser Val His Arg Arg Leu Arg
            35                  40                  45

Lys Lys Tyr Arg Glu Val Gly Asp Phe Asp Lys Ile Trp Arg Glu His
        50                  55                  60

Cys Glu Asp Glu Glu Thr Leu Cys Glu Tyr Ala Val Ala Met Lys Asn
65                  70                  75                  80

Leu Ala Asp Asn His Trp Ala Lys Thr Cys Glu Gly Glu Gly Arg Ile
                85                  90                  95

Glu Trp Cys Cys Ser Val Cys Arg Glu Tyr Phe Gln Asn Gly Gly Lys
            100                 105                 110

Arg Lys Ala Leu Glu Lys Asp Glu Lys Arg Ala Val Leu Ala Thr Lys
        115                 120                 125

Thr Thr Pro Ala Leu Asn Met His Glu Ser Ser Lys Leu Glu Gly His
130                 135                 140

Leu Thr Asn Leu Ser Phe Thr Asn Pro Glu Phe Ile Thr Glu Leu Leu
145                 150                 155                 160

Gln Ala Ser Gly Lys Ile Arg Leu Leu Asp Val Gly Ser Cys Phe Asn
                165                 170                 175

Pro Phe Leu Lys Phe Glu Glu Phe Leu Thr Val Gly Ile Asp Ile Val
            180                 185                 190

Pro Ala Val Glu Ser Val Tyr Lys Cys Asp Phe Leu Asn Leu Gln Leu
        195                 200                 205

Gln Gln Pro Leu Gln Leu Ala Gln Asp Ala Ile Asp Ala Phe Leu Lys
210                 215                 220

Gln Leu Lys Asn Pro Ile Asp Ser Leu Pro Gly Glu Leu Phe His Val
225                 230                 235                 240

Val Val Phe Ser Leu Leu Ser Tyr Phe Pro Ser Pro Tyr Gln Arg
            245                 250                 255

Trp Ile Cys Cys Lys Lys Ala His Glu Leu Leu Val Leu Asn Gly Leu
            260                 265                 270

Leu Leu Ile Ile Thr Pro Asp Ser Ser His Gln Asn Arg His Ala Met
        275                 280                 285

Met Met Lys Ser Trp Lys Ile Ala Ile Glu Ser Leu Gly Phe Lys Arg
    290                 295                 300

Phe Lys Tyr Ser Lys Phe Ser His Met His Leu Met Ala Phe Arg Lys
305                 310                 315                 320

Ile Ser Leu Lys Thr Thr Ser Asp Leu Val Ser Arg Asn Tyr Pro Gly
                325                 330                 335

Met Leu Tyr Ile Pro Gln Asp Phe Asn Ser Ile Glu Asp Glu Tyr
            340                 345                 350

Ser Asn Pro Ser Cys Tyr Val Arg Ser Asp Ile Glu Asp Gln Leu
            355                 360                 365

Ala Tyr Gly Phe Thr Glu Leu Pro Asp Ala Pro Tyr Asp Ser Asp Ser
    370                 375                 380

Gly Glu Ser Gln Ala Ser Ser Ile Pro Phe Tyr Glu Leu Glu Asp Pro
385                 390                 395                 400

Ile Leu Leu Leu Ser
            405

<210> SEQ ID NO 41
<211> LENGTH: 403
<212> TYPE: PRT
<213> ORGANISM: Mus musculus

<400> SEQUENCE: 41

Met Glu Pro Gly Pro Gly Gly Arg Gly Ala Ala Arg Gly Gln Arg Pro
1               5                   10                  15

Pro Asn Ala Ala Gln Pro Arg Glu Gln Glu Arg Lys Leu Glu Gln Glu
            20                  25                  30

Lys Leu Ser Gly Val Val Lys Ser Val His Arg Arg Leu Arg Lys Lys
        35                  40                  45

Tyr Arg Glu Val Gly Asp Phe Asp Lys Ile Trp Arg Glu His Cys Glu
    50                  55                  60

Asp Ala Glu Thr Leu Cys Glu Tyr Ala Val Ala Met Lys Asn Leu Ala
65                  70                  75                  80

Asp Asn His Trp Ala Lys Thr Cys Glu Gly Glu Gly Arg Ile Glu Trp
                85                  90                  95

Cys Cys Ser Val Cys Arg Glu Tyr Phe Gln Asn Gly Gly Lys Arg Lys
            100                 105                 110

Ala Leu Glu Lys Asp Glu Lys Arg Ala Val Leu Ala Thr Lys Thr Thr
        115                 120                 125

Pro Ala Leu Asn Val His Glu Ser Ser Lys Leu Glu Gly Pro Leu Thr
    130                 135                 140

Asn Leu Ser Phe Thr Ser Pro Asp Phe Ile Thr Glu Leu Leu Gln Ala
145                 150                 155                 160

Ser Gly Lys Ile Arg Leu Leu Asp Val Gly Ser Cys Phe Asn Pro Phe
                165                 170                 175

Leu Lys Phe Glu Glu Phe Leu Thr Val Gly Ile Asp Ile Val Pro Ala
            180                 185                 190

-continued

```
Val Glu Ser Val Tyr Lys Cys Asp Phe Leu Asn Leu Gln Leu Gln Gln
            195                 200                 205

Pro Leu Gln Leu Ala Gln Asp Ala Ile Asp Ala Phe Leu Lys Gln Leu
    210                 215                 220

Arg Asn Pro Ile Asp Ala Leu Pro Gly Glu Leu Phe His Val Val
225                 230                 235                 240

Phe Ser Leu Leu Leu Ser Tyr Phe Pro Ser Pro Tyr Gln Arg Trp Ile
                245                 250                 255

Cys Cys Lys Lys Ala His Glu Leu Leu Val Leu Asn Gly Leu Leu Leu
                260                 265                 270

Ile Ile Thr Pro Asp Ser Ser His Gln Asn Arg His Ala Met Met Met
                275                 280                 285

Lys Ser Trp Lys Ile Ala Ile Glu Ser Leu Gly Phe Lys Arg Phe Lys
            290                 295                 300

Tyr Ser Lys Phe Ser His Met His Leu Met Ala Phe Arg Lys Thr Ser
305                 310                 315                 320

Leu Lys Thr Thr Ser Asp Leu Val Ser Arg Asn Tyr Pro Gly Met Leu
                325                 330                 335

Tyr Ile Pro Gln Asp Phe Asn Ser Val Glu Glu Glu Tyr Ser Asn
            340                 345                 350

Thr Ser Cys Tyr Val Arg Ser Asp Leu Glu Asp Glu Gln Leu Ala Tyr
                355                 360                 365

Gly Phe Thr Glu Leu Pro Glu Ala Pro Tyr Asp Ser Asp Ser Gly Glu
            370                 375                 380

Ser Gln Ala Ser Ser Ile Pro Phe Tyr Glu Leu Glu Asp Pro Ile Leu
385                 390                 395                 400

Leu Leu Ser

<210> SEQ ID NO 42
<211> LENGTH: 408
<212> TYPE: PRT
<213> ORGANISM: Gallus gallus

<400> SEQUENCE: 42

Met Glu Ala Ala Pro Arg Ser Arg Pro Arg Pro Gly Gly Ala Ala Ala
1               5                   10                  15

Ser Pro Pro Pro Pro Pro Pro Pro Pro Glu Gln Glu Arg Lys
            20                  25                  30

Leu Glu Gln Glu Lys Leu Ser Gly Val Val Lys Ser Val His Arg Arg
            35                  40                  45

Leu Arg Lys Lys Tyr Arg Glu Val Gly Asp Phe Asp Lys Ile Trp Arg
    50                  55                  60

Glu His Cys Glu Asp Glu Thr Leu Cys Tyr Ala Val Ala Met
65                  70                  75                  80

Lys Asn Leu Ala Asp Asn His Trp Ala Lys Thr Cys Glu Gly Glu Gly
                85                  90                  95

Arg Ile Glu Trp Cys Cys Ser Val Cys Arg Glu Tyr Phe Gln Asn Gly
            100                 105                 110

Gly Lys Arg Lys Ala Leu Glu Lys Asp Glu Lys Arg Ala Leu Leu Ala
            115                 120                 125

Ser Lys Ser Thr Pro Ala Leu Asn Ala Ser Gln Pro Pro Lys Ile Glu
130                 135                 140

Asp Pro Leu Pro Asn Phe Gly Leu Thr Asn His Glu Ala Ile Thr Glu
145                 150                 155                 160
```

```
Glu Leu Leu His Ser Leu Gly Lys Ile Arg Leu Leu Asp Val Gly Ser
                165                 170                 175

Cys Phe Asn Pro Phe Leu Lys Phe Glu Glu Phe Leu Thr Val Gly Ile
            180                 185                 190

Asp Ile Val Pro Ala Val Glu Ser Val Tyr Lys Cys Asp Phe Leu Asn
        195                 200                 205

Leu Gln Ile Gln Gln Pro Leu Gln Leu Ala Gln Asp Ala Ile Asp Ala
    210                 215                 220

Phe Leu Lys Gln Leu Lys Asn Pro Ile Asp Ser Leu Pro Gly Glu Leu
225                 230                 235                 240

Phe His Val Val Val Phe Ser Leu Leu Leu Ser Tyr Phe Pro Ser Pro
                245                 250                 255

Tyr Gln Arg Trp Ile Cys Cys Lys Lys Ala His Glu Leu Leu Val Leu
            260                 265                 270

Asn Gly Leu Leu Leu Val Ile Thr Pro Asp Ser Ser His Gln Asn Arg
        275                 280                 285

Arg Ala Met Met Met Lys Ser Trp Lys Ile Ala Ile Glu Ser Leu Gly
    290                 295                 300

Phe Lys Arg Phe Lys Tyr Ser Lys Phe Ser His Met His Leu Met Ala
305                 310                 315                 320

Phe Arg Lys Thr Ser Leu Gln Thr Thr Ser Asp Leu Val Ser Arg Asn
                325                 330                 335

Tyr Pro Gly Met Leu Tyr Ile Pro Gln Asp Phe Asn Ser Ile Glu Asp
            340                 345                 350

Glu Glu Tyr Ser Asn Thr Ser Cys Tyr Ile Arg Ser Asp Met Glu Asp
        355                 360                 365

Glu Gln Leu Ala Tyr Gly Phe Met Glu Leu Pro Asp Ala Pro Tyr Asp
    370                 375                 380

Ser Asp Ser Gly Glu Ser Gln Ser Ser Ile Pro Phe Tyr Glu Leu
385                 390                 395                 400

Glu Asp Pro Val Leu Leu Leu Ser
                405

<210> SEQ ID NO 43
<211> LENGTH: 410
<212> TYPE: PRT
<213> ORGANISM: Xenopus tropicalis

<400> SEQUENCE: 43

Met Glu Pro Val Leu Gln Ala Arg Gly Lys Arg Glu Asn Val Leu Gly
1               5                   10                  15

Asn Ala Arg Glu Glu Arg Cys Val Pro Gly Phe Pro Ser Ala Cys Glu
            20                  25                  30

Gln Lys Leu Glu Gln Glu Lys Leu Ser Gly Val Val Lys Arg Val His
        35                  40                  45

Arg Asp Leu Arg Lys Lys Tyr Arg Glu Ala Gly Asp Phe Glu Lys Ile
    50                  55                  60

Trp Leu Glu His Cys Lys Asp Lys Gly Arg Leu Cys Glu Tyr Ala Val
65                  70                  75                  80

Ala Met Lys Ala Leu Ala Asp Asn His Trp Ala Lys Lys Cys Glu Gly
                85                  90                  95

Glu Gly Arg Ile Glu Trp Cys Leu Gly Val Cys Gln Glu Tyr Phe Phe
            100                 105                 110
```

Asn Gly Gly Lys Lys Ala Ile Glu Lys Asp Ala Arg Arg Ala Thr
            115                 120                 125

Leu Ile Cys Lys Arg Tyr Val Thr Ser Pro Ile Asn Asn Thr Glu Gln
130                 135                 140

Thr Asn His Glu Gly Phe Pro Thr Leu Glu Asn Ser Lys Gln Asn Asp
145                 150                 155                 160

Phe Val Leu Lys Leu Lys Tyr Met Thr Gly Lys Ile Arg Leu Leu Asp
                165                 170                 175

Val Gly Ser Cys Tyr Asn Pro Phe Leu Lys Tyr Glu Asp Phe Leu Ala
            180                 185                 190

Val Gly Ile Asp Ile Val Pro Ala Val Glu Thr Val Cys Lys Cys Asp
        195                 200                 205

Phe Leu Asn Leu Gln Ile Gln Arg Pro Leu Gln Phe Ala Pro Asp Ala
210                 215                 220

Ile Asp Ala Phe Leu Lys Gln Leu Glu Ser Pro Ile Asp Tyr Leu Pro
225                 230                 235                 240

Ala Glu Leu Phe His Val Val Phe Ser Leu Leu Ser Tyr Phe
                245                 250                 255

Pro Ser Pro Tyr Gln Arg Trp Ile Cys Cys Lys Lys Ala His Glu Leu
            260                 265                 270

Leu Thr Leu Asn Gly Leu Leu Leu Ile Ile Thr Pro Asp Ser Ser His
        275                 280                 285

Gln Asn Arg His Ala Val Met Met Lys Ser Trp Lys Ile Ala Ile Glu
290                 295                 300

Ser Leu Gly Phe Arg Arg Met Thr Tyr Ser Lys Phe Ser His Met His
305                 310                 315                 320

Leu Met Ala Phe Arg Lys Thr Ser Leu Lys Thr Thr Ser Asp Leu Ile
                325                 330                 335

Thr Met Asn Tyr Pro Asp Met Leu Tyr Ile Pro Gln Asp Phe Asn Tyr
            340                 345                 350

Asp Gly Glu Glu Asp Tyr Phe Ser Pro Cys Cys Ala Arg Ser Glu Leu
        355                 360                 365

Glu Asp Glu Gln Leu Ala Cys Gly Phe Thr Glu Leu Pro Asp Thr Pro
370                 375                 380

Tyr Asp Ser Asp Ser Gly Glu Ser Gln Asn Ser Thr Met Pro Phe Tyr
385                 390                 395                 400

Glu Phe Glu Asp Pro Ile Leu Leu Thr
                405                 410

<210> SEQ ID NO 44
<211> LENGTH: 393
<212> TYPE: PRT
<213> ORGANISM: Danio rerio

<400> SEQUENCE: 44

Met Asp Leu Arg Ser Ser Ala Glu Thr Asp Pro Asp Leu Ser Glu Asn
1               5                   10                  15

His Pro Gly Ser Val Pro Ala Glu Leu Gln Ser Arg Lys Gln Glu Gln
            20                  25                  30

Glu Lys Leu Ser Gly Val Val Lys Ser Val His Arg Lys Leu Arg Arg
        35                  40                  45

Lys Tyr Ile Glu Val Gly Asp Phe Asp Lys Ile Trp Arg Glu His Cys
    50                  55                  60

```
Glu Asp Glu Gln Thr Leu Ser Glu Tyr Ala Met Ala Met Lys Asn Leu
 65                  70                  75                  80

Ala Asp Asn His Trp Ala Asn Lys Cys Glu Gly Gly Arg Ile Glu
                 85                  90                  95

Trp Cys Arg Ser Val Cys Gln Tyr Phe Gln Asp Gly Gly Met Arg
            100                 105                 110

Arg Val Leu Glu Lys Asp Glu Lys Ser Ala Arg His Ala Thr Ala Gly
            115                 120                 125

Asn Ala Asn Thr Asp Thr Asn Ala Pro Pro Gln Leu Ser Ser Ile Ser
            130                 135                 140

Thr Ser Ser Thr Phe Gln Leu Gly Arg Ile Arg Leu Leu Asp Val Gly
145                 150                 155                 160

Ser Cys Phe Asn Pro Phe Leu Lys Phe Asp Glu Phe Leu Thr Val Gly
                165                 170                 175

Ile Asp Ile Val Pro Ala Val Glu Ser Val Tyr Lys Cys Asp Phe Leu
            180                 185                 190

Asn Leu Gln Leu Gln Gln Pro Leu Gln Leu Ala Ser Asp Ala Leu Asp
            195                 200                 205

Ala Phe Leu Arg Gln Leu Arg Gly Pro Ile Asp Ala Leu Pro Ala Glu
210                 215                 220

Leu Phe His Val Val Phe Ser Leu Leu Leu Ser Tyr Phe Pro Ser
225                 230                 235                 240

Pro Tyr Gln Arg Trp Leu Cys Cys Lys Lys Ala His Glu Leu Leu Thr
                245                 250                 255

Leu Asn Gly Leu Leu Leu Ile Ile Thr Pro Asp Ser Ser His Gln Gly
            260                 265                 270

Arg His Ala Leu Met Met Arg Ser Trp Arg Val Ala Val Glu Ser Leu
            275                 280                 285

Gly Phe Lys Arg Tyr Lys Tyr Val Lys Phe Ser His Met His Leu Ile
            290                 295                 300

Ala Phe Arg Lys Val Ser Pro Thr Thr Ser Ser Asp Leu Val Ser Arg
305                 310                 315                 320

Asn Tyr Pro Glu Met Leu Tyr Ile Pro Gln Asp Phe Asn Thr Phe Asp
                325                 330                 335

Glu Asp Gly Phe Ala Asp Cys Tyr Glu Pro Pro Arg Ser Asp Phe Glu
            340                 345                 350

Asp Asp Gln Met Ala Cys Ser Phe Ala Glu Leu Pro Glu Thr Pro Tyr
            355                 360                 365

Asp Ser Asp Ser Ser Glu Ser Gln Ser Ser Ala Pro Phe Tyr Glu
            370                 375                 380

Leu Glu Asp Pro Ile Leu Leu Gln Ser
385                 390

<210> SEQ ID NO 45
<211> LENGTH: 302
<212> TYPE: PRT
<213> ORGANISM: Drosophila melanogaster

<400> SEQUENCE: 45

Met Ala Thr Glu Glu His Gln Arg Leu Ala Ser Ile Val Lys Ser Cys
 1               5                  10                  15

His Glu Ser Leu Arg Gln Leu Thr Lys Glu Tyr Gly Ala Thr Ala Ala
             20                  25                  30
```

Trp Gln Glu His Thr Ser Pro Arg Asn Ala Lys Gln Leu Ala Glu Tyr
            35                  40                  45

Ala Lys Ala Met Lys Gln Leu Ala Ile Trp Glu Thr Asn Asp Gly
    50                  55                  60

Lys Val Glu Leu Gln Ala Arg Ser Arg Ile Lys Trp Ala Ile Asp Tyr
65                  70                  75                  80

Ile Thr Lys Tyr Phe Phe Thr Glu Gly Ile Tyr Leu Gln Lys Arg Gln
                85                  90                  95

Arg Glu Gln Arg Leu Leu Glu Ser Tyr Arg Ala Glu Gly Lys Leu Gly
                100                 105                 110

Glu Val Gln Cys Arg Leu Met Glu Pro Pro Asp Arg Leu His Val
            115                 120                 125

Leu Asp Val Gly Ser Cys Phe Asn Pro Phe Ser Ser Ala Pro His Leu
    130                 135                 140

Glu Val Thr Ala Leu Asp Leu Cys Pro Ala Thr Glu Asp Val Leu Gln
145                 150                 155                 160

Ala Asp Phe Leu Lys Val Glu Val Val Pro Gly Ile Arg Glu Pro Glu
                165                 170                 175

Leu Glu Glu Gly Ser Val Arg Arg Leu Pro Ala Ser His Tyr Glu Cys
                180                 185                 190

Val Ile Phe Ser Leu Leu Leu Glu Tyr Met Pro Ser Ala Glu Gln Arg
            195                 200                 205

Leu Gln Cys Cys Leu Gln Ala Tyr Asp Leu Leu Pro Glu Gly Ile
    210                 215                 220

Leu Val Leu Ile Thr Pro Asp Ser Gln His Val Gly Lys Asn Ala His
225                 230                 235                 240

Leu Met Lys Asn Trp Arg Tyr Ser Leu Ala Arg Ile Gly Leu Leu Arg
                245                 250                 255

Val Arg Phe Glu Lys Leu Pro His Ile Ser Cys Met Val Phe Arg Lys
                260                 265                 270

Ala Ile Ser Arg Glu Leu Ser Gln His Trp Ala Ser Ile His Arg Glu
            275                 280                 285

Glu Gly Met Cys Glu Glu Ile Arg Ile Pro Gln Asp Asp Ser
    290                 295                 300

<210> SEQ ID NO 46
<211> LENGTH: 350
<212> TYPE: PRT
<213> ORGANISM: Hydra vulgaris

<400> SEQUENCE: 46

Lys Lys Phe Phe Met Phe Thr Met Asp Glu Ala Thr Lys Asn Ala Glu
1               5                   10                  15

Val Val Lys Lys Leu His Lys Thr Leu Arg Ser Lys Val Lys Lys Gly
            20                  25                  30

Tyr Pro Pro Asp Glu Val Trp Ala Asn Leu Leu Lys Asp Ser Asp Val
            35                  40                  45

Leu Ser Glu Tyr Ser Lys Ala Met Ser Ile Leu Ala Leu Gln Tyr Trp
    50                  55                  60

Pro Lys Asp Thr Ser Gln Ser Arg Ile Lys Trp Ala Tyr Asn Val Cys
65                  70                  75                  80

Leu Glu Tyr Phe Tyr Asn Gly Gly Ala Tyr Lys Ser Ala Gln Lys Tyr
                85                  90                  95

Phe Lys Gln Gln Met Tyr Ser Ser Leu Glu Lys Asn Ile Val Thr Glu
                100                 105                 110

Tyr Glu Lys Leu Thr Ile Glu Ser Glu Leu Arg Ile Phe Glu Arg Asp
            115                 120                 125

Trp Lys Ser Leu Ile Thr Glu Lys Ile Val Leu Leu Asp Val Gly Ser
        130                 135                 140

Cys Phe Asn Gly Phe Lys Glu Phe Asn Glu Phe Leu Val Phe Pro Ile
145                 150                 155                 160

Asp Ile Ala Pro Ala Thr Gln Asp Val Tyr Lys Leu Asp Phe Leu Asn
                165                 170                 175

Val Ala Phe Lys Glu Val Ser Gln Ser Phe Thr Ser Asp Gln Phe Thr
            180                 185                 190

Leu Val Thr Tyr Ile Arg Asp Asn Leu Thr Asp Ser Leu Leu Leu Lys
        195                 200                 205

Ala Val Phe Asp Val Val Phe Ser Leu Leu Leu Cys Tyr Leu Pro
210                 215                 220

Cys Pro Glu Gln Arg Leu Lys Cys Cys Ile Asn Ala His Ile Ser Leu
225                 230                 235                 240

Arg Leu Tyr Gly Leu Leu Ile Ile Ile Thr Pro Asp Ser Ser His Gln
                245                 250                 255

Asn Arg Asn Ala Lys Met Met Ala Ser Trp Lys Asn Ala Leu Glu Gly
            260                 265                 270

Ile Gly Phe Val Arg Tyr Lys Tyr Thr Lys Leu Glu His Phe His Cys
        275                 280                 285

Met Ala Phe Phe Lys Ala Asn Glu Thr Asn Ile Leu Leu Trp Glu Lys
290                 295                 300

Tyr Ser Arg Phe Leu Phe Ile Pro Gln Asp Phe Gln Glu Ile Lys Glu
305                 310                 315                 320

Glu Lys Val Asp Ile Asn Cys Ser Glu Glu Lys Phe Ser Ser Asn Tyr
                325                 330                 335

Asn Ile Glu Glu Leu Ile Gln Val Cys Asn Leu Ser Glu Leu
            340                 345                 350

<210> SEQ ID NO 47
<211> LENGTH: 405
<212> TYPE: PRT
<213> ORGANISM: Homo sapiens

<400> SEQUENCE: 47

Met Glu Pro Gly Ala Gly Gly Arg Asn Thr Ala Arg Ala Gln Arg Ala
1               5                   10                  15

Gly Ser Pro Asn Thr Pro Pro Arg Glu Gln Glu Arg Lys Leu Glu
            20                  25                  30

Gln Glu Lys Leu Ser Gly Val Val Lys Ser Val His Arg Arg Leu Arg
        35                  40                  45

Lys Lys Tyr Arg Glu Val Gly Asp Phe Asp Lys Ile Trp Arg Glu His
    50                  55                  60

Cys Glu Asp Glu Glu Thr Leu Cys Glu Tyr Ala Val Ala Met Lys Asn
65                  70                  75                  80

Leu Ala Asp Asn His Trp Ala Lys Thr Cys Glu Gly Glu Gly Arg Ile
                85                  90                  95

Glu Trp Cys Cys Ser Val Cys Arg Glu Tyr Phe Gln Asn Gly Gly Lys
            100                 105                 110

-continued

```
Arg Lys Ala Leu Glu Lys Asp Glu Lys Arg Ala Val Leu Ala Thr Lys
            115                 120                 125

Thr Thr Pro Ala Leu Asn Met His Glu Ser Ser Gln Leu Glu Gly His
130                 135                 140

Leu Thr Asn Leu Ser Phe Thr Asn Pro Glu Phe Ile Thr Glu Leu Leu
145                 150                 155                 160

Gln Ala Ser Gly Lys Ile Arg Leu Leu Asp Val Gly Ser Cys Phe Asn
                165                 170                 175

Pro Phe Leu Lys Phe Glu Glu Phe Leu Thr Val Gly Ile Asp Ile Val
            180                 185                 190

Pro Ala Val Glu Ser Val Tyr Lys Cys Asp Phe Leu Asn Leu Gln Leu
        195                 200                 205

Gln Gln Pro Leu Gln Leu Ala Gln Asp Ala Ile Asp Ala Phe Leu Lys
    210                 215                 220

Gln Leu Lys Asn Pro Ile Asp Ser Leu Pro Gly Glu Leu Phe His Val
225                 230                 235                 240

Val Val Phe Ser Leu Leu Ser Tyr Phe Pro Ser Pro Tyr Gln Arg
                245                 250                 255

Trp Ile Cys Cys Lys Lys Ala His Glu Leu Leu Val Leu Asn Gly Leu
            260                 265                 270

Leu Leu Ile Ile Thr Pro Asp Ser Ser His Gln Asn Arg His Ala Met
        275                 280                 285

Met Met Lys Ser Trp Lys Ile Ala Ile Glu Ser Leu Gly Phe Lys Arg
    290                 295                 300

Phe Lys Tyr Ser Lys Phe Ser His Met His Leu Met Ala Phe Arg Lys
305                 310                 315                 320

Ile Ser Leu Lys Thr Thr Ser Asp Leu Val Ser Arg Asn Tyr Pro Gly
                325                 330                 335

Met Leu Tyr Ile Pro Gln Asp Phe Asn Ser Ile Glu Asp Glu Glu Tyr
            340                 345                 350

Ser Asn Pro Ser Cys Tyr Val Arg Ser Asp Ile Glu Asp Glu Gln Leu
        355                 360                 365

Ala Tyr Gly Phe Thr Glu Leu Pro Asp Ala Pro Tyr Asp Ser Asp Ser
    370                 375                 380

Gly Glu Ser Gln Ala Ser Ser Ile Pro Phe Tyr Glu Leu Glu Asp Pro
385                 390                 395                 400

Ile Leu Leu Leu Ser
                405

<210> SEQ ID NO 48
<211> LENGTH: 240
<212> TYPE: PRT
<213> ORGANISM: Escherichia coli

<400> SEQUENCE: 48

Met Asn Ala Glu Lys Ser Pro Val Asn His Asn Val Asp His Glu Glu
1               5                   10                  15

Ile Ala Lys Phe Glu Ala Val Ala Ser Arg Trp Trp Asp Leu Glu Gly
            20                  25                  30

Glu Phe Lys Pro Leu His Arg Ile Asn Pro Leu Arg Leu Gly Tyr Ile
        35                  40                  45

Ala Glu Arg Ala Gly Gly Leu Phe Gly Lys Lys Val Leu Asp Val Gly
    50                  55                  60
```

```
Cys Gly Gly Gly Ile Leu Ala Glu Ser Met Ala Arg Glu Gly Ala Thr
 65                  70                  75                  80

Val Thr Gly Leu Asp Met Gly Phe Glu Pro Leu Gln Val Ala Lys Leu
                 85                  90                  95

His Ala Leu Glu Ser Gly Ile Gln Val Asp Tyr Val Gln Glu Thr Val
            100                 105                 110

Glu Glu His Ala Ala Lys His Ala Gly Gln Tyr Asp Val Val Thr Cys
            115                 120                 125

Met Glu Met Leu Glu His Val Pro Asp Pro Gln Ser Val Val Arg Ala
130                 135                 140

Cys Ala Gln Leu Val Lys Pro Gly Gly Asp Val Phe Phe Ser Thr Leu
145                 150                 155                 160

Asn Arg Asn Gly Lys Ser Trp Leu Met Ala Val Val Gly Ala Glu Tyr
                165                 170                 175

Ile Leu Arg Met Val Pro Lys Gly Thr His Asp Val Lys Lys Phe Ile
            180                 185                 190

Lys Pro Ala Glu Leu Leu Gly Trp Val Asp Gln Thr Ser Leu Lys Glu
            195                 200                 205

Arg His Ile Thr Gly Leu His Tyr Asn Pro Ile Thr Asn Thr Phe Lys
210                 215                 220

Leu Gly Pro Gly Val Asp Val Asn Tyr Met Leu His Thr Gln Asn Lys
225                 230                 235                 240

<210> SEQ ID NO 49
<211> LENGTH: 218
<212> TYPE: PRT
<213> ORGANISM: Methanococcus maripaludis

<400> SEQUENCE: 49

Met Ser Glu Asn Lys Lys Phe Asp Lys Lys Gly Ala Lys Asn Met
 1               5                  10                  15

Asp Glu Ile Ser Lys Thr Leu Phe Ala Pro Ile Tyr Pro Ile Ile Ala
                 20                  25                  30

Glu Asn Ile Ile Asn Arg Phe Gly Ile Thr Ala Gly Asn Cys Ile Asp
             35                  40                  45

Ile Gly Ser Gly Pro Gly Ala Leu Ser Ile Ala Leu Ala Lys Gln Ser
 50                  55                  60

Asp Phe Ser Ile Arg Ala Leu Asp Phe Ser Lys His Met Asn Glu Ile
 65                  70                  75                  80

Ala Leu Lys Asn Ile Ala Asp Ala Asp Leu Asn Asp Arg Ile Gln Ile
                 85                  90                  95

Val Gln Gly Asp Val His Asn Ile Pro Ile Glu Asp Asn Tyr Ala Asp
            100                 105                 110

Leu Ile Val Ser Arg Gly Ser Val Phe Phe Trp Glu Asp Val Thr Thr
            115                 120                 125

Ala Phe Arg Glu Ile Tyr Arg Ile Leu Lys Ser Gly Gly Lys Thr Tyr
130                 135                 140

Ile Gly Gly Gly Phe Gly Asn Lys Glu Leu Arg Asp Ser Ile Ser Ala
145                 150                 155                 160

Glu Met Ile Arg Lys Asn Pro Asp Trp Lys Glu Phe Asn Arg Lys Asn
                165                 170                 175

Ile Ser Gln Glu Asn Val Glu Arg Phe Gln Asn Val Leu Asp Glu Ile
            180                 185                 190
```

```
Gly Val Ser Ser Tyr Glu Ile Ile Leu Glu Asp Glu Gly Phe Trp Ile
        195                 200                 205

Ile Ile Ser Lys Thr Asp Gln Glu Val Ile
        210                 215

<210> SEQ ID NO 50
<211> LENGTH: 266
<212> TYPE: PRT
<213> ORGANISM: Plasmodium falciparum

<400> SEQUENCE: 50

Met Thr Leu Ile Glu Asn Leu Asn Ser Asp Lys Thr Phe Leu Glu Asn
1               5                   10                  15

Asn Gln Tyr Thr Asp Glu Gly Val Lys Val Tyr Glu Phe Ile Phe Gly
            20                  25                  30

Glu Asn Tyr Ile Ser Ser Gly Leu Glu Ala Thr Lys Lys Ile Leu
        35                  40                  45

Ser Asp Ile Glu Leu Asn Glu Asn Ser Lys Val Leu Asp Ile Gly Ser
    50                  55                  60

Gly Leu Gly Gly Gly Cys Met Tyr Ile Asn Glu Lys Tyr Gly Ala His
65                  70                  75                  80

Thr His Gly Ile Asp Ile Cys Ser Asn Ile Val Asn Met Ala Asn Glu
                85                  90                  95

Arg Val Ser Gly Asn Asn Lys Ile Ile Phe Glu Ala Asn Asp Ile Leu
            100                 105                 110

Thr Lys Glu Phe Pro Glu Asn Asn Phe Asp Leu Ile Tyr Ser Arg Asp
        115                 120                 125

Ala Ile Leu His Leu Ser Leu Glu Asn Lys Asn Lys Leu Phe Gln Lys
    130                 135                 140

Cys Tyr Lys Trp Leu Lys Pro Thr Gly Thr Leu Leu Ile Thr Asp Tyr
145                 150                 155                 160

Cys Ala Thr Glu Lys Glu Asn Trp Asp Asp Glu Phe Lys Glu Tyr Val
                165                 170                 175

Lys Gln Arg Lys Tyr Thr Leu Ile Thr Val Glu Glu Tyr Ala Asp Ile
            180                 185                 190

Leu Thr Ala Cys Asn Phe Lys Asn Val Val Ser Lys Asp Leu Ser Asp
        195                 200                 205

Tyr Trp Asn Gln Leu Leu Glu Val Glu His Lys Tyr Leu His Glu Asn
    210                 215                 220

Lys Glu Glu Phe Leu Lys Leu Phe Ser Glu Lys Phe Ile Ser Leu
225                 230                 235                 240

Asp Asp Gly Trp Ser Arg Lys Ile Lys Asp Ser Lys Arg Lys Met Gln
                245                 250                 255

Arg Trp Gly Tyr Phe Lys Ala Thr Lys Asn
            260                 265
```

METHODS OF IDENTIFYING MODULATORS OF SAMTOR-GATOR1 INTERACTION AND USE OF SAME TO MODULATE MTORC1

RELATED APPLICATIONS

This application claims the benefit of U.S. Provisional Application No. 62/574,623, filed on Oct. 19, 2017. The entire teachings of the above application are incorporated herein by reference.

GOVERNMENT SUPPORT

This invention was made with government support under Grant Nos. R01CA103866, R37AI47389, T32GM007753, F30CA210373, and U41HG006673 awarded by the National Institutes of Health and Grant No. W81XWH-07-0448 awarded by the Department of Defense. The government has certain rights in the invention.

BACKGROUND OF THE INVENTION

The mechanistic target of rapamycin complex 1 (mTORC1) protein kinase is the central component of a pathway that regulates anabolic and catabolic processes in response to environmental signals, including growth factors and nutrients (1-3). Amino acids promote the translocation of mTORC1 to the lysosomal surface, where its activator Rheb resides. This localization depends on the heterodimeric Rag GTPases, which consist of RagA or RagB bound to RagC or RagD (4, 5).

The amino acid sensing pathway upstream of mTORC1 is complicated, with several multi-component complexes regulating the Rag heterodimer, each likely conveying a distinct amino acid input. GATOR1 and FLCN-FNIP are GTPase activating proteins (GAPs) for RagA/B and RagC/D, respectively (6, 7), while Ragulator tethers the Rags to the lysosomal surface and also has nucleotide exchange activity (8, 9). The newly discovered KICSTOR complex binds GATOR1 and recruits it to the lysosome, and, like GATOR1, is necessary for amino acid starvation to inhibit mTORC1 signaling (7, 10, 11). The molecular function of GATOR2 is unknown, but it is required for pathway activity and might act upstream of GATOR1 (7).

Leucine and arginine are well-established activators of mTORC1 signaling, and recent work has shed light on the molecular mechanisms involved. The lysosomal transmembrane protein SLC38A9 is a lysosomal arginine sensor and interacts with Ragulator (12-14), while Sestrin2 and CASTOR1 are cytosolic leucine and arginine sensors, respectively, that bind to and inhibit the function of GATOR2 in the absence of their cognate amino acids (15-18). If, and how, other amino acids impact mTORC1 signaling is unclear.

SUMMARY OF THE INVENTION mTOR complex 1 (mTORC1) regulates cell growth and metabolism in response to multiple environmental cues. Amino acids signal via the Rag GTPases to promote the localization of mTORC1 to the lysosomal surface, its site of activation. Here, we identify SAMTOR as a previously uncharacterized protein that inhibits mTORC1 signaling by interacting with GATOR1, the GTPase activating protein (GAP) for RagA/B. The methyl donor S-adenosylmethionine (SAM) disrupts the SAMTOR-GATOR1 complex by binding directly to SAMTOR with a dissociation constant of approximately 7 μM. In cells, methionine starvation reduces SAM levels below this dissociation constant and promotes the association of SAMTOR with GATOR1, thereby inhibiting mTORC1 signaling in a SAMTOR-dependent fashion. Methionine-induced activation of mTORC1 requires the SAM binding capacity of SAMTOR. Thus, SAMTOR is a SAM sensor that links methionine and one carbon metabolism to mTORC1 signaling.

In some aspects, the disclosure provides a method of identifying a test compound as an activator of mTORC1 activity. In one aspect of these embodiments, the method comprises the steps of:
  a) providing a mixture comprising:
    (i) a first polypeptide comprising a GATOR1-KICSTOR-binding fragment of SAMTOR, or a polypeptide having at least 80% homology to a fragment of SAMTOR that retains the ability to bind GATOR1-KICSTOR;
    (ii) a second polypeptide or protein complex comprising a SAMTOR-binding fragment of a GATOR1-KICSTOR complex, or a polypeptide or protein complex having at least 80% homology to a fragment of GATOR1-KICSTOR complex that retains the ability to bind to SAMTOR; and
    (iii) a test compound
  under conditions that allow the first polypeptide to associate with the second polypeptide or protein complex; and
  b) determining whether the amount of the first polypeptide associated with the second polypeptide or protein complex is altered in the presence of the test compound as compared to either the absence of the test compound or the presence of a negative control, wherein if the amount of association is decreased the test compound is identified as an activator of mTORC1 activity.

In some aspects, the disclosure provides a method of identifying a test compound as an inhibitor of mTORC1 activity. In one aspect of these embodiments, the method comprises the steps of:
  a) providing a mixture comprising:
    (i) a first polypeptide comprising a GATOR1-KICSTOR-binding fragment of SAMTOR, or a polypeptide having at least 80% homology to a fragment of SAMTOR that retains the ability to bind GATOR1-KICSTOR;
    (ii) a second polypeptide or protein complex comprising a SAMTOR-binding fragment of a GATOR1-KICSTOR complex, or a polypeptide or protein complex having at least 80% homology to a fragment of GATOR1-KICSTOR complex that retains the ability to bind to SAMTOR; and
    (iii) a test compound,
  under conditions that prevent the first polypeptide from associating with the second polypeptide or protein complex; and
  b) determining whether the amount of the first polypeptide associated with the second polypeptide or protein complex is altered in the presence of the test compound as compared to either the absence of the test compound or the presence of a negative control, wherein if the amount of association is increased the test compound is identified as an inhibitor of mTORC1 activity.

In some embodiments, the methods further comprise pre-incubating the first polypeptide with the second polypeptide prior to step (a). In other embodiments, the methods further comprise pre-incubating the first polypeptide with the test compound prior to step (a). In still other embodiments, the methods further comprise pre-incubating the second polypeptide with the test compound prior to step (a). In some embodiments, the methods further comprise pre-incubating the test compound with SAM prior to step (a).

In other embodiments, the invention provides a method of agonizing mTORC1 activity in a cell by contacting the cell with an agent that reduces or antagonizes the interaction of SAMTOR with a GATOR1-KICSTOR complex.

In still other embodiments, the invention provides method of treating a disease, condition or disorder in a subject who would benefit from increased mTORC1 activity comprising the step of administering to the subject an agent that reduces or antagonizes the interaction of SAMTOR with a GATOR1-KICSTOR complex.

In other embodiments, the invention provides a method of decreasing mTORC1 activity in a cell by contacting the cell with an agent that induces or increases the interaction of SAMTOR with a GATOR1-KICSTOR complex.

In still other embodiments, the invention provides a method of treating a disease, condition or disorder in a subject who would benefit from decreasing mTORC1 activity comprising the step of administering to the subject an agent that induces or increases the interaction of SAMTOR with a GATOR1-KICSTOR complex.

In other embodiments, the invention provides a method of identifying a test compound as a modulator of mTORC1 by determining if the test compound can decrease or increase the affinity of SAMTOR for SAM. In one aspect of these embodiments, the method comprises the steps of:
 a. providing a mixture comprising:
  i. a SAMTOR polypeptide, or a polypeptide having at least 80% homology to a fragment of SAMTOR that retains the ability to bind SAM;
  ii. SAM; and
  iii. a test compound,
 under conditions that allow SAM to bind to the polypeptide; and
 b. determining whether the amount of SAM bound to the polypeptide is altered in the presence of the test compound as compared to either the absence of the test compound or the presence of a negative control, wherein if the amount of binding is decreased in the presence of test compound, the test compound is identified as an inhibitor of mTORC1 activity; and if the amount of binding is increased in the presence of the test compound, the test compound is identified as an activator of mTORC1 activity.

In some embodiments, the method further includes incubating the mixture of step (a) with a GATOR1-KICSTOR complex. In further embodiments, the method includes determining the ability of SAMTOR to associate with the GATOR1-KICSTOR complex.

In other embodiments, the invention provides method of agonizing (e.g., maintaining or increasing) mTORC1 activity in a cell comprising the step of contacting the cell with an agent that increases the binding of SAM to SAMTOR.

In other embodiments, the invention provides a method of treating a disease, condition, or disorder in a subject who would benefit from increased mTORC1 activity comprising the step of administering to the subject an agent that increases the binding of SAM to SAMTOR.

In still other embodiments, the invention provides a method of decreasing mTORC1 activity in a cell comprising the step of contacting the cell with an agent that decreases the binding of SAM to SAMTOR.

In other embodiments, the invention provides a method of treating a disease, condition or disorder in a subject who would benefit from decreased mTORC1 activity comprising the step of administering to the subject an agent that decreases the binding of SAM to SAMTOR.

In still other embodiments, the invention provides a composition comprising SAMTOR or SAM formulated with one or more pharmaceutically acceptable carriers and/or excipients.

In other embodiments, the invention provides a composition comprising a polypeptide comprising a GATOR1-KICSTOR-binding fragment of SAMTOR. In still other embodiments, the invention provides a composition comprising a polypeptide having at least 80% homology to SAMTOR that retains the ability to bind GATOR1-KICSTOR. The polypeptide is formulated with one or more pharmaceutically acceptable carriers and/or excipients.

In still other embodiments, the invention provides a method of identifying a modulator of mTORC1 activity comprising the steps of contacting a test compound with SAMTOR or a fragment or mutant thereof that possesses an activity or characteristic of SAMTOR; measuring an activity or characteristic of SAMTOR in the presence of the test compound; and comparing the measured activity or characteristic with the same activity or characteristic in the absence of the test compound, thereby determining whether the test compound is a modulator of SAMTOR and therefore is a modulator of mTORC1.

In some embodiments, the test compound is contacted with SAMTOR or a fusion protein comprising SAMTOR; and a heterologous fusion partner. The heterologous fusion partner may be selected from a N-terminal His tag, a N-terminal poly-His tag, an epitope tag, a ligand tag, a N- or C-terminal plasma membrane signal sequence, a fluorescent polypeptide, or a luminescent polypeptide.

The above discussed, and many other features and attendant advantages of the present inventions will become better understood by reference to the following detailed description of the invention.

BRIEF DESCRIPTION OF THE DRAWINGS

The patent or application file contains at least one drawing executed in color. Copies of this patent or patent application publication with color drawings will be provided by the Office upon request and payment of the necessary fee.

FIGS. 1A-1D show SAMTOR interacts with GATOR1 and KICSTOR. FIG. 1A demonstrates GATOR1 and KICSTOR, but not GATOR2, co-immunoprecipitate SAMTOR. FLAG-immunoprecipitates were prepared from HEK-293T cell lines that stably expressed FLAG-tagged metap2 or Kaptin, or had endogenously FLAG-tagged Depdc5 or WDR59. FLAG-immunoprecipitates and lysates were analyzed by immunoblotting for the indicated proteins. FLAG-metap2 served as a negative control. Depdc5 and Nprl3, WDR59 and WDR24, and Kaptin and SZT2 were used as representative components of the GATOR1, GATOR2, and KICSTOR complexes respectively. Short or long exposure indicates relative blot exposure times. FIG. 1B shows SAMTOR co-immunoprecipitates GATOR1 and KICSTOR, and the interaction requires both GATOR1 and KICSTOR but not GATOR2. FLAG-immunoprecipitates were prepared from wild-type, Nprl3-deficient, SZT2-deficient, or WDR24-deficient HEK-293T cells transiently expressing the indicated cDNAs. FLAG-immunoprecipitates and lysates were analyzed as in (FIG. 1A). FIG. 1C provides a model of SAMTOR interacting with GATOR1 and KICSTOR. FIG. 1D depicts the presence or absence of gene orthologs of SAMTOR in several model organisms.

FIG. 2A shows transient overexpression of SAMTOR inhibits mTORC1 signaling. FLAG-immunoprecipitates were prepared from HEK-293T cells transfected with 2 ng of the FLAG-S6K1 cDNA along with either the HA-metap2 cDNA or increasing amounts of the HA-SAMTOR cDNA. FLAG-immunoprecipitates and cell lysates were analyzed by immunoblotting for the phosphorylation states and levels of the indicated proteins. FIG. 2B shows overexpression of GFP-SAMTOR displaces mTOR from lysosomes, similar to that of GFP-Sestrin2. Wild-type HEK-293T cells transiently expressing GFP-metap2, GFP-SAMTOR, or GFP-Sestrin2 were processed for immunofluorescence detection of mTOR and the lysosomal marker LAMP2. In all images, insets represent selected fields magnified 3.07× as well as their overlays. Scale bar represents 10 µm. FIG. 2C shows SAMTOR functions upstream of the Rag GTPases to regulate the mTORC1 pathway. HEK-293T cells expressing the indicated cDNAs were starved of amino acids for 50 minutes or starved and restimulated with amino acids for 10 minutes. FLAG-immunoprecipitates and cell lysates were analyzed as in (FIG. 2A). FIG. 2D shows SAMTOR functions upstream of GATOR1 and KICSTOR. FLAG-immunoprecipitates and cell lysates prepared from wild-type or Nprl3-deficient or SZT2-deficient HEK-293T cell lines expressing the indicated cDNAs were analyzed as in (FIG. 2A).

FIG. 3A provides a schematic of the human SAMTOR protein indicating the Class I Rossmann fold methyltransferase domain. Shown is an alignment of partial sequences of this domain from SAMTOR in indicated species. Amino acid positions are colored from white to blue in order of increasing sequence similarity. Orange dots denote the G172 and D190 residues of human SAMTOR. FIG. 3B shows SAMTOR binds SAM and SAH. FLAG-SAMTOR protein prepared from HEK-293F cells transiently expressing the FLAG-SAMTOR cDNA was further purified by size-exclusion chromatography. The protein was analyzed by SDS-PAGE followed by Coomassie blue staining. Binding assays were performed with purified FLAG-SAMTOR incubated with 5 µM [$^3$H]SAM and indicated concentrations of unlabeled SAM or SAH. Values for each point are mean±SD of three technical replicates from one representative experiment. The experiment was performed twice. FIG. 3C demonstrates SAM and SAH disrupt the interaction of SAMTOR with GATOR1 in vitro. FLAG-immunoprecipitates were prepared from the endogenously FLAG-tagged Depdc5 HEK-293T cells. SAM and SAH were added directly to the immunoprecipitates at the indicated concentrations during the third wash of the immunoprecipitates. FLAG-immunoprecipitates and cell lysates were analyzed by immunoblotting for the levels of the indicated proteins. FIG. 3D shows 100 µM SAM or SAH, but not 1 mM methionine, homocysteine, adenosine, 5-methylthioadenosine, leucine, or isoleucine, disrupt the interaction between SAMTOR and GATOR1. The experiment was performed and analyzed as in (FIG. 3C). FIG. 3E demonstrates wild type HA-SAMTOR, but not HA-SAMTOR G172A or D190A, binds SAM. HA tagged wild-type and mutant SAMTOR proteins were prepared from HEK-293T cells expressing the indicated cDNAs and binding assays were performed as in (FIG. 3B) with the indicated concentrations of labeled and unlabeled SAM except that the HA tagged proteins were not subjected to size-exclusion chromatography. A representative experiment is shown and values are mean±SD of three technical replicates. Two-tailed t tests were used for comparisons between two groups. The asterisk denotes p<0.001; ns, not significant. The experiment was repeated three times. FIG. 3F shows HA-SAMTOR G172A and D190A co-immunoprecipitate more endogenous GATOR1 and KICSTOR than wild-type SAMTOR and the interactions are insensitive to SAM added in vitro. HA-immunoprecipitates and cell lysates were prepared from HEK-293T cells transiently expressing wild-type or the G172A or D190A mutant HA-SAMTOR. SAM was added to the immunoprecipitates where indicated. HA-immunoprecipitates and cell lysates were analyzed as (FIG. 3C). FIG. 3G shows HA-SAMTOR G172A and D190A inhibit mTORC1 activity to similar extents as wild-type SAMTOR. FLAG-immunoprecipitates were prepared from HEK-293T cells transfected with 2 ng of the FLAG-S6K cDNA along with the cDNAs for the indicated HA tagged wild-type or mutant SAMTOR. FLAG-immunoprecipitates and cell lysates were analyzed by immunoblotting for the phosphorylation states and levels of the indicated proteins.

FIG. 4A shows HEK-293T cells were incubated with or without methionine for 2 hours prior to sample preparation for LC/MS-based measurements of the absolute amounts of the indicated metabolites. Cell volumes were determined by Coulter counter and used to calculate whole cell concentrations. FIG. 4B demonstrates methionine starvation increases the interaction between SAMTOR and GATOR1. HEK-293T cells transiently expressing HA-tagged metap2 or SAMTOR were kept in growth median (RPMI) or starved of methionine for 2 hours (−Met) or starved for methionine for 2 hours and then restimulated for 20 minutes with 100 µM methionine (+Met) or 1 mM SAM (+SAM). HA-immunoprecipitates and cell lysates were analyzed by immunoblotting for the levels of the indicated proteins. FIG. 4C shows in SAMTOR-depleted cells, the mTORC1 pathway is resistant to methionine starvation. HEK-293T cells stably co-expressing Cas9 and the indicated guides were incubated in media with or without methionine for 2 hours. Cell lysates were analyzed by immunoblotting for the phosphorylation states and the levels of the indicated proteins. FIG. 4D shows the loss of SAMTOR does not affect the sensitivity of the mTORC1 pathway to leucine or arginine starvation. Wild-type or SAMTOR-deficient HEK-293T cells were starved for the indicated amino acid for 2 hours. Cell lysates were analyzed by immunoblotting for the phosphorylation states and the levels of the indicated proteins. FIG. 4E demonstrates in cells without SAMTOR, mTOR co-localizes with lysosomes even upon methionine starvation. SAMTOR-deficient or control HEK-293T cells were treated as indicated for 2 hours prior to processing for immunofluorescence detection of mTOR and the lysosomal marker LAMP2. In all images, insets represent selected fields magnified 3.07× as well as their overlays. Scale bar represents 10 µm. FIG. 4F shows re-expression in SAMTOR-null cells of wild-type SAMTOR, but not G172A SAM-binding deficient mutant of SAMTOR, restored the capacity of the mTORC1 pathway to sense methionine sufficiency. SAMTOR-null cells were co-transfected with a cDNA for FLAG-S6K1 along with the indicated HA-tagged cDNAs and cells were treated as in (FIG. 4C) prior to preparing lysates and FLAG-immunoprecipitates. FLAG-immunoprecipitates and cell lysates were analyzed by immunoblotting for the phosphorylation states and the levels of the indicated proteins. FIG. 4G demonstrates in *Drosophila* S2R+ cells depleted of dSamtor or dSesn, the dTOR pathway is resistant to methionine and leucine starvation, respectively. S2R+ cells were transfected with dsRNAs targeting the indicated mRNAs and starved for 1 hour for the indicated amino acid. Cell lysates were analyzed by immunoblotting for the phosphorylation states and the levels of the indicated proteins. FIG. 4H shows acute loss of MAT2A using a doxycycline-suppressible system attenuates the capacity of mTORC1 to sense methionine, but leaves SAM signaling largely intact. MAT2A dox-off HEK-293T cells were treated with 30 ng/mL doxycycline for 50 hours prior to starving them as in (FIG. 4C). Cell lysates were analyzed by immunoblotting for the phosphorylation states and the levels of the indicated proteins. FIG. 4I provides a model depicting how SAM sensing by SAMTOR signals methionine levels to mTORC1.

FIGS. 5A-5B provide sequence alignments. FIG. 5A provides a sequence alignment of SAMTOR homologues from various organisms. Amino acid positions are colored white and blue according to increasing sequence similarity. Two residues (G172 and D190) significant for SAM binding capacity are indicated with orange dots. FIG. 5B provides a sequence alignment of human SAMTOR with three methyltransferases selected from the list of proteins predicted by HHPred as having secondary structure similarity to SAMTOR. Two residues (G172 and D190) significant for SAM binding capacity are indicated with orange dots.

FIG. 6A demonstrates in HeLa cells with reduced SAMTOR expression the mTORC1 pathway is resistant to methionine starvation. Two SAMTOR-deficient HeLa cell lines generated using CRISPR/Cas9 were treated as in FIG. 4C. Cell lysates were analyzed by immunoblotting for the phosphorylation states and levels of the indicated proteins. FIG. 6B demonstrates in MEFs with reduced SAMTOR expression the mTORC1 pathway is resistant to methionine starvation. Cells were prepared via the stable expression of Cas9 along with the indicated guide. Cells were treated as in FIG. 4C and the lysates were analyzed by immunoblotting for the phosphorylation states and levels of the indicated proteins. FIG. 6C shows the loss of SAMTOR in HeLa cells does not impact the regulation of mTORC1 by growth factors. SAMTOR-deficient cells were incubated in the presence or absence of insulin for 1 hour. Cell lysates were analyzed by immunoblotting for the indicated proteins. FIG. 6D demonstrates methionine starvation causes SAMTOR protein levels to drop in a proteasome dependent fashion. 10 µM of the indicated proteasome inhibitors was added to HEK-293T cells cultured in media with or without methionine for 2 hours. Cell lysates were analyzed by immunoblotting for the phosphorylation states and levels of the indicated proteins. FIG. 6E shows mRNA levels of dSamtor and dSesn in Drosophila S2R+ cells after transfection of the indicated dsRNA. cDNA from transfected cells was synthesized and used for quantitative PCR. Reported values are mean±SD of three technical replicates of ΔΔCt values, using alpha-tubulin mRNA as an internal standard.

DETAILED DESCRIPTION OF THE INVENTION

Figure 1A:
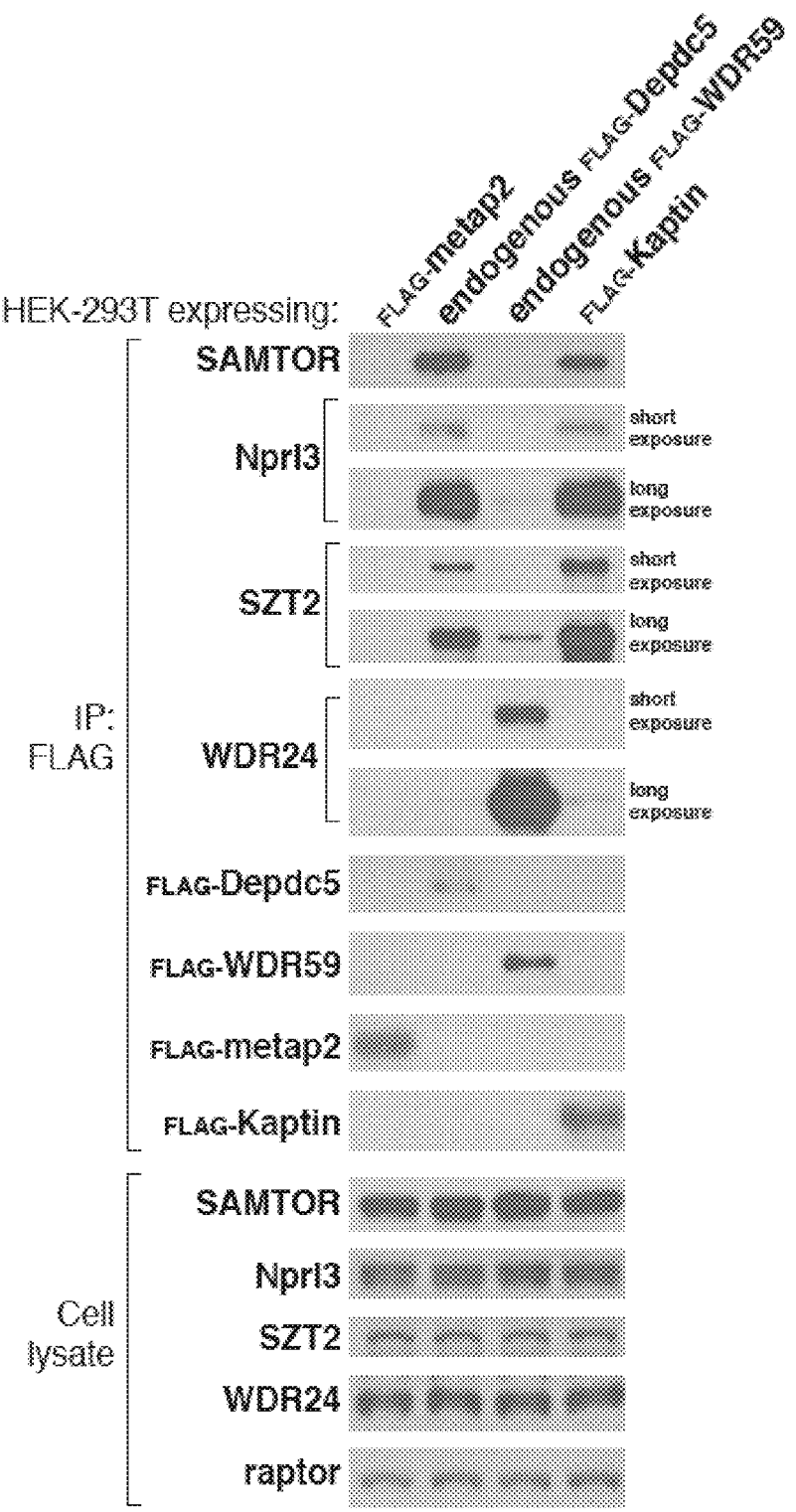

The practice of the present invention will typically employ, unless otherwise indicated, conventional techniques of cell biology, cell culture, molecular biology, transgenic biology, microbiology, recombinant nucleic acid (e.g., DNA) technology, immunology, and RNA interference (RNAi) which are within the skill of the art. Non-limiting descriptions of certain of these techniques are found in the following publications: Ausubel, F., et al., (eds.), Current Protocols in Molecular Biology, Current Protocols in Immunology, Current Protocols in Protein Science, and Current Protocols in Cell Biology, all John Wiley & Sons, N.Y., edition as of December 2008; Sambrook, Russell, and Sambrook, Molecular Cloning: A Laboratory Manual, 3rd ed., Cold Spring Harbor Laboratory Press, Cold Spring Harbor, 2001; Harlow, E. and Lane, D., Antibodies—A Laboratory Manual, Cold Spring Harbor Laboratory Press, Cold Spring Harbor, 1988; Freshney, R. I., "Culture of Animal Cells, A Manual of Basic Technique", 5th ed., John Wiley & Sons, Hoboken, N.J., 2005. Non-limiting information regarding therapeutic agents and human diseases is found in Goodman and Gilman's The Pharmacological Basis of Therapeutics, 11th Ed., McGraw Hill, 2005, Katzung, B. (ed.) Basic and Clinical Pharmacology, McGraw-Hill/Appleton & Lange; 10th ed. (2006) or 11th edition (July 2009). Non-limiting information regarding genes and genetic disorders is found in McKusick, V. A.: Mendelian Inheritance in Man. A Catalog of Human Genes and Genetic Disorders. Baltimore: Johns Hopkins University Press, 1998 (12th edition) or the more recent online database: Online Mendelian Inheritance in Man, OMIM™. McKusick-Nathans Institute of Genetic Medicine, Johns Hopkins University (Baltimore, Md.) and National Center for Biotechnology Information, National Library of Medicine (Bethesda, Md.), as of May 1, 2010, ncbi.nlm.nih.gov/omim/ and in Online Mendelian Inheritance in Animals (OMIA), a database of genes, inherited disorders and traits in animal species (other than human and mouse), at omia.angis.org.au/contact.shtml. All patents, patent applications, and other publications (e.g., scientific articles, books, websites, and databases) mentioned herein are incorporated by reference in their entirety. In case of a conflict between the specification and any of the incorporated references, the specification (including any amendments thereof, which may be based on an incorporated reference), shall control. Standard art-accepted meanings of terms are used herein unless indicated otherwise. Standard abbreviations for various terms are used herein.

As used herein "modulating" (and verb forms thereof, such as "modulates") means causing or facilitating a qualitative or quantitative change, alteration, or modification in a molecule, a process, pathway, or phenomenon of interest. Without limitation, such change may be an increase, decrease, a change in binding characteristics, or change in relative strength or activity of different components or branches of the process, pathway, or phenomenon.

The term "inhibitor" (and verb forms thereof, such as "inhibits"), as used herein means an agent that (a) reduces one or more activities normally associated with the protein being inhibited; (b) reduces or otherwise interferes with the ability of the protein being inhibited to associate with, e.g., bind to, another protein or ligand or nucleic acid; and/or (c) reduces the transcription or expression from a gene that encodes the protein being inhibited.

The terms "activator" and "agonist" (and verb forms thereof, such as "activates" and "agonizes"), as used herein means an agent that (a) increases one or more activities normally associated with the protein being activated; (b) increases or otherwise enhances the ability of the protein being activated to associate with, e.g., bind to, another protein or ligand or nucleic acid; and/or (c) increases the transcription or expression from a gene that encodes the protein being activated.

In certain embodiments, modulating, inhibiting, activating and/or agonizing utilizing any of the activating, agonistic, or inhibitory systems, methods or agents described herein can be performed in vitro or ex vivo, for example, by contacting or exposing cells to the activating, agonistic, or inhibitory systems, methods or agents. In certain embodiments, modulating, inhibiting, activating and/or agonizing utilizing any of the activating, agonistic, or inhibitory systems, methods or agents described herein can be performed in vivo.

The term "GATOR1" refers to a protein complex of three different polypeptides: Depdc5, Nprl3, and Nprl2. GATOR1 forms a supercomplex with KICSTOR.

The term "KICSTOR" refers to a protein complex of four different polypeptides: Kaptin, ITFG2, C12orf66, and SZT2. The KICSTOR complex binds GATOR1 and recruits it to the lysosome.

The terms "SAMTOR" and "C7orf60" are used interchangeably herein. SAMTOR refers to a S-adenosylmethionine sensor upstream of mTORC1. As used herein, SAMTOR refers to a SAMTOR polypeptide, as well as other isoforms of SAMTOR. In some aspects, protein encoded by the C7orf60 gene (NCBI Gene ID: 154743) interacts with all known components of GATOR1 (Depdc5, Nprl3, and Nprl2) and KICSTOR (Kaptin, ITFG2, C12orf66, and SZT2). In certain aspects, the G271 site of SAMTOR is involved in the interaction with GATOR1 and KICSTOR.

The term "GATOR1-KICSTOR-binding fragment" refers to the minimal portion of SAMTOR or a polypeptide that is at least 80% homologous to the minimal portion of SAMTOR that specifically associates with one or more polypeptides of GATOR1 and/or KICSTOR. In some embodiments, the GATOR1-KICSTOR-binding fragment is a GATOR1-binding fragment and/or a KICSTOR-binding fragment.

The term "GATOR1-binding fragment" refers to the minimal portion of SAMTOR or a polypeptide that is at least 80% homologous to the minimal portion of SAMTOR that specifically associates with one or more polypeptides of GATOR1. In some embodiments, a GATOR1-binding fragment is the minimal portion of SAMTOR or a polypeptide that is at least 80% homologous to the minimal portion of SAMTOR that primarily associates with Depdc5. In some embodiments, a GATOR1-binding fragment is the minimal portion of SAMTOR or a polypeptide that is at least 80% homologous to the minimal portion of SAMTOR that primarily associates with Nprl3. In some embodiments, a GATOR1-binding fragment is the minimal portion of SAMTOR or a polypeptide that is at least 80% homologous to the minimal portion of SAMTOR that primarily associates with Nprl2.

The term "KICSTOR-binding fragment" refers to the minimal portion of SAMTOR or a polypeptide that is at least 80% homologous to the minimal portion of SAMTOR that specifically associates with one or more polypeptides of KICSTOR. In some embodiments, a KICSTOR-binding fragment is the minimal portion of SAMTOR or a polypeptide that is at least 80% homologous to the minimal portion of SAMTOR that primarily associates with Kaptin. In some embodiments, a KICSTOR-binding fragment is the minimal portion of SAMTOR or a polypeptide that is at least 80% homologous to the minimal portion of SAMTOR that primarily associates with ITFG2. In some embodiments, a KICSTOR-binding fragment is the minimal portion of SAMTOR or a polypeptide that is at least 80% homologous to the minimal portion of SAMTOR that primarily associates with C12orf66. In some embodiments, a KICSTOR-binding fragment is the minimal portion of SAMTOR or a polypeptide that is at least 80% homologous to the minimal portion of SAMTOR that primarily associates with SZT2.

The term "SAMTOR binding fragment" refers to the minimal portion of GATOR1 or a polypeptide or protein complex that is at least 80% homologous to the minimal portion of GATOR1 that specifically associates with SAMTOR and/or the minimal portion of KICSTOR or a polypeptide or protein complex that is at least 80% homologous to the minimal portion of KICSTOR that specifically associates with SAMTOR. In some embodiments, a SAMTOR-binding fragment is the minimal portion of Depdc5 that specifically associates with SAMTOR. In some embodiments, a SAMTOR-binding fragment is the minimal portion of Nprl3 that specifically associates with SAMTOR. In some embodiments, a SAMTOR-binding fragment is the minimal portion of Nprl2 that specifically associates with SAMTOR. In some embodiments, a SAMTOR-binding fragment is the minimal portion of Kaptin that specifically associates with SAMTOR. In some embodiments, a SAMTOR-binding fragment is the minimal portion of ITFG2 that specifically associates with SAMTOR. In some embodiments, a SAMTOR-binding fragment is the minimal portion of C12orf66 that specifically associates with SAMTOR. In some embodiments, a SAMTOR-binding fragment is the minimal portion of SZT2 that specifically associates with SAMTOR.

The term "at least 80% homologous" as used herein with respect to two polypeptide or proteins (the "query" sequence as compared to the "reference" sequence), means at least 80%, 85%, 86%, 87%, 88%, 89%, 90%, 91%, 92%, 93%, 94%, 95%, 96%, 97%, 98%, or 99% identity at an amino acid level as determined conventionally using known sequence alignment computer programs, such as the Bestfit program. When using Bestfit or other sequence alignment programs to determine whether a particular sequence is at least 80% identical to a reference sequence according to the present invention, the parameters are set such that the percentage of identity is calculated over the full length of the portion of the reference amino acid sequence that is homologous to the query sequence. For example, a query polypeptide sequence is at least 80%, 85%, 86%, 87%, 88%, 89%, 90%, 91%, 92%, 93%, 94%, 95%, 96%, 97%, 98%, or 99% identical at the amino acid level to a reference polypeptide sequence over at least 20%, 30%, 40%, 50%, 60%, 70%, 80%, 90%, 95%, 96%, 97%, 98%, 99%, or 100% of the reference polypeptide sequence.

"Conditions that allow the first polypeptide to associate with the second polypeptide or protein complex" are generally understood to be any conditions that would allow the first polypeptide to associate with the second polypeptide or protein complex. Such conditions would be readily understood by those of skill in the art. In some embodiments, the conditions include a buffered solution at physiological pH and salt concentrations characterized by the absence of compounds known to inhibit the SAMTOR-GATOR1 interaction. Exemplary conditions are those that are substantially free of S-adenosylmethionine (SAM) and/or analogs of SAM. In certain embodiments, such conditions are less than 1 nM of SAM and/or analogs of SAM. In certain embodiments, such conditions are 100% free of SAM and/or analogs of SAM. Exemplary conditions may further be those that are substantially free of S-adenosylhomocysteine (SAH) and/or analogs of SAH. "Analogs" include modified versions of SAM and/or SAH, as well as compounds identified by the assays of the invention as inhibitors of SAMTOR-GATOR1 interaction. The term "substantially free" as used herein with respect to SAM and/or analogs of SAM means a concentration of less than 100 nM.

"Conditions that prevent the first polypeptide from associating with the second polypeptide or protein complex" are generally understood to be any conditions that would inhibit the first polypeptide from associating with the second polypeptide or protein complex. Such conditions would be readily understood by those of skill in the art. Such conditions generally include a buffered solution at physiological pH and salt concentrations characterized by the presence of compounds known to inhibit the SAMTOR-GATOR1 interaction. Exemplary conditions are those that include the presence of S-adenosylmethionine (SAM) and/or analogs of SAM. In certain embodiments, such conditions are more than 1 nM, more than 100 nM, more than 1000 nM, or more than 5000 nM of SAM and/or analogs of SAM. Conditions may include more than 7 µM of SAM and/or analogs of SAM. Exemplary conditions may further be those that include the presence of S-adenosylhomocysteine (SAH) and/or analogs of SAH. "Analogs" include modified versions of SAM and/or SAH, as well as compounds identified by the assays of the invention as inhibitors of SAMTOR-GATOR1 interaction.

"Conditions that allow SAM to bind to the polypeptide" are generally understood to be any conditions that would allow SAM to bind to the polypeptide. Such conditions would be readily understood by those of skill in the art. Such conditions generally include a buffered solution at physiological pH and salt concentrations characterized by the absence of compounds known to inhibit the SAM-SAMTOR interaction.

The term "test compound" refers to any of a small molecule, nucleic acid, amino acid, metabolite, polypeptide, antibody and antibody-like molecules, aptamers, macrocycles, or other molecules. In certain embodiments, a test compound is a small organic molecule. In one aspect of these embodiments, the small organic molecule has a molecular weight of less than about 5,000 daltons. In certain embodiments, the test compound is other than a metabolite. In other embodiments, the small molecule is other than SAM or analogs of the foregoing.

In certain embodiments, SAMTOR is putative interaction partner of all known components of GATOR1 (Depdc5, Nprl3, Nprl2) and KICSTOR (Kaptin, ITFG2, C12orf66, SZT2). In certain aspects, SAMTOR inhibits the amino acid sensing pathway upstream of mTORC1. SAMTOR functions as a SAM sensor that signals methionine sufficiency to mTORC1.

In some embodiments, certain amino acid metabolites of methionine or cysteine (e.g., S-adenosylmethionine (SAM) or S-adenosylhomocysteine (SAH)) modulate the interaction of SAMTOR with GATOR1-KICSTOR. In certain embodiments, SAM is a regulator of the SAMTOR-GATOR1-KICSTOR interaction. In some embodiments, SAM disrupts the interaction between SAMTOR and GATOR1-KICSTOR. In some embodiments, the addition of SAM to a SAMTOR-GATOR1-KICSTOR complex is sufficient to dissociate GATOR1-KICSTOR from SAMTOR. In certain aspects, the amount of SAM added to the complex to disrupt the interaction is at least 5 µM, 10 µM, 25 µM, 50 µM, 75 µM, 100 µM, 150 µM, 200 µM, 250 µM, 300 µM, 350 µM, or 400 µM. In some aspects, the amount of SAM added to the complex to disrupt the interaction is between 1 µM to 400 µM, 5 µM to 250 µM, 10 µM to 100 µM, 15 µM to 75 µM, or 10 µM to 40 µM. In certain embodiments, half-maximal disruption occurs at a SAM concentration of 5 µM to 10 µM, or about 7 µM. In some aspects, the invention provides agents that compete with SAM for binding to SAMTOR. In other embodiments, SAM is pre-bound to SAMTOR thereby preventing SAMTOR from interacting with GATOR1-KICSTOR.

SAM disrupts the SAMTOR-GATOR1-KICSTOR interaction by binding to SAMTOR. In some aspects, SAM binds to SAMTOR with a dissociation constant of around 7 µM. In some aspects, SAMTOR binds SAM with a dissociation constant of around 7 µM. In some embodiments, SAMTOR binds SAM with a dissociation constant of 1 µM to 50 µM, 5 µM to 40 µM, or 10 µM to 35 µM. In some aspects, the $K_d$ of SAM for SAMTOR is approximately 7 µM.

In certain embodiments, SAMTOR is a negative regulator of the mTORC1 pathway. In some aspects, SAMTOR affects the capacity of the mTORC1 pathway to respond to SAM. In some embodiments, SAMTOR is a negative regulator of SAM signaling to mTORC1.

In some aspects, the disclosure provides a method of identifying a modulator of mTORC1 activity comprising the steps of contacting a test compound with SAMTOR or a fragment or mutant thereof that possesses an activity or characteristic of SAMTOR, measuring an activity or characteristic of SAMTOR in the presence of the test compound, and comparing the measured activity or characteristic with the same activity or characteristic in the absence of the test compound, thereby determining whether the test compound is a modulator of mTORC1 activity.

In some embodiments, one or more activities or characteristics of SAMTOR are measured and compared. The activities or characteristics of SAMTOR that are measured may include binding to SAM and/or binding to GATOR1-KICSTOR. Other activities or characteristics of SAMTOR that may be measured will be known by those of skill in the art.

These methods may employ cellular systems where the SAMTOR or a fragment or mutant thereof is engineered to reside at the plasma membrane (e.g., by fusion of the N-terminus to a plasma membrane signal sequence); non-mammalian cellular systems that are engineered to express the SAMTOR or a fragment or mutant thereof at the plasma membrane; in vitro systems where the SAMTOR or a fragment or mutant thereof is attached to a solid support; and in vitro systems where the SAMTOR or a fragment or mutant thereof is free in solution.

Activities or characteristics to be measured in these methods include uptake of labelled (e.g., radiolabelled, fluorescently labelled) metabolites (e.g., SAM) in cellular systems, uptake of sodium in cellular systems, changes in membrane potential across a membrane in cellular systems, binding of metabolites to SAMTOR or a fragment or mutant thereof in in vitro systems; binding of test compound to SAMTOR or a fragment or mutant thereof in in vitro systems; changes in the ability of SAMTOR or a fragment or mutant thereof to bind to GATOR1-KICSTOR in both in vivo and in vitro systems; and changes in one or more activities of mTORC1 (e.g., change in phosphorylation state of an mTORC1 substrate, such as S6K1). In certain embodiments, these methods are used to measure changes in the ability of SAMTOR or a fragment or mutant thereof to bind to GATOR1-KICSTOR in vitro.

The measurement of these activities may be achieved by scintillation counting for radiolabelled amino acids; flow cytometry, fluorescence microplate or with a spectrofluorophotometer for fluorescent amino acids and to measure changes in membrane potential (e.g., dyes that change fluorescence in response to changes in membrane potential, e.g., FLIPR dyes (Molecular Devices); patch clamping for measuring electrical currents across a membrane; solid phase surface plasmon resonance to measure changes in amino acid binding or direct binding of test compound; and mass spectrometry to measure changes in amino acid binding or direct binding of test compound.

In some aspects, the disclosure provides a method for modulating the level or activity of mTORC1 in a cell comprising contacting a cell with an agent or composition that modulates (e.g., decreases or increases) the level or activity of SAMTOR. In certain aspects, an agent or composition increases or decreases expression of SAMTOR, thereby modulating the level or activity of mTORC1.

In some embodiments, the identification of an agent or test compound is performed utilizing isolated proteins (e.g., outside a cell). Agents or test compounds may be identified using any biophysical assay known to those of skill in the art, including, but not limited to, Isothermal Titration calorimetry (ITC), Surface Plasmon Resonance (SPR), Thermal Stability Analysis (TSA), thermal shift, or crystallography. In alternative embodiments, the identification of an agent is performed using cell-based assays. In some aspects, the agent is incubated with cells expressing the first polypeptide and the second polypeptide or protein complex.

In some embodiments, an agent (e.g., a therapeutic agent) is an antibody that binds to SAMTOR. The antibody may inhibit the ability of SAMTOR to bind SAM, thereby inhibiting mTORC1. Alternatively, the antibody may inhibit the ability of SAMTOR to bind GATOR1-KICSTOR, thereby activating mTORC1.

In certain embodiments, peptides, polypeptides, proteins (e.g., fusion proteins), and homologs thereof, are useful as competitive inhibitors for the binding of SAMTOR to GATOR1-KICSTOR. The peptides and polypeptides correspond to a portion of SAMTOR, or have at least 70%, at least 75%, at least 80%, at least 85%, at least 90%, or at least 95% homology at the amino acid level to a portion of the SAMTOR amino acid sequence. The proteins comprise a peptide or polypeptide that corresponds to a portion of SAMTOR, or has at least 70%, at least 75%, at least 80%, at least 85%, at least 90%, or at least 95% homology at the amino acid level to a portion of the SAMTOR amino acid sequence. In other embodiments, peptides, polypeptides, proteins, and homologs thereof are useful in assays to identify modulators of SAMTOR. Such modulators may alter the affinity of SAMTOR for one or more metabolites, e.g., SAM, or alter the interaction between SAMTOR and GATOR1-KICSTOR.

In still another embodiment, the invention provides one or more oligonucleotides, e.g., a siRNA, shRNA or antisense oligonucleotide that is complementary to and specifically hybridizes to DNA or mRNA encoding SAMTOR. In some aspects, oligonucleotides of this invention are capable of decreasing the transcription and/or translation of the corresponding protein. Oligonucleotides as described herein may be single-stranded or multi-stranded (e.g., double-stranded).

In still other embodiments, the invention provides methods of modifying SAMTOR using a genome editing system known in the art, such as CRISPR/Cas or TALENS. The system may be used to decrease the ability of SAMTOR to bind SAM or to decrease SAMTOR expression. In some aspects, the invention provides a method of downregulating SAM using such a system.

In some embodiments, the invention provides a method of identifying a test compound as an activator of mTORC1 activity comprising the steps of:
a) providing a mixture comprising:
 (i) a first polypeptide comprising a GATOR1-KICSTOR-binding fragment of a SAMTOR, or a polypeptide having at least 80% homology to a fragment of SAMTOR that retains the ability to bind GATOR1-KICSTOR;
 (ii) a second polypeptide or protein complex comprising a SAMTOR-binding fragment of a GATOR1-KICSTOR complex, or a polypeptide or protein complex having at least 80% homology to a fragment of GATOR1-KICSTOR complex that retains the ability to bind to a SAMTOR; and
 (iii) a test compound,
under conditions that allow the first polypeptide to associate with the second polypeptide or protein complex (e.g., in the absence of the test compound);
b) determining whether the amount of the first polypeptide associated with the second polypeptide or protein complex is altered in the presence of the test compound as compared to either the absence of the test compound or the presence of a negative control, wherein if the amount of association is decreased the test compound is identified as an activator of mTORC1 activity.

In some embodiments, a polypeptide comprising a GATOR1-KICSTOR-binding fragment of a SAMTOR, or a polypeptide having at least 80% homology to a fragment of SAMTOR that retains the ability to bind GATOR1-KICSTOR further retains the ability to bind SAM.

In various embodiments, the mixture may be prepared by combining the first polypeptide or protein complex, the second polypeptide or protein complex, and/or the test compound in any order.

In some embodiments, the method further comprises pre-incubating a first polypeptide with a second polypeptide or protein complex prior to step (a). The pre-incubation of the first polypeptide with the second polypeptide or protein complex may occur under conditions that permit association of the first polypeptide with the second polypeptide or protein complex, e.g., in a solution substantially free of SAM. The pre-incubation of the first polypeptide with the second polypeptide or protein complex results in a pre-incubation complex (e.g., a SAMTOR-GATOR1-KICSTOR complex). In some aspects, the pre-incubation complex is purified. Purification may occur by immunopurification, gel filtration, or by other purification methods known to those of skill in the art.

In other embodiments, the method further comprises pre-incubating a first polypeptide with a test compound prior to step (a). In still other embodiments, the method further comprises pre-incubating a second polypeptide or protein complex with a test compound prior to step (a). In some embodiments, the methods further comprise pre-incubating the test compound with SAM prior to step (a).

In some embodiments a pre-incubation step described herein (e.g., pre-incubation of a first polypeptide with a second polypeptide or protein complex, pre-incubation of a first polypeptide with a test compound, pre-incubation of a second polypeptide or protein complex with a test compound, or pre-incubation of a test compound with SAM) occurs for a period of between about 5 minutes and 48 hours, e.g., about 5 minutes to 120 minutes, 10 minutes to 90 minutes, 15 minutes to 60 minutes, or 20 minutes to 45 minutes. The pre-incubation step may occur for about 25 minutes. In some aspects, the pre-incubation step occurs for a period of between 1 hour and 24 hours, e.g., about 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, or 24 hours. The pre-incubation step may occur for a period of less than 48 hours, less than 36 hours, less than 24 hours, less than 12 hours, or less than 6 hours.

In some embodiments, the first polypeptide comprises a GATOR1-KICSTOR-binding fragment of SAMTOR, or a polypeptide having at least 80% homology to the fragment of SAMTOR that retains the ability to bind GATOR1-KICSTOR. In some embodiments, the first polypeptide used in the method comprises a GATOR1-KICSTOR-binding fragment of SAMTOR, or an isoform thereof. In some aspects, a polypeptide includes protein complexes, such as homodimers, heterodimers, and hetero-oligomers.

In certain embodiments, the first polypeptide comprises an amino acid sequence that is at least 80%, 85%, 86%, 87%, 88%, 89%, 90%, 91%, 92%, 93%, 94%, 95%, 96%, 97%, 98%, or 99% identical to a GATOR1-KICSTOR-binding fragment of SAMTOR over at least 20%, 30%, 40%, 50%, 60%, 70%, 80%, 90%, 95%, 96%, 97%, 98%, 99%, or 100% of the GATOR1-KICSTOR-binding fragment of SAMTOR and retains the ability to bind GATOR1-KICSTOR.

In certain embodiments, the second polypeptide or protein complex comprises an amino acid sequence that is at least 80%, 85%, 86%, 87%, 88%, 89%, 90%, 91%, 92%, 93%, 94%, 95%, 96%, 97%, 98%, or 99% to a SAMTOR-binding fragment of a GATOR1-KICSTOR complex over at least 20%, 30%, 40%, 50%, 60%, 70%, 80%, 90%, 95%, 96%, 97%, 98%, 99%, or 100% of the SAMTOR-binding fragment of the GATOR1-KICSTOR complex and retains the ability to bind to SAMTOR. The homology percent and length of the amino acid sequence may apply to each individual protein of the GATOR1-KICSTOR complex. In some aspects, GATOR1 and KICSTOR are provided as distinct proteins instead of as a complex, and the homology percent and length of the amino acid sequence applies to each individual protein.

The second polypeptide or protein complex may comprise a SAMTOR-binding fragment of a GATOR1-KICSTOR complex, or a polypeptide or protein complex having at least 80% homology to the fragment of the GATOR1-KICSTOR complex that retains the ability to bind to SAMTOR. In some embodiments, the second polypeptide or protein complex comprises a SAMTOR-binding fragment of a GATOR1-KICSTOR complex. In some embodiments, the SAMTOR-binding fragment of a GATOR1-KICSTOR complex comprises at least one GATOR1 component or fragment thereof and at least one KICSTOR component or fragment thereof. In other embodiments, the SAMTOR-binding fragment of a GATOR1-KICSTOR complex comprises two or more GATOR1 components or fragments thereof. In still other embodiments, the SAMTOR-binding fragment of a GATOR1-KICSTOR complex comprises two or more KICSTOR components.

In one aspect, the second polypeptide or protein complex comprises a SAMTOR-binding fragment of at least one of Depdc5, Nprl3, and Nprl2 and/or at least one of Kaptin, ITFG2, C12orf66, and SZT2. In another aspect, the second polypeptide or protein complex comprises a SAMTOR-binding fragment of at least one of Depdc5, Nprl3, and Nprl2. In still another aspect, the second polypeptide or protein complex comprises a SAMTOR-binding fragment of at least one of Kaptin, ITFG2, C12orf66, and SZT2. In a more specific aspect of these embodiments, the second polypeptide or protein complex comprises a SAMTOR-binding fragment of Depdc5. In a more specific aspect of these embodiments, the second polypeptide or protein complex comprises a SAMTOR-binding fragment of Nprl3. In a more specific aspect of these embodiments, the second polypeptide or protein complex comprises a SAMTOR-binding fragment of Nprl2. In a more specific aspect of these embodiments, the second polypeptide or protein complex comprises a SAMTOR-binding fragment of Kaptin. In a more specific aspect of these embodiments, the second polypeptide or protein complex comprises a SAMTOR-binding fragment of ITFG2. In a more specific aspect of these embodiments, the second polypeptide or protein complex comprises a SAMTOR-binding fragment of C12orf66. In a more specific aspect of these embodiments, the second polypeptide or protein complex comprises a SAMTOR-binding fragment of SZT2.

The determination of whether the amount of the first polypeptide associated with the second polypeptide or protein complex is altered in the presence of the test compound is typically achieved by distinguishing between the first polypeptides associated with the second polypeptides or protein complexes and the first polypeptides that are not associated with the second polypeptides or protein complexes. One way of achieving such differentiation is by binding a tag to at least one of the first or second polypeptide (e.g., a first tag binds to a first polypeptide and/or a second tag binds to a second polypeptide) or protein complex and then detecting at least one of the bound tags or a product of the first and second tags. Other ways of achieving such differentiation includes, but is not limited to, separation techniques, such as gel filtration (size exclusion chromatography; non-denaturing gel electrophoresis) and differential centrifugation; and size determination, such as mass spectrometry.

The term "tag" as used herein includes, but is not limited to, detectable labels, such as fluorophores, radioisotopes, colorimetric substrates, or enzymes; heterologous epitopes for which specific antibodies are commercially available, e.g., FLAG-tag; heterologous amino acid sequences that are ligands for commercially available binding proteins, e.g., Strep-tag, biotin; fluorescence quenchers typically used in conjunction with a fluorescent tag on the other polypeptide; and complementary bioluminescent or fluorescent polypeptide fragments. A tag that is a detectable label or a complementary bioluminescent or fluorescent polypeptide fragment may be measured directly (e.g., by measuring fluorescence or radioactivity of, or incubating with an appropriate substrate or enzyme to produce a spectrophotometrically detectable color change for the associated polypeptides as compared to the unassociated polypeptides). A tag that is a heterologous epitope or ligand is typically detected with a second component that binds thereto, e.g., an antibody or binding protein, wherein the second component is associated with a detectable label. A tag, e.g., a heterologous epitope, may also be used to affix or immobilize the polypeptide to which it is bound to a solid support.

As used herein, the term "immobilize" in the context of an immobilized polypeptide or protein complex, refers to a substance that is affixed (e.g., tethered) to a substrate or support (e.g., a solid support), and not free in solution.

The term "solid support" is defined as a solid material of any size, shape, composition or construction that is suitable as an attachment material for any polypeptide or protein complex utilized in the present invention.

Thus, in certain embodiments of the methods described above: the first polypeptide is optionally bound to a first tag; the second polypeptide or protein complex is optionally bound to a second tag; at least one of the first polypeptide or the second polypeptide or protein complex is bound to its corresponding tag; and determining the amount of the first polypeptide associated with the second polypeptide or protein complex: (a) comprises detecting at least one of the first or second tag or a product of the first and second tag; and (b) distinguishes between the first polypeptide associated with the second polypeptide or protein complex and the first polypeptide not associated with the second polypeptide or protein complex.

In certain aspects of the embodiment in which at least one of the first polypeptide or the second polypeptide or protein complex is bound to its corresponding tag: the first tag is present and comprises a first epitope not naturally present in SAMTOR; the second tag is present and comprises a second epitope not naturally present in any GATOR1-KICSTOR complex; detecting the first tag comprises binding a first antibody specific for the first epitope; and detecting the second tag comprises binding a second antibody specific for the second epitope. For the sake of clarity in these aspects, although both the first and the second tags are present, it is not required that both tags be detected, nor that both the first and second antibody be used for detection. Some of the assays that fall under these aspects use only one antibody and detect only one tag. The other tag may be used to affix or immobilize the polypeptide to which it is bound to a solid support.

In other aspects of the embodiment in which at least one of the first polypeptide or the second polypeptide or protein complex is bound to its corresponding tag one of the first polypeptide or second polypeptide or protein complex is immobilized on a solid support. In a more specific aspect, the immobilization on the solid support is mediated through the corresponding tag. In one example, the solid support is a bead or plate coated with an antibody that recognizes the tag, resulting in the tethering of the tagged polypeptide or protein complex to the bead or plate.

In still another aspect of the embodiment in which at least one of the first polypeptide or the second polypeptide or protein complex is bound to its corresponding tag, only one of the first antibody or the second antibody is used for detection of the first or second tag, and the antibody used for detection is conjugated to a detectable label.

In yet another aspect, both the first and second tags are present and are each members of a proximity fluorescence reagent pair. The term "proximity fluorescence reagent pair" refers to two reagents that react with one another to produce detectable fluorescence or phosphorescence when they are in close proximity, e.g., when the two polypeptides to which they are attached are associated with one another. Examples of proximity fluorescence reagent pair that may be utilized in this aspect are donor-acceptor FRET pairs that are well-known in the art and commercially available (e.g., cyan fluorescent protein/yellow fluorescent protein; luciferase/yellow fluorescent protein; blue fluorescent protein/green fluorescent protein 2; dansyl/FITC; Cy3/Cy5; and carboxyfluorescein succinimidyl ester/Texas Red); and bimolecular fluorescence complementation (BiFC) pairs.

In a related aspect, both the first and the second tags are present; the first and second antibodies are both utilized to detect the association of the first polypeptide and the second polypeptide or protein complex; and the first and second antibodies are each conjugated to a different member of a proximity fluorescence reagent pair.

In still another aspect, only one of the first tag or second tag is present; the tag present is a fluorescent moiety bound to the N- or C-terminus of the first polypeptide or the second polypeptide; and detecting the association of the first polypeptide with the second polypeptide or protein complex comprises solution phase fluorescence polarization. In a more specific aspect the tag is 5-carboxyfluorescein attached to the N- or C-terminus of the first or second polypeptide.

In yet another aspect, one of the first polypeptide or second polypeptide or protein complex is immobilized on a solid support; and detecting the association of the first polypeptide with the second polypeptide or protein complex comprises surface plasmon resonance (SPR). The immobilization can occur through direct amine coupling of the protein or through the addition of an avidity-tag such as biotin and tethering the tagged protein to a streptavidin coated matrix.

In other embodiments, the invention provides a method of identifying a test compound as an inhibitor of mTORC1 activity comprising the steps of:
  a) providing a mixture comprising:
    (i) a first polypeptide comprising a GATOR1-KICSTOR-binding fragment of a SAMTOR, or a polypeptide having at least 80% homology to a fragment of SAMTOR that retains the ability to bind GATOR1-KICSTOR;
    (ii) a second polypeptide or protein complex comprising a SAMTOR-binding fragment of a GATOR1-KICSTOR complex, or a polypeptide or protein complex having at least 80% homology to a fragment of GATOR1-KICSTOR complex that retains the ability to bind to a SAMTOR; and
    (iii) a test compound,
  b) determining whether the amount of the first polypeptide associated with the second polypeptide or protein complex is altered in the presence of the test compound as compared to either the absence of the test compound or the presence of a negative control, wherein if the amount of association is increased the test compound is identified as an inhibitor of mTORC1 activity.

In some embodiments, the method further comprises pre-incubating a first polypeptide with a second polypeptide prior to step (a). In other embodiments, the method further comprises pre-incubating a first polypeptide with a test compound prior to step (a). In still other embodiments, the method further comprises pre-incubating a second polypeptide with a test compound prior to step (a). In some embodiments, the methods further comprise pre-incubating the test compound with SAM prior to step (a).

In certain aspects, steps (a) and (b) occur under conditions that prevent the first polypeptide from associating with the second polypeptide or protein complex (e.g., in the absence of the test compound). Such conditions typically include the presence of SAM, but may also include the presence of other agents that prevent such association. These other agents may be identified in the assays described herein. In one aspect, the assays for identifying inhibitors of association are done in the presence of SAM.

In certain embodiments, the first polypeptide comprises a GATOR1-KICSTOR-binding fragment of SAMTOR, or a polypeptide having at least 80% homology to the fragment of SAMTOR that retains the ability to bind GATOR1-KICSTOR. In some embodiments, a second polypeptide or protein complex comprising a SAMTOR-binding fragment of a GATOR1-KICSTOR complex, or a polypeptide or protein complex having at least 80% homology to the fragment of a GATOR1-KICSTOR complex that retains the ability to bind to SAMTOR.

Each of the specific embodiments and aspects set forth above for the method of identifying a test compound as an activator of mTORC1 are also applicable to the method of identifying a test compound as an inhibitor of mTORC1.

In other embodiments, the invention provides a method of identifying a test compound as a modulator of mTORC1 activity. In one aspect of these embodiments, the method comprises the steps of:
a. providing a mixture comprising:
  i. a first polypeptide comprising a GATOR1-KICSTOR-binding fragment of SAMTOR, or a polypeptide having at least 80% homology to a fragment of SAMTOR that retains the ability to bind GATOR1-KICSTOR;
  ii. a second polypeptide or protein complex comprising a SAMTOR-binding fragment of a GATOR1-KICSTOR complex, or a polypeptide or protein complex having at least 80% homology to a fragment of GATOR1-KICSOR complex that retains the ability to bind to SAMTOR; and
  iii. a test compound; and
b. determining whether the amount of the first polypeptide associated with the second polypeptide or protein complex is altered in the presence of the test compound as compared to either the absence of the test compound or the presence of a negative control, wherein if the amount of association is decreased the test compound is identified as an activator of mTORC1 activity, and wherein if the amount of association is increased the test compound is identified as an inhibitor of mTORC1 activity.

In some embodiments, the recited methods are carried out in solutions lacking SAM and/or other compounds known to disrupt the association of SAMTOR and GATOR1-KICSTOR. In other embodiments, the recited methods are carried out in solutions having various concentrations of SAM and/or other compounds known to disrupt the association of SAMTOR and GATOR1-KICSTOR. In various embodiments, the GATOR1-KICSTOR-SAMTOR complex is allowed to form before adding the test compound. In other embodiments, the GATOR1-KICSTOR-SAMTOR complex does not form before adding the test compound.

In other embodiments, the invention provides a method of identifying a test compound as a modulator of mTORC1 by determining if the test compound can decrease or increase the affinity of SAMTOR for SAM. In one aspect of these embodiments, the method comprises the steps of:
a. providing a mixture comprising:
  i. a SAMTOR polypeptide, or a polypeptide having at least 80% homology to SAMTOR that retains the ability to bind SAM;
  ii. SAM;
  iii. a test compound,
under conditions that allow SAM to bind to the polypeptide; and
b. determining whether the amount of SAM bound to the polypeptide is altered in the presence of the test compound as compared to either the absence of the test compound or the presence of a negative control, wherein if the amount of binding is decreased in the presence of test compound, the test compound is identified as an inhibitor of mTORC1 activity; and if the amount of binding is increased in the presence of the test compound, the test compound is identified as an activator of mTORC1 activity.

In some embodiments, the mixture of step (a) is further incubated with a GATOR1-KICSTOR complex. The ability of SAMTOR to associate with the GATOR1-KICSTOR complex may then be determined.

The determination of whether the amount of SAM bound to the polypeptide is altered in the presence of the test compound may further include determining that the test compound is not competing with SAM for binding to SAMTOR and acting as a SAM mimetic.

In some aspects, the term "mimetic" as used herein refers to an agent that either emulates the biological effects of SAM on mTORC1 activation in a cell, as measured by mTORC1 phosphorylation of an mTORC1 substrate (e.g., S6K) in response to the agent, or that increases, directly or indirectly, the level of SAM in a cell. In certain aspects of these embodiments, the modulator is not a peptide or peptide analog having at least 10% SAM content. In certain aspects, the modulator is not a peptide or peptide analog having at least 10% methionine content. Modulators of SAMTOR, may be identified by screening commercially available small molecule and natural product libraries and may be further optimized for SAMTOR modulating activity by well-known medicinal chemistry manipulations and modifications.

In certain aspects of the above embodiments, the SAM utilized for determining if the test compound can modulate the affinity of SAMTOR for SAM is tagged with a detectable label. In one aspect of these embodiments, the SAM is tagged with a radiolabel, such as $^3$H. In another aspect of these embodiments, the method additionally comprises the step of separating polypeptide-bound tagged SAM from free tagged SAM prior to determining the amount of SAM bound to the polypeptide. This may be achieved by method well known in the art, including the immobilization of any polypeptide-SAM complexes to a solid support via an immobilized antibody specific to the polypeptide. Once the separation of bound and free SAM has been achieved, radioactivity of the bound portion can be measured and compared to polypeptide-bound SAM in the absence of test compound or the presence of a negative control compound. These methods may also be used to determine whether the test compound is or is not a SAM mimetic.

In other embodiments, the invention provides a method of identifying a test compound as a disrupter or a stabilizer (e.g., in the presence of SAM) of a SAMTOR-GATOR1-KICSTOR complex. In one aspect of these embodiments, the method comprises the steps of providing a mixture comprising a SAMTOR-GATOR1-KICSTOR complex and a test compound; and determining whether the stability of the SAMTOR-GATOR1-KICSTOR complex is altered in the presence of the test compound as compared to either the absence of the test compound or the presence of a negative control, wherein if the amount of the SAMTOR-GATOR1-KICSTOR complex is decreased the test compound is identified as a disrupter of the SAMTOR-GATOR1-KICSTOR complex, and if the amount of the SAMTOR-GATOR1-KICSTOR complex is increased the test compound is identified as a stabilizer of the SAMTOR-GATOR1-KICSTOR complex.

In some aspects, the SAMTOR-GATOR1-KICSTOR complex is formed by combining a first polypeptide comprising a GATOR1-KICSTOR-binding fragment of SAMTOR, or a polypeptide having at least 80% homology to a fragment of SAMTOR that retains the ability to bind GATOR1-KICSTOR, and a second polypeptide or protein complex comprising a SAMTOR-binding fragment of a GATOR1-KICSTOR complex, or a polypeptide or protein complex having at least 80% homology to a fragment of GATOR1-KICSTOR complex that retains the ability to bind to SAMTOR. The complex may be purified prior to mixing the complex with a test compound.

In some aspects, SAM is added to the mixture at the same time as the SAMTOR-GATOR1-KICSTOR complex and the test compound. Alternatively, SAM is added to the mixture after the mixture is pre-incubated as described herein (e.g., for a pre-determined period of time). The methods for identifying a test compound as a stabilizer of the SAMTOR-GATOR1-KICSTOR complex may be applied to a mixture comprising the SAMTOR-GATOR1-KICSTOR complex, a test compound, and SAM.

The invention described herein provides method of decreasing and methods of increasing mTORC1 activity in a cell. In some embodiments, a cell in a composition or method described herein is a mammalian cell, e.g., a human, non-human primate, canine, feline, murine, bovine, equine, or porcine cell. In some embodiments, a cell in a composition or method described herein is a normal, healthy cell. In some embodiments, a cell in a composition or method described herein is a diseased cell. In some embodiments, a cell in a composition or method described herein is derived from a subject suffering from a disease, condition or disorder that would benefit from inhibiting or decreasing mTORC1 activity. In some embodiments, a cell in a composition or method described herein is derived from a subject suffering from a disease, condition or disorder that would benefit from increasing mTORC1 activity.

In still other embodiments, the invention provides a method of agonizing mTORC1 activity in a cell by contacting the cell with an agent that inhibits or reduces the interaction of SAMTOR with a GATOR1-KICSTOR complex. The method of agonizing mTORC1 activity may include maintaining or continuing mTORC1 activity levels or increasing mTORC1 activity levels as compared to a control state (e.g., measured mTORC1 activity levels when SAMTOR interacts with the GATOR1-KICSTOR complex).

In still other embodiments, the invention provides a method of agonizing mTORC1 activity in a cell by contacting the cell with an agent that increases the binding of SAM by SAMTOR.

In other embodiments, the invention provides a method of treating a disease, condition or disorder in a subject which would benefit by activating mTORC1 activity in a subject comprising the step of administering to the subject an agent that reduces or antagonizes the interaction of a SAMTOR with the GATOR1-KICSTOR complex. In related embodiments, the invention provides a method of treating a disease, condition or disorder in a subject which would benefit by activating mTORC1 activity in a subject comprising the step of administering to the subject an agent that increases the binding of SAM by SAMTOR. In one aspect of either of these embodiments, the disease, condition or disorder is selected from those resulting in skeletal muscle atrophy (such as sarcopenia, muscle denervation, prolonged immobilization and muscular dystrophy), decreased satiety (e.g., cachexia and anorexia), ribosomopathies (e.g. Diamond-Blackfan anemia, 5q-syndrome, Shwachman-Diamond syndrome, X-linked dyskeratosis, cartilage hair hypoplasia, and Treacher Collins syndrome) and cohesinopathies (e.g. Roberts syndrome and Cornelia de Lange syndrome).

Agents that are useful in the above-described methods of increasing mTORC1 activation include test compounds identified by the mTORC1 activator identification assays set forth herein. Such useful agents may be formulated with one or more pharmaceutically acceptable carriers and/or excipients. In some embodiments, the agent is other than SAM. In some embodiments, the agent is other than a naturally occurring metabolite. In some embodiments, the agent is other than an metabolite.

In still other embodiments, the invention provides a method of inhibiting or decreasing mTORC1 activity in a cell by contacting the cell with an agent that induces or increases the interaction of SAMTOR with a GATOR1-KICSTOR complex, or that prevents the dissociation of SAMTOR with GATOR1-KICSTOR in the presence of SAM.

In still other embodiments, the invention provides a method of inhibiting or decreasing mTORC1 activity in a cell by contacting the cell with an agent that decreases the binding of SAM by SAMTOR. Methods of inhibiting or decreasing mTORC1 activity in a cell may alternatively comprise contacting the cell with an agent that increases expression of SAMTOR.

In other embodiments, the invention provides a method of treating a disease, condition or disorder in a subject which would benefit by inhibiting or decreasing mTORC1 activity in a subject comprising the step of administering to the subject an agent that induces or increases the interaction of SAMTOR with the GATOR1-KICSTOR complex, or that prevents the dissociation of SAMTOR with GATOR1-KICSTOR in the presence of SAM. In other related embodiments, the invention provides a method of treating a disease, condition or disorder in a subject which would benefit by inhibiting or decreasing mTORC1 activity in a subject comprising the step of administering to the subject an agent that decreases the binding of SAM by SAMTOR. In one aspect of either of these embodiments, the disease, condition or disorder is selected from a metabolic disease (e.g., type 2 diabetes, obesity, non-alcoholic steatohepatitis (NASH), and hyperlipidemia), a neurodegenerative disease (e.g., Alzheimer's disease, Parkinson's Disease, Huntington's Disease, and amyotrophic lateral sclerosis), an autoimmune disease (e.g., psoriasis, rheumatoid arthritis, multiple sclerosis, systemic lupus erythematosus, gout, allergic rhinitis, Crohn's Disease, and ulcerative colitis), rare and mitochondrial disease (e.g., Leigh's Syndrome, Friedreich's Ataxia Cardiomyopathy, Leber's Hereditary Optic Neuropathy, lymphangioleiomyomatosis, tuberous sclerosis, Pompe Disease (Glycogen storage disease II), and lysosomal storage diseases), cardiovascular disease (e.g., cardiomyopathy, heart failure, ischemic heart disease (atherosclerotic disease), ischemic stroke, and pulmonary arterial hypertension), renal disease (e.g., diabetic nephropathy, polycystic kidney disease, and acute kidney injury), neuropsychiatric disease (e.g., epilepsy, autism spectrum disorder, and depressive disorder), oncological disease (e.g., renal cell carcinoma, solid tumors, hematological cancers), and improving immune response to vaccines and other medically important uses in cases of a suppressed immune system such as age-related immunosenescence and cancer immunotherapy.

Agents that are useful in the above-described methods of decreasing or inhibiting mTORC1 activity include test compounds identified by the mTORC1 inhibitor identification assays set forth herein. Such useful agents may be formulated with one or more pharmaceutically acceptable carriers and/or excipients. Other agents that are useful in the above-described methods of decreasing mTORC1 activation include agents that mimic amino acid starvation and/or glucose starvation. Such agents may be confirmed as increasing SAMTOR-GATOR1-KICSTOR interaction through testing in the mTORC1 inhibitor identification assays of the invention.

In still other embodiments, the invention provides a composition comprising SAMTOR. In some aspects, SAMTOR is formulated with one or more pharmaceutically acceptable carriers and/or excipients. In other embodiments, the invention provides a composition comprising SAM. In some aspects, SAM is formulated with one or more pharmaceutically acceptable carriers and/or excipients. The compositions may be useful for modulating mTORC1 activity. In some aspects, the invention provides a method of inhibiting SAMTOR-GATOR1-KICSTOR interaction by administering SAM (e.g., activate mTORC1).

In other embodiments, the invention provides a composition comprising a polypeptide comprising a GATOR1-KICSTOR-binding fragment of SAMTOR. In still other embodiments, the invention provides a composition comprising a polypeptide having at least 80% homology to a fragment of SAMTOR that retains the ability to bind GATOR1-KICSTOR. In other embodiments, the composition comprises a polypeptide having at least 80% homology to a fragment of SAMTOR that retains the ability to bind SAM. Alternatively, the composition may comprise a polypeptide having at least 80% homology to a fragment of SAMTOR that retains the ability to bind GATOR1-KICSTOR, but fails to bind SAM. In some aspects, the polypeptide is formulated with one or more pharmaceutically acceptable carriers and/or excipients.

In some embodiments, the invention provides a nucleic acid construct that encodes any of the SAMTOR polypeptides or fragments and/or variants thereof. In some embodiments a variant polypeptide comprises or consists of at least one domain of an original polypeptide. In some embodiments a variant polynucleotide hybridizes to an original polynucleotide under stringent conditions for sequences of the length of the original polypeptide. In some embodiments a variant polypeptide or polynucleotide comprises or consists of a polypeptide or polynucleotide that is at least 50%, 60%, 70%, 80%, 90%, 95%, 96%, 97%, 98%, 99%, or more identical in sequence to the original polypeptide or polynucleotide over at least 20%, 30%, 40%, 50%, 60%, 70%, 80%, 90%, 95%, 96%, 97%, 98%, 99%, or 100% of the original polypeptide or polynucleotide.

The SAMTOR polypeptides and/or variants thereof that retain the ability to bind to GATOR1-KICSTOR but not SAM may be useful for modulating mTORC1 activity, e.g., mimicking the effects of methionine starvation even in the presence of normal levels of methionine. Nucleic acids, e.g., stabilized translatable mRNA, may be administered to deliver such polypeptides.

In some aspects, the methods and compositions described herein are administered to any subject of interest, e.g., any mammal. The term "mammal" as used herein includes both humans and non-humans and includes but is not limited to humans, non-human primates, canines, felines, murines, bovines, equines, and porcines. In some aspects the subject is a mouse or rat or monkey or human. In some aspects, the subject is a human subject.

As used herein, pharmaceutical compositions comprise one or more agents or compositions that have therapeutic utility, and a pharmaceutically acceptable carrier, e.g., a carrier that facilitates delivery of agents or compositions. Agents and pharmaceutical compositions disclosed herein may be administered by any suitable means such as orally, intranasally, subcutaneously, intramuscularly, intravenously, intra-arterially, parenterally, intraperitoneally, intrathecally, intratracheally, ocularly, sublingually, vaginally, rectally, dermally, or as an aerosol. Depending upon the type of condition to be treated, compounds of the invention may, for example, be inhaled, ingested or administered by systemic routes. Thus, a variety of administration modes, or routes, are available. The particular mode selected will typically depend on factors such as the particular compound selected, the particular condition being treated and the dosage required for therapeutic efficacy. The methods described herein, generally speaking, may be practiced using any mode of administration that is medically acceptable, meaning any mode that produces acceptable levels of efficacy without causing clinically unacceptable adverse effects.

The term "pharmaceutically acceptable carrier" refers to a carrier for administration of a therapeutic agent. Such carriers include, but are not limited to, saline, buffered saline, dextrose, water, glycerol, ethanol, and combinations thereof and are described in more detail below.

One skilled in the art readily appreciates that the present invention is well adapted to carry out the objects and obtain the ends and advantages mentioned, as well as those inherent therein. The details of the description and the examples herein are representative of certain embodiments, are exemplary, and are not intended as limitations on the scope of the invention. Modifications therein and other uses will occur to those skilled in the art. These modifications are encompassed within the spirit of the invention. It will be readily apparent to a person skilled in the art that varying substitutions and modifications may be made to the invention disclosed herein without departing from the scope and spirit of the invention.

The articles "a" and "an" as used herein in the specification and in the claims, unless clearly indicated to the contrary, should be understood to include the plural referents. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process. Furthermore, it is to be understood that the invention provides all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. It is contemplated that all embodiments described herein are applicable to all different aspects of the invention where appropriate. It is also contemplated that any of the embodiments or aspects can be freely combined with one or more other such embodiments or aspects whenever appropriate. Where elements are presented as lists, e.g., in Markush group or similar format, it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in so many words herein. It should also be understood that any embodiment or aspect of the invention can be explicitly excluded from the claims, regardless of whether the specific exclusion is recited in the specification. For example, any one or more nucleic acids, polypeptides, cells, species or types of organism, disorders, subjects, or combinations thereof, can be excluded.

Where the claims or description relate to a composition of matter, e.g., a nucleic acid, polypeptide, cell, or non-human transgenic animal, it is to be understood that methods of making or using the composition of matter according to any of the methods disclosed herein, and methods of using the composition of matter for any of the purposes disclosed herein are aspects of the invention, unless otherwise indicated or unless it would be evident to one of ordinary skill in the art that a contradiction or inconsistency would arise. Where the claims or description relate to a method, e.g., it is to be understood that methods of making compositions useful for performing the method, and products produced according to the method, are aspects of the invention, unless otherwise indicated or unless it would be evident to one of ordinary skill in the art that a contradiction or inconsistency would arise.

Where ranges are given herein, the invention includes embodiments in which the endpoints are included, embodiments in which both endpoints are excluded, and embodiments in which one endpoint is included and the other is excluded. It should be assumed that both endpoints are included unless indicated otherwise. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise. It is also understood that where a series of numerical values is stated herein, the invention includes embodiments that relate analogously to any intervening value or range defined by any two values in the series, and that the lowest value may be taken as a minimum and the greatest value may be taken as a maximum. Numerical values, as used herein, include values expressed as percentages. For any embodiment of the invention in which a numerical value is prefaced by "about" or "approximately", the invention includes an embodiment in which the exact value is recited. For any embodiment of the invention in which a numerical value is not prefaced by "about" or "approximately", the invention includes an embodiment in which the value is prefaced by "about" or "approximately". "Approximately" or "about" generally includes numbers that fall within a range of 1% or in some embodiments within a range of 5% of a number or in some embodiments within a range of 10% of a number in either direction (greater than or less than the number) unless otherwise stated or otherwise evident from the context (except where such number would impermissibly exceed 100% of a possible value). It should be understood that, unless clearly indicated to the contrary, in any methods claimed herein that include more than one act, the order of the acts of the method is not necessarily limited to the order in which the acts of the method are recited, but the invention includes embodiments in which the order is so limited. It should also be understood that unless otherwise indicated or evident from the context, any product or composition described herein may be considered "isolated".

Specific examples of these methods are set forth below in the Examples.

Examples

SAMTOR Interacts with GATOR1 and KICSTOR

To search for proteins that bind to GATOR1 or KICSTOR, we mined the BioPlex protein-protein interaction database generated by immunoprecipitation followed by mass spectrometry of more than 5000 proteins stably expressed in HEK-293T cells (19). This analysis revealed C7orf60, a previously unstudied protein, as a putative interaction partner of all known components of GATOR1 (Depdc5, Nprl3, Nprl2) and KICSTOR (Kaptin, ITFG2, C12orf66, SZT2). For reasons described herein, we renamed C7orf60 as S-adenosylmethionine sensor upstream of mTORC1 (SAMTOR).

Using an antibody against SAMTOR to probe anti-FLAG immunoprecipitates prepared from cells having endogenously FLAG-tagged components of GATOR1 (Depdc5) or GATOR2 (WDR59) or stably expressing a KICSTOR component (Flag-Kaptin), we validated that SAMTOR co-immunoprecipitates GATOR1 and KICSTOR, but not GATOR2 (FIG. 1A). Moreover, transiently expressed SAMTOR co-immunoprecipitated endogenous GATOR1 and KICSTOR, as detected by the presence of their Nprl3 and SZT2 components, respectively. Loss of a component of GATOR1 or KICSTOR, but not of GATOR2, severely reduced the interaction of SAMTOR with KICSTOR or GATOR1, respectively (FIG. 1B). These data suggest that SAMTOR binds to the supercomplex of GATOR1 and KICSTOR and that both complexes are required for the interaction to occur (FIG. 1C).

Orthologs of SAMTOR are encoded in the genomes of vertebrates and some invertebrates, such as *Drosophila melanogaster*. We could not identify SAMTOR orthologs in *Caenorhabditis elegans* or *Saccharomyces cerevisiae* (FIG. 1D).

SAMTOR Inhibits mTORC1 Signaling and Acts Upstream of the Rag GTPases, GATOR1, and KICSTOR To determine whether SAMTOR regulates mTORC1 signaling, we overexpressed SAMTOR in HEK-293T cells and monitored the phosphorylation of S6 Kinase 1 (S6K1), a canonical mTORC1 substrate. SAMTOR expression suppressed mTORC1 signaling in a dose-dependent fashion (FIG. 2A), establishing SAMTOR as a negative regulator of the pathway. Amino acids activate mTORC1 by promoting its localization to the lysosomal surface (4, 8). Consistent with SAMTOR inhibiting the amino acid sensing pathway upstream of mTORC1, overexpression of GFP-tagged SAMTOR displaced mTOR from lysosomes to an extent similar to that of GFP-Sestrin2, an inhibitor of GATOR2 (20, 21) (FIG. 2B).

To understand where in the mTORC1 pathway SAMTOR functions, we performed epistasis experiments with established mTORC1 regulators. Overexpression of SAMTOR inhibited mTORC1 signaling when co-expressed with the wild type RagA and RagC heterodimer, but not with the constitutively active mutant one (RagA Q66L and RagC S75N) that bypasses the requirement for amino acids for maintaining mTORC1 active (FIG. 2C) (4, 5). In addition, SAMTOR did not inhibit mTORC1 signaling in cells lacking either a GATOR1 or KICSTOR component. Thus, SAMTOR acts upstream of the Rag GTPases and requires GATOR1 and KICSTOR to inhibit mTORC1 signaling (FIG. 2D). In combination with the interaction data, these results are consistent with SAMTOR promoting the function of GATOR1 and/or KICSTOR, which are both negative regulators of mTORC1 signaling.

Figure 3A:
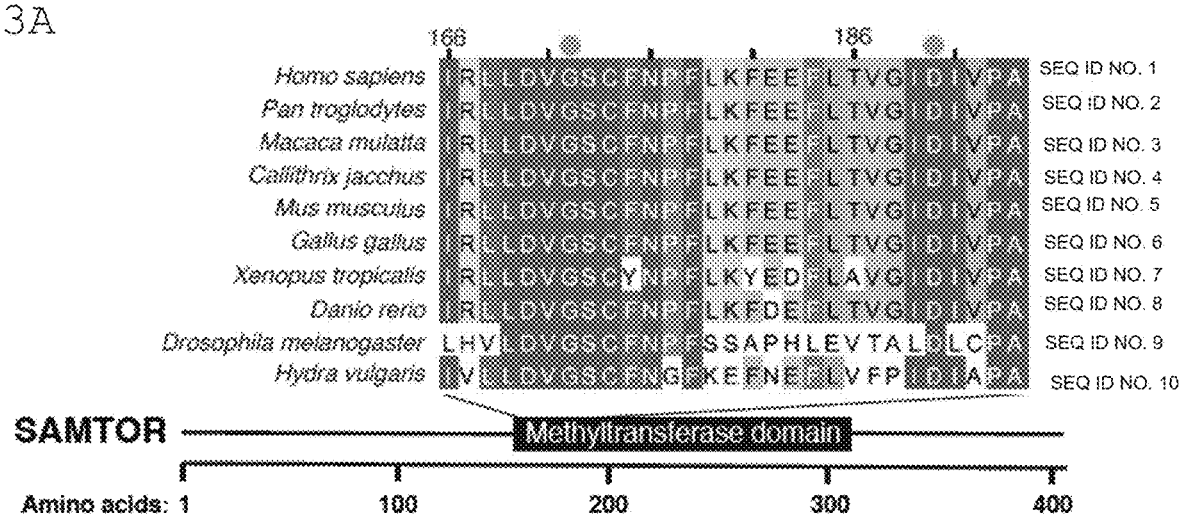
FIGS. 3A-3G depict S-adenosylmethionine binds SAMTOR to disrupt its interaction with GATOR1 and KICSTOR.
Figure 3B:
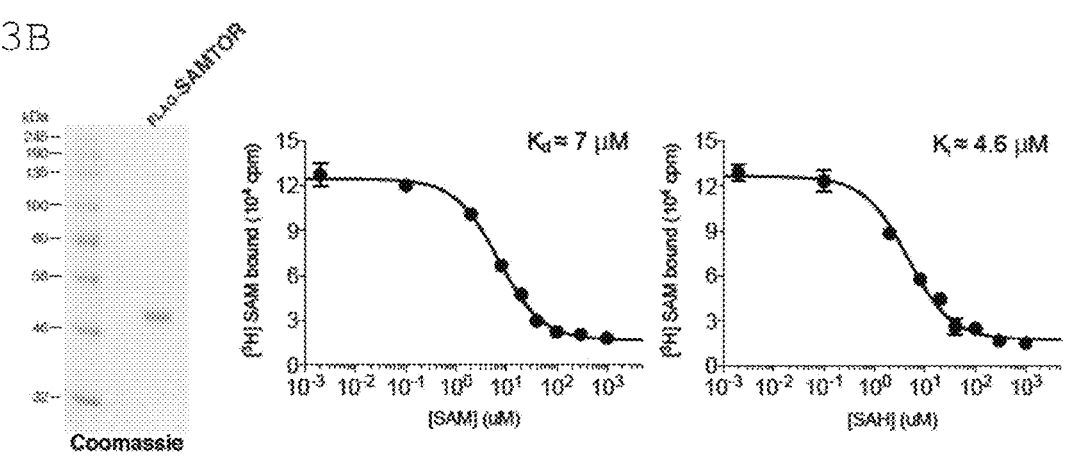

S-Adenosylmethionine Binds SAMTOR and Disrupts its Interaction with GATOR1 and KICSTOR Sequence analyses predict that SAMTOR contains a class I Rossmann fold methyltransferase domain (PF13489) (FIG. 3A and FIGS. 5A-5B) (22). These domains are known to bind S-adenosylmethionine (SAM) and exist in methyltransferases in bacteria, archaea, and eukarya (23). In order to determine if SAMTOR binds SAM, we developed an equilibrium binding assay based on one we used to detect the binding of leucine to Sestrin2 (15) and determined that SAMTOR binds SAM with a dissociation constant of approximately 7 µM (FIG. 3B). A competition binding assay revealed that, as with other SAM-binding proteins, SAMTOR can also bind S-adenosylhomocysteine (SAH), the demethylated form of SAM (FIG. 3B).

Figure 3C:
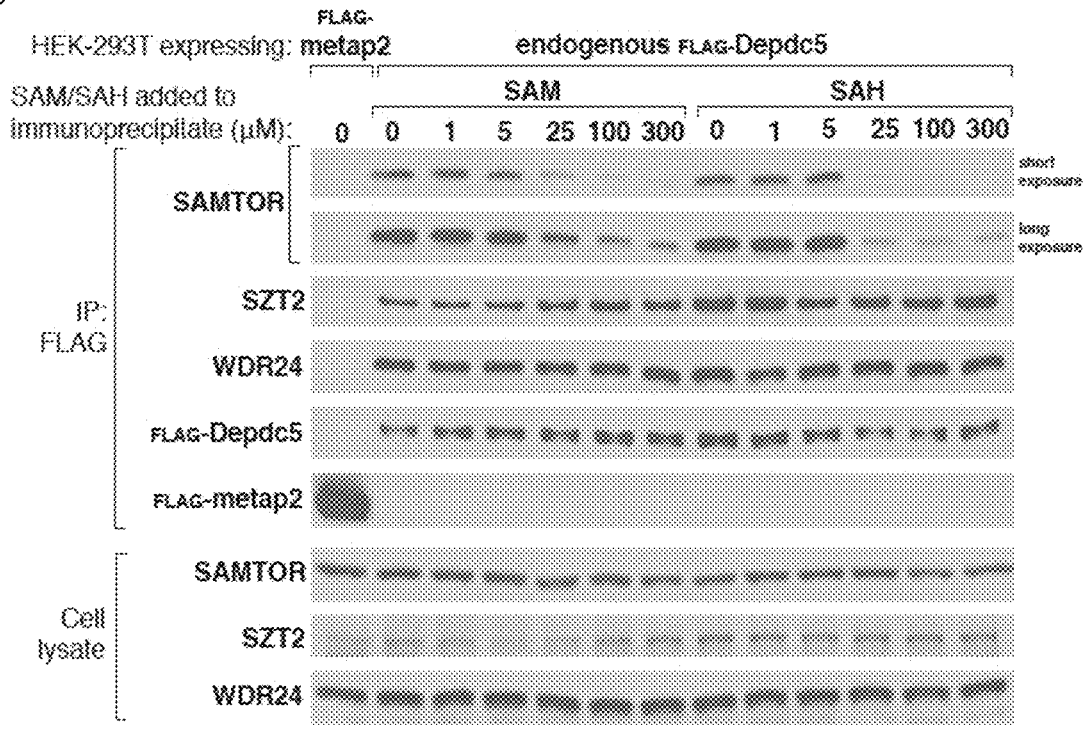
Figure 3D:
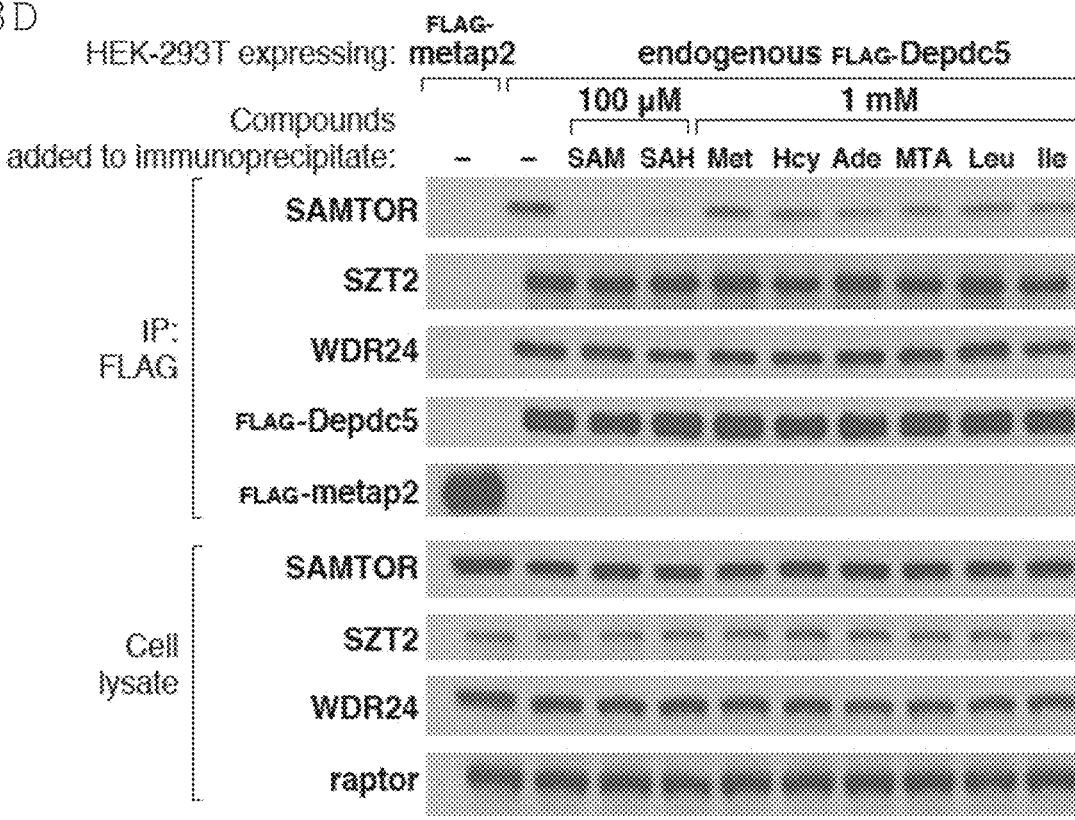

Given these findings, we asked if SAM and SAH regulate the interaction of SAMTOR with GATOR1-KICSTOR. Indeed, SAM and SAH, but not methionine, homocysteine, adenosine, 5-methylthioadenosine, leucine, or isoleucine, disrupted the interaction when added directly to the immunopurified complex kept at 4° C. (FIGS. 3C and 3D). Thus, SAM disrupts the interaction between SAMTOR and GATOR1-KICSTOR analogously to how leucine and arginine induce the release of Sestrin2 and CASTOR1 from GATOR2, respectively (15, 18). Given that SAH has the same effect, it is unlikely that a methylation event is required for SAM to dissociate GATOR1-KICSTOR.

Figure 3E:
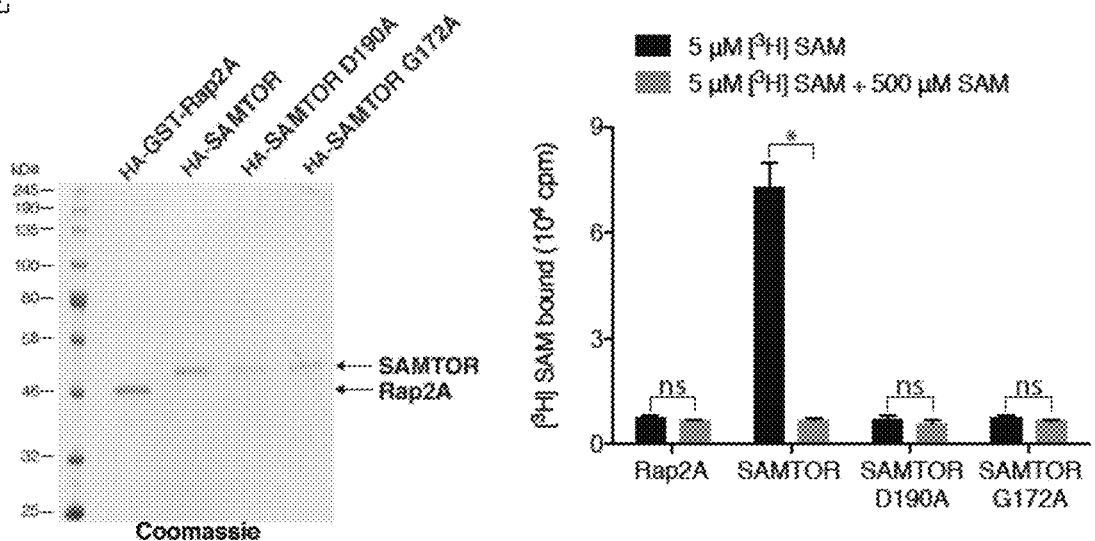
Figure 3F:
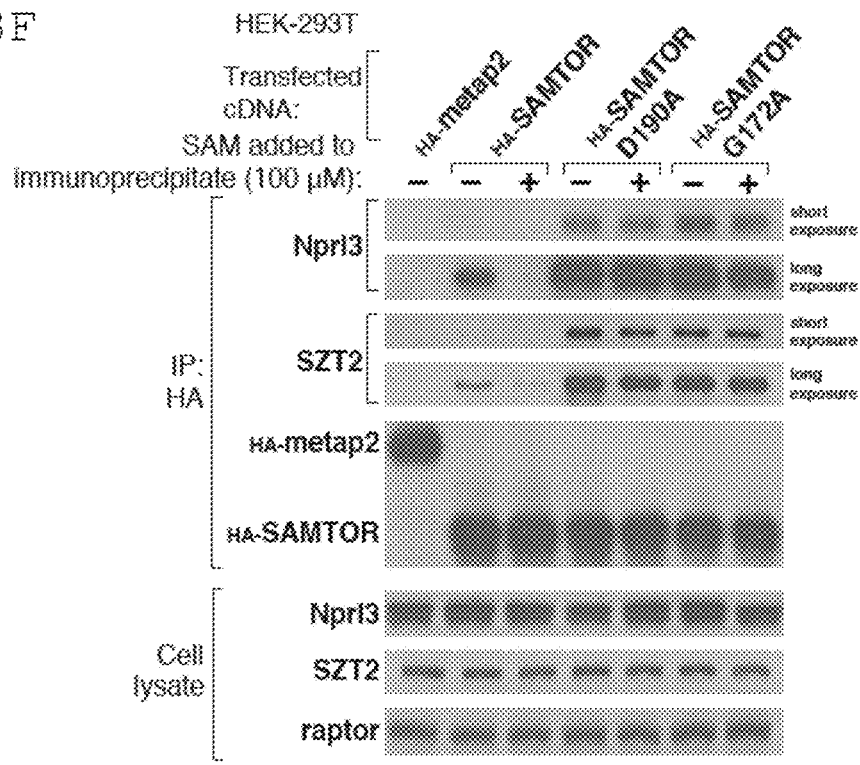
Figure 3G:
Figure 5A:
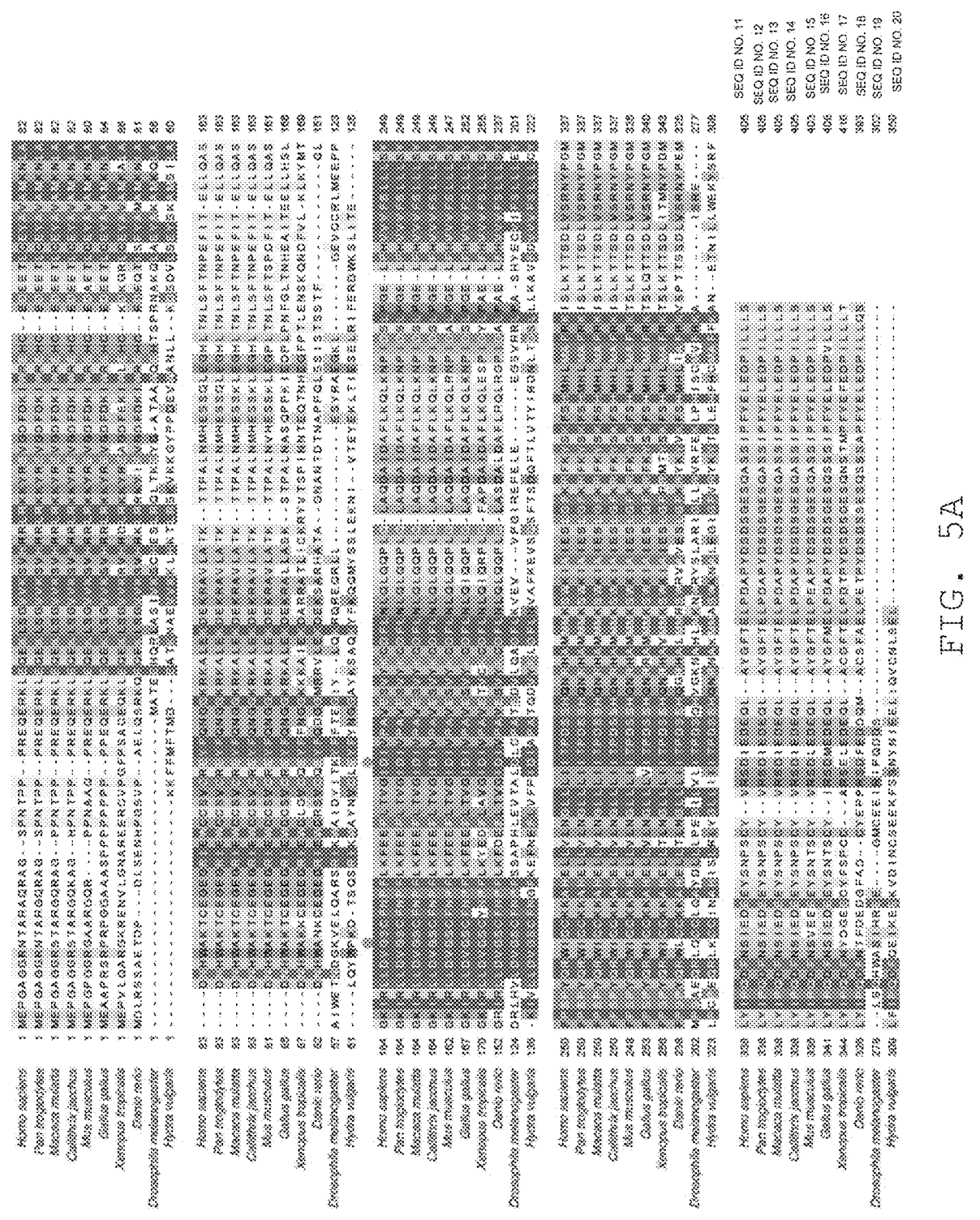
Figure 5B:
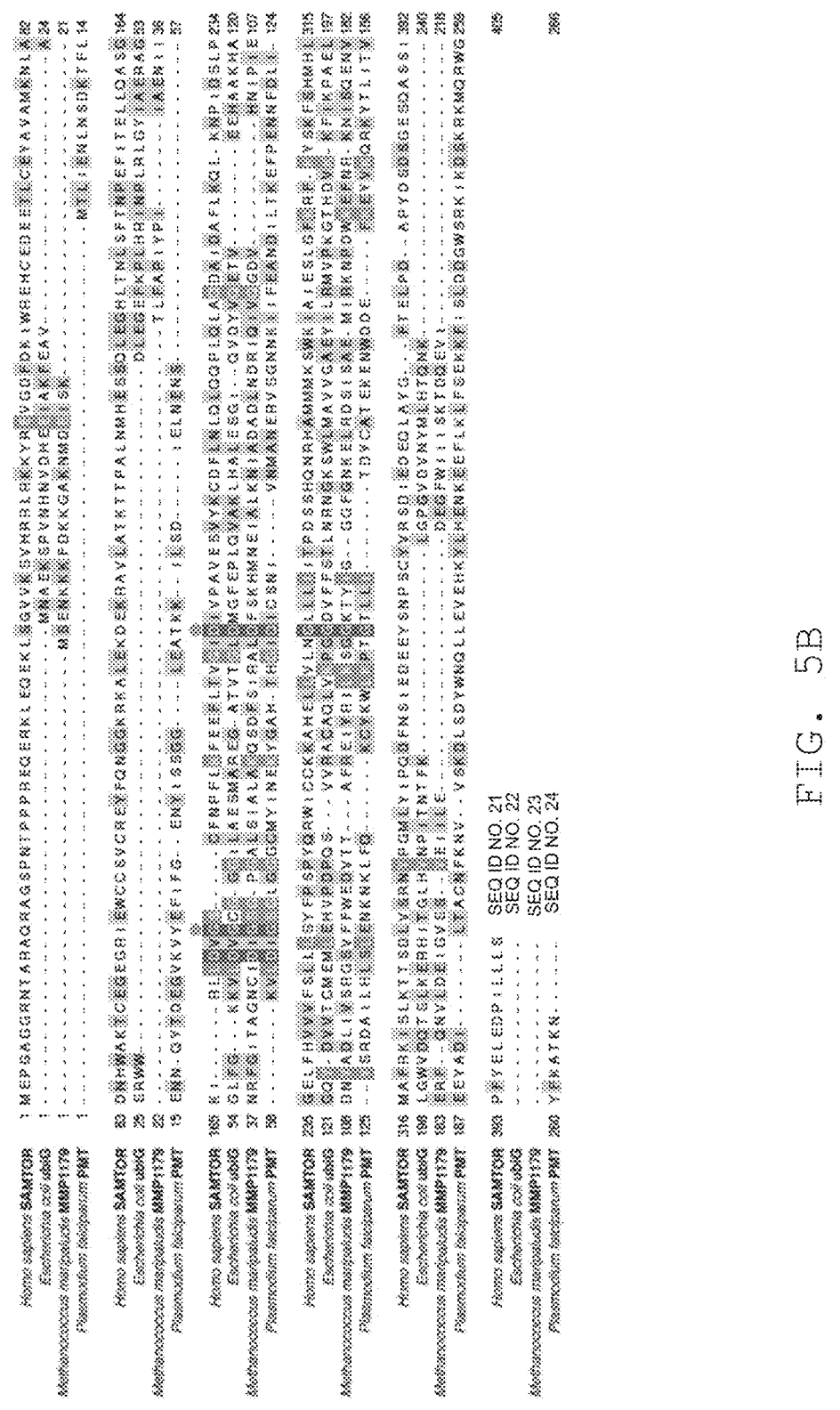

Mutagenesis of highly conserved residues in human SAMTOR yielded two mutants, G172A and D190A, which no longer bind SAM (FIG. 3E and FIGS. 5A and 5B). These mutants co-immunoprecipitated greater amounts of endogenous GATOR1 and KICSTOR than wild-type SAMTOR and the purified complexes were insensitive to SAM in vitro (FIG. 3F). Moreover, these mutants inhibited mTORC1 signaling to a similar extent as wild-type SAMTOR, despite their lower expression (FIG. 3G). Thus, SAMTOR must be able to bind SAM for SAM to disrupt the interaction of SAMTOR with GATOR1-KICSTOR. In contrast, SAMTOR does not have to bind SAM to inhibit mTORC1 signaling, indicating that this function of SAMTOR does not require a methylation event.

SAMTOR is a SAM Sensor for the mTORC1 Pathway

Figure 4A:
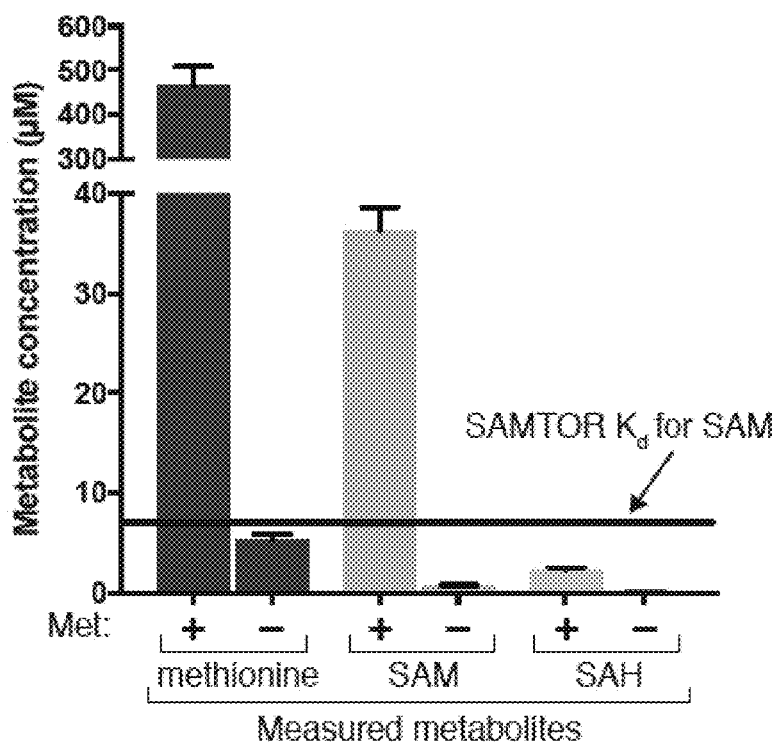
FIGS. 4A-4I depict SAMTOR senses SAM to signal methionine sufficiency to mTORC1.

Because SAM and SAH disrupt the interaction of SAMTOR with GATOR1-KICSTOR in vitro, we sought to determine if this is also true in cells. The enzyme methionine adenosyltransferase (MAT) synthesizes SAM from ATP and methionine, an essential amino acid, so that starvation for methionine should lower SAM levels, as has been observed previously in other systems (24, 25). Indeed, SAM concentrations in HEK-293T cells decreased upon methionine starvation, falling from above the dissociation constant of SAMTOR for SAM to below it (FIG. 4A). In contrast, in both methionine replete and starved cells, SAH concentrations were lower than the affinity of SAMTOR for SAH (FIG. 4A), making it unlikely that SAH is a physiologically relevant modulator of the binding of SAMTOR to GATOR1-KICSTOR.

Figure 4B:
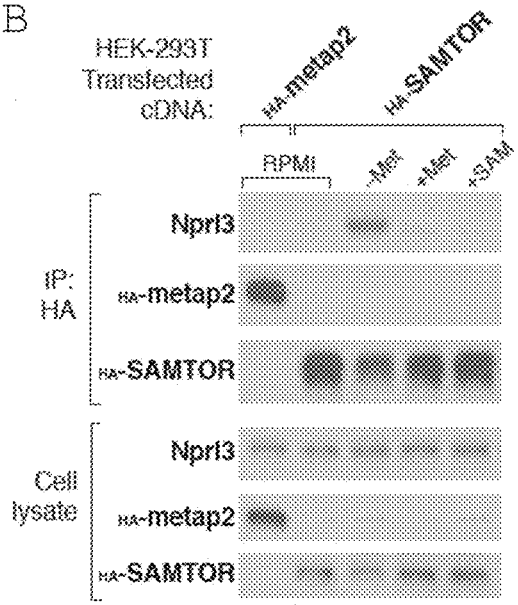

Consistent with the effects of SAM on the interaction between SAMTOR and GATOR1-KICSTOR in vitro, methionine starvation strongly increased this interaction in cells. Importantly, the addition to the methionine-starved cells of either methionine or SAM, which can enter cells when used at high concentrations, reduced the interaction to baseline levels (FIG. 4B).

Figure 4C:
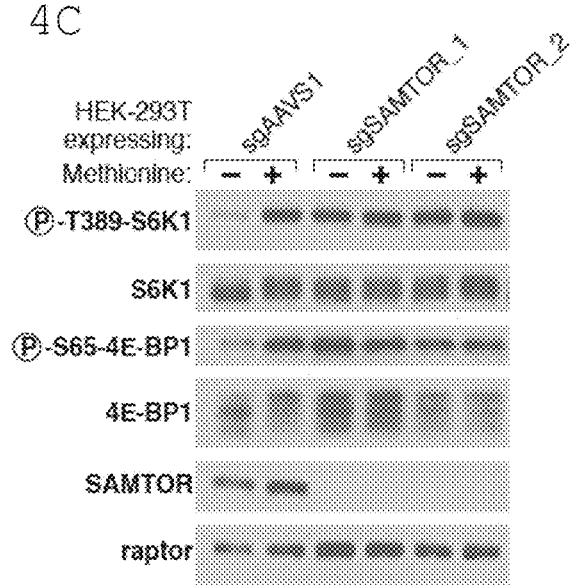
Figure 4D:
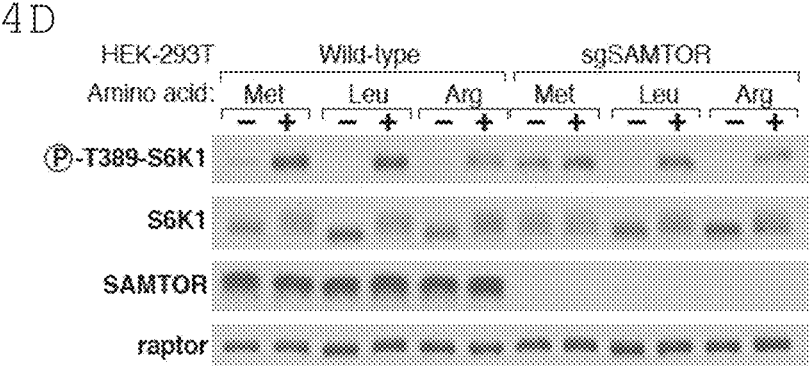
Figure 6A:
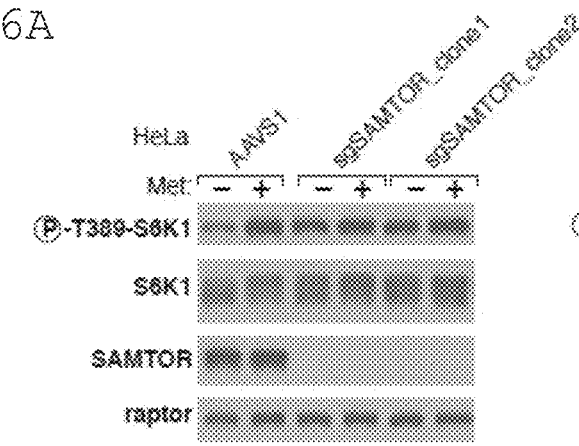
FIGS. 6A-6E.
Figure 6B:
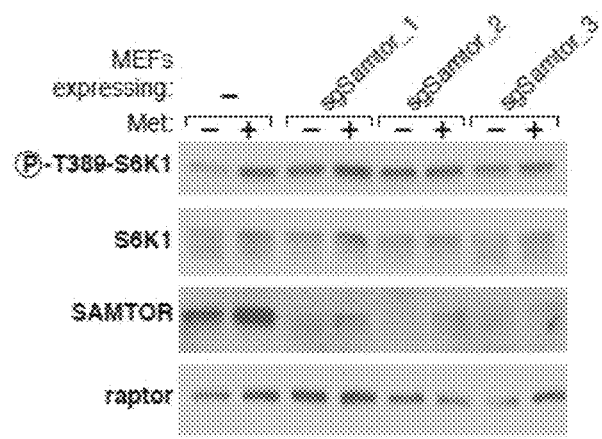
Figure 6C:
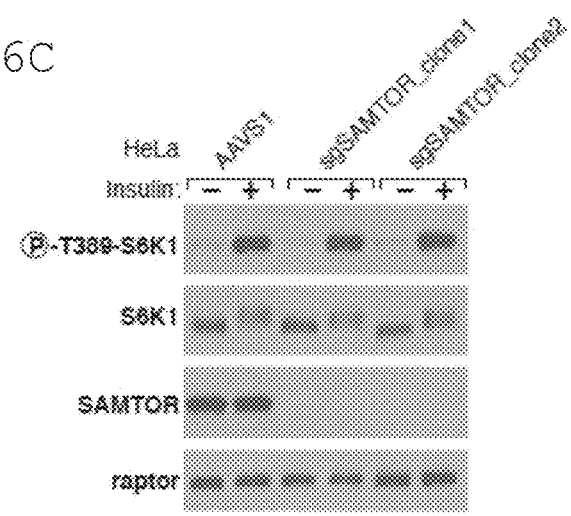

Given that SAMTOR is an inhibitor of mTORC1 signaling and methionine starvation promotes the interaction between SAMTOR and GATOR1-KICSTOR, we hypothesized that methionine starvation would also inhibit mTORC1 signaling. Indeed, in multiple cell types, methionine starvation inhibited mTORC1 signaling in a SAMTOR-dependent fashion, as measured by the phosphorylation of the mTORC1 substrates S6K1 and 4E-BP1 (FIG. 4C; FIGS. 6A and 6B). In contrast, loss of SAMTOR did not prevent the inhibition of mTORC1 signaling caused by withdrawal of leucine, arginine (FIG. 4D) or growth factors (FIG. 6C).

Figure 4E:
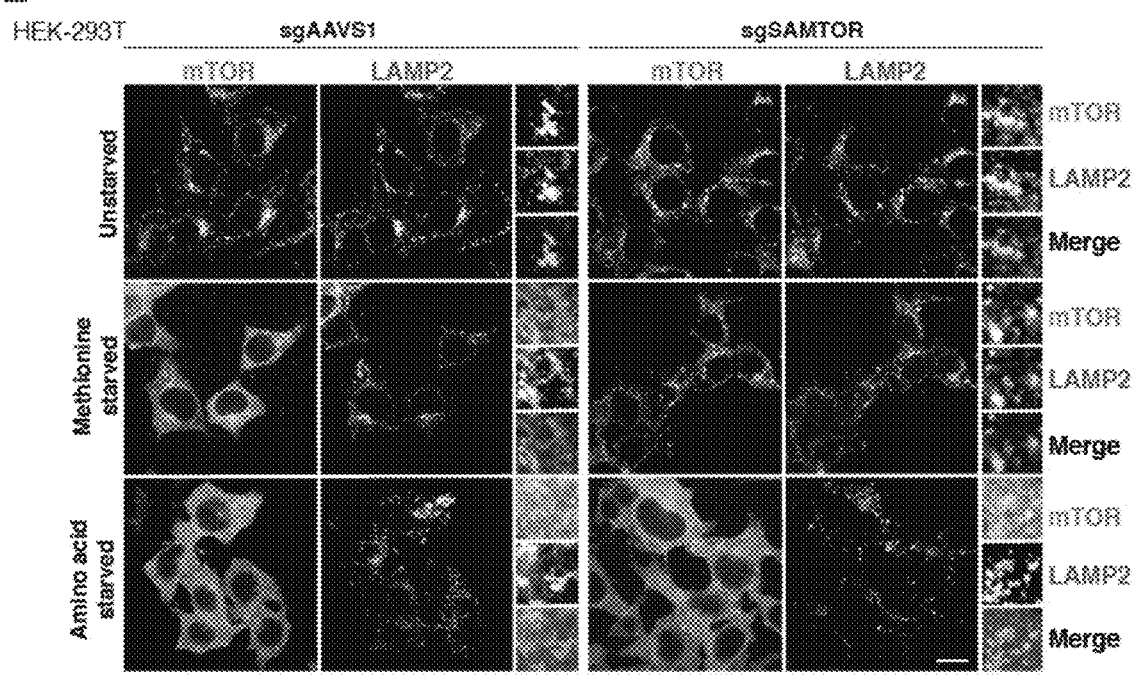
Figure 4F:
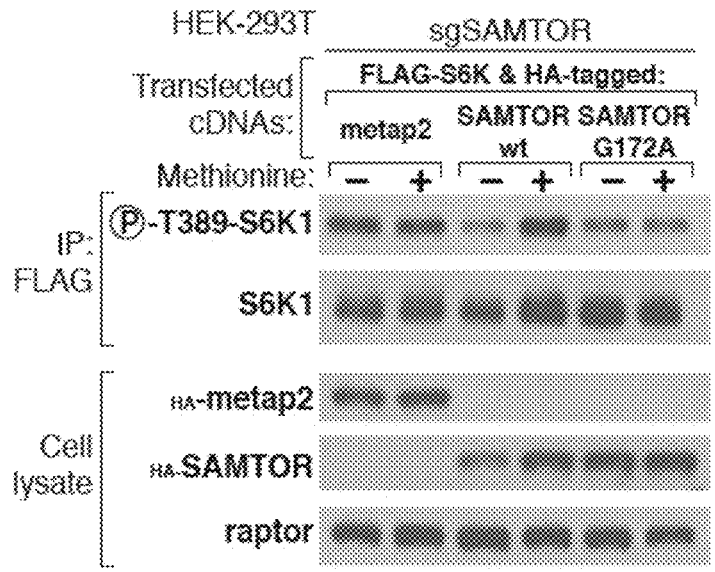
Figure 6D:
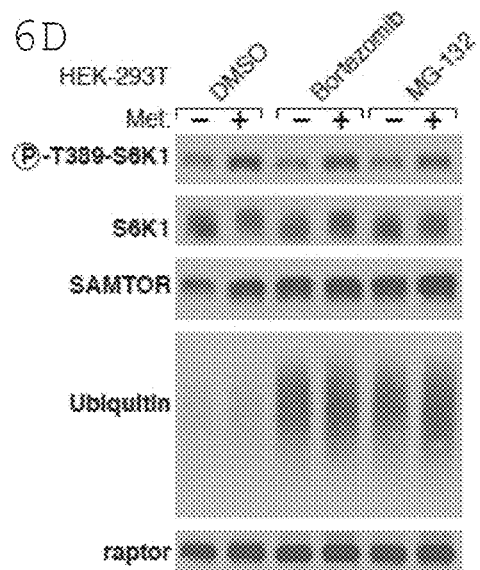

Consistent with the effects of SAMTOR overexpression (FIG. 2B), methionine starvation also reduced the co-localization of mTOR with lysosomes in wild-type but not SAMTOR-null cells (FIG. 4E). Furthermore, re-expression of wild type SAMTOR, but not a SAM-binding deficient mutant, restored the capacity of the mTORC1 pathway to sense methionine in the SAMTOR-null HEK-293T cells (FIG. 4F). Interestingly, methionine starvation partially reduces SAMTOR levels in a proteasome dependent manner (FIGS. 4B, 4C, and 4F, and FIG. 6D) but this degradation is not required for mTORC1 to respond to methionine starvation (FIG. 6D).

Figure 4G:
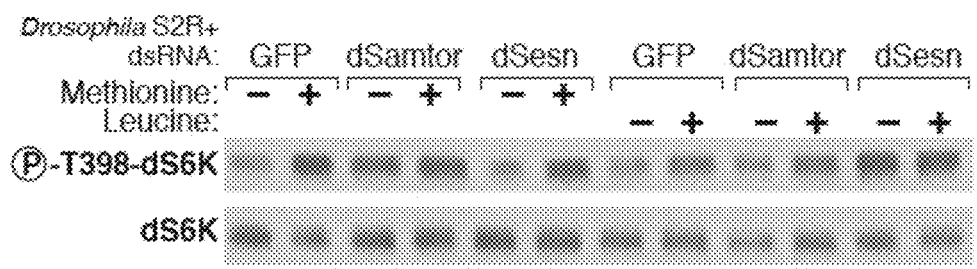
Figure 6E:
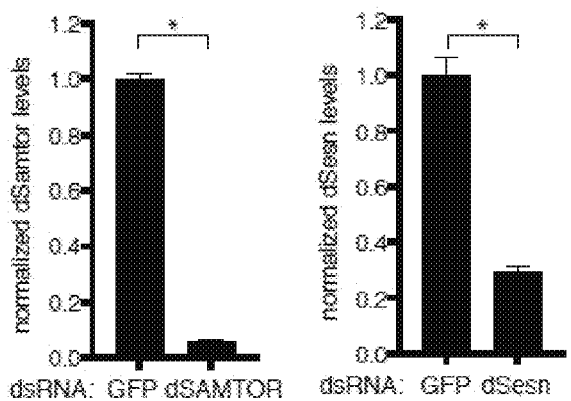

As in mammalian cells, dTOR signaling in *Drosophila* S2R+ cells also responds to environmental methionine and leucine levels, as detected by the phosphorylation of dS6K (FIG. 4G). Using dsRNA-induced RNAi, a knockdown of *Drosophila* SAMTOR (CG3570; dSamtor), but not of GFP or Sestrin2 (dSesn), prevented inhibition of dTOR signaling by methionine starvation (FIG. 4G and FIG. 6E). Importantly, the dsRNA targeting dSesn did prevent inhibition of dTOR by leucine starvation. These results suggest that the fly orthologs of SAMTOR and Sestrin2 have conserved roles in methionine and leucine sensing, respectively.

Figure 4H:
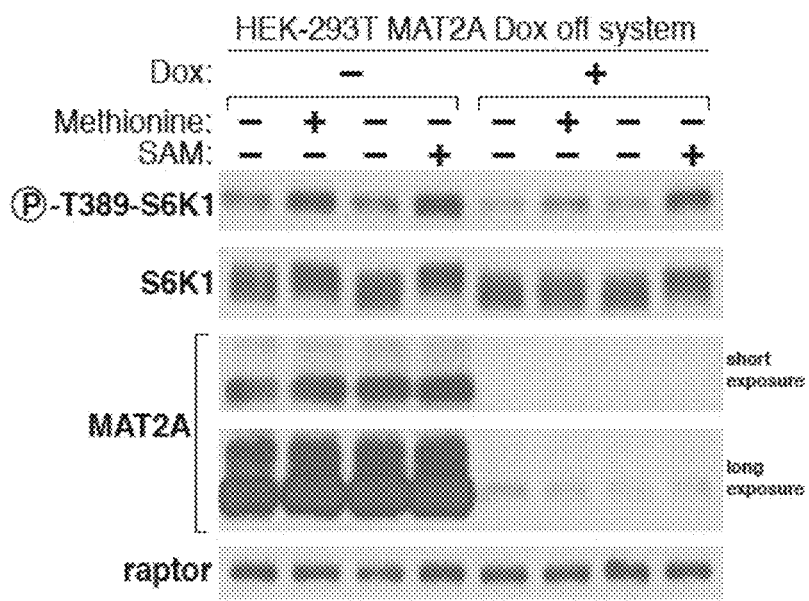

Our results show that SAMTOR is required for the mTORC1 pathway to detect changes in methionine levels and that this function requires its capacity to bind SAM. Moreover, the addition of SAM to methionine-starved cells reactivated mTORC1 signaling (FIG. 4H), indicating that it is the drop in SAM levels that mediates the inhibitory effects of methionine restriction on mTORC1. Given these findings, we predicted that the loss of methionine adenosyltransferase (MAT2A) would prevent mTORC1 from sensing methionine by blocking its conversion to SAM. Because MAT2A is essential in human cells (26, 27), we generated a doxycycline-repressible system in order to acutely suppress MAT2A expression (28). Consistent with SAMTOR sensing SAM rather than methionine directly, the loss of MAT2A greatly attenuated the capacity of mTORC1 to sense methionine while leaving its activation by SAM largely intact (FIG. 4H).

DISCUSSION

Figure 4I:
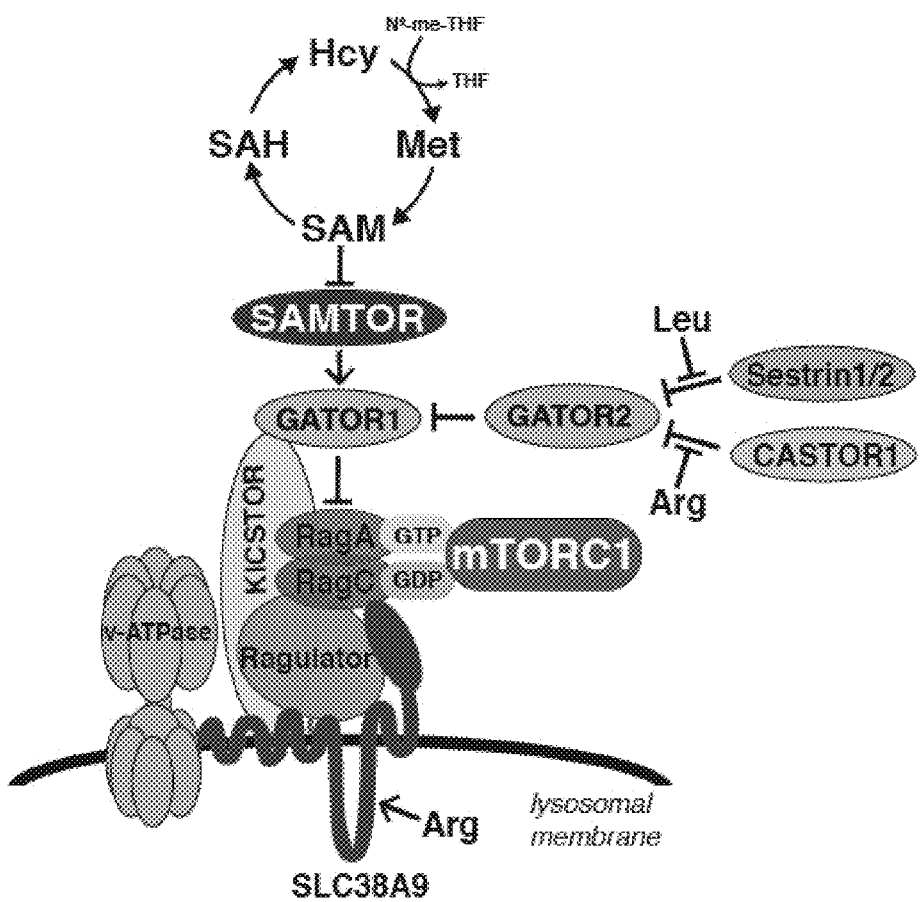

SAMTOR is a previously uncharacterized protein that has several properties suggesting that it functions as a SAM sensor that signals methionine sufficiency to mTORC1 (FIG. 4I): (i) it binds SAM with an affinity that is compatible with the drop in intracellular SAM concentrations caused by methionine starvation, (ii) SAMTOR is required for methionine starvation to inhibit mTORC1 signaling, and (iii) SAMTOR mutants that do not bind SAM cannot signal methionine sufficiency to mTORC1. As SAM levels can be affected by the availability of folate, betaine, and vitamin B12, SAMTOR may also link mTORC1 signaling to the availability of these metabolites (29).

The Rag GTPase pathway senses and integrates the presence of multiple amino acids upstream of mTORC1 (4, 8). Sestrin1 and Sestrin2 detect leucine, while CASTOR1 and SLC38A9 sense cytosolic and lysosomal arginine, respectively (15, 18). In contrast to the Sestrins and CASTOR1, which bind to GATOR2, SAMTOR interacts with GATOR1-KICSTOR. Our genetic data suggest that SAMTOR potentiates GATOR1 function, but the mechanism through which this occurs remains unknown. The interaction between SAMTOR and GATOR1 requires KICSTOR, which may reflect either a composite binding site or the requirement for KICSTOR to localize GATOR1 to the lysosomal surface. In addition, structural information will be needed to understand how the binding of SAM to SAMTOR disrupts its interaction with GATOR1 and KICSTOR.

Unlike leucine and arginine, which directly bind sensors upstream of mTORC1, methionine is sensed indirectly through SAM. SAM is a central metabolite required for most methylation reactions, including that of DNA (30), histones (24, 29), and phospholipids (31), and our work highlights its additional role as a signaling molecule. Interestingly, while Saccharomyces cerevisiae does not have a SAMTOR homologue, the yeast TOR pathway does sense methionine through the regulated methylation of the PP2A family of phosphatases (32).

In metazoans the mTORC1 pathway senses multiple amino acids, suggesting that these nutrients were, at times, scarce during their evolution. Two predictions can be made based on the existence of SAMTOR: (i) SAM can become limiting in certain nutritional states, and (ii) modulation of mTORC1 under these conditions is beneficial for maintaining organismal homeostasis. Indeed, diets low in methionine reduce tissue SAM levels and improve insulin sensitivity and extend lifespan in mice and rats (33-37). These benefits may be mediated in part via the SAMTOR-dependent inhibition of mTORC1, which is well appreciated to impact glucose metabolism and the aging process (1). Given that SAMTOR has a SAM-binding pocket, it may be possible to modulate SAMTOR function pharmacologically.

Materials and Methods

Materials

Reagents were obtained from the following sources: the antibody against SAMTOR (NBP1-94062) from Novus Biologicals; the antibody against Nprl3 (HPA011741) from Atlas Antibodies; antibodies against LAMP2 (sc-18822), MAT2A (sc-166452), ubiquitin (sc-8017), and HRP-labeled anti-mouse and anti-rabbit secondary antibodies from Santa Cruz Biotechnology; the antibody against raptor (2818718) from EMD Millipore; antibodies against phospho-T389 S6K1 (9234), S6K1 (2708), phospho-T398 dS6K, phospho-S65 4E-BP1 (9451), 4E-BP1 (9644), mTOR (2983), HRP-labeled anti-rabbit secondary antibody and the myc (2278) and FLAG (2368) epitopes from Cell Signaling Technology (CST); antibodies against the HA epitope from CST (3724) and Bethyl laboratories (A190208A); SAM (13956) from Cayman Chemical; [$^3$H]SAM from American Radiolabeled Chemicals, Inc. SAH (A9384), RPMI, anti-FLAG M2 affinity gel, and amino acids from Sigma Aldrich; DMEM from SAFC Biosciences; Effectene transfection reagent from Qiagen; XtremeGene9 and Complete Protease Cocktail from Roche; Alexa 488, 568 and 647-conjugated secondary antibodies, Schneider's media, and Inactivated Fetal Bovine Serum (IFS) from Invitrogen; amino acid-free RPMI, and amino acid-free Schneider's media from US Biologicals; and anti-HA magnetic beads, methionine-free RPMI from ThermoFisher Scientific. Antibodies against Wdr24 and SZT2 were generously provided by Jianxin Xie of Cell Signaling Technology, Inc. The dS6K antibody was a generous gift from Mary Stewart (North Dakota State University).

Plasmids Used

| Plasmid name | Addgene ID | Reference |
| --- | --- | --- |
| FLAG-SAMTOR in pRK5 | In progress | This study |
| FLAG-Kaptin in pRK5 | 87041 | Wolfson et al. 2017 |
| FLAG-metap2 in pRK5 | 32004 | Peterson et al. 2011 |

-continued

| Plasmid name | Addgene ID | Reference |
| --- | --- | --- |
| FLAG-DEPDC5 in pRK5 | 46340 | Bar-Peled et al. 2013 |
| FLAG-S6K1 in pRK5 | | Burnett et al. 1998 |
| FLAG-metap2 in pLJM1 | In progress | This study |
| FLAG-Kaptin in pLJM1 | In progress | This study |
| HA-metap2 in pRK5 | In progress | This study |
| HA-SAMTOR in pRK5 | In progress | This study |
| HA-SAMTOR(G172A) in pRK5 | In progress | This study |
| HA-SAMTOR(D190A) in pRK5 | In progress | This study |
| HA-RagA in pRK5 | | Sancak et al. |
| HA-RagC in pRK5 | | Sancak et al. |
| HA-RagA(Q66L) in pRK5 | | Sancak et al. |
| HA-RagC(S75N) in pRK5 | | Sancak et al. |
| Myc-metap2 in pRK5 | In progress | This study |
| Myc-SAMTOR in pRK5 | In progress | This study |
| GFP-metap2 pLC242 | In progress | This study |
| GFP-Sestrin2 pLC242 | In progress | This study |
| GFP-SAMTOR pLC242 | In progress | This study |
| MAT2A (sg1_resistant) in pCW57.1 | In progress | This study |
| MAT2A_sg1 in pLentiCRISPR | In progress | This study |
| SAMTOR_sg1 in pLentiCRISPR | In progress | This study |
| SAMTOR_sg2 in pLentiCRISPR | In progress | This study |
| Mm_Samtor_sg1 in pLentiCRISPR | In progress | This study |
| Mm_Samtor_sg2 in pLentiCRISPR | In progress | This study |
| Mm_Samtor_sg3 in pLentiCRISPR | In progress | This study |
| SAMTOR_sg1 in pX330 | In progress | This study |

Cell Lines and Tissue Culture

HeLa, HEK-293T, p53−/−MEFs were cultured in DMEM with 10% IFS and supplemented with 2 mM glutamine. These cell lines were maintained at 37° C. and 5% $CO_2$. Drosophila S2R+ cells were cultured in Schneider's media with 10% IFS at 25° C. and 5% $CO_2$.

Transfections

For the transfection of cDNA expression constructs into HEK-293T cells, 1.5-2 million cells were seeded in 10 cm dishes. Using the polyethylenimine method (38), cells were transfected 24 hours after seeding with the indicated pRK5 based expression vectors. Experiments were done 36-48 hours after transfection. The total amount of DNA transfected was normalized to 5 µg with the empty pRK5 vector. The following amounts of cDNA were used in the indicated figures.

Figure 2A:
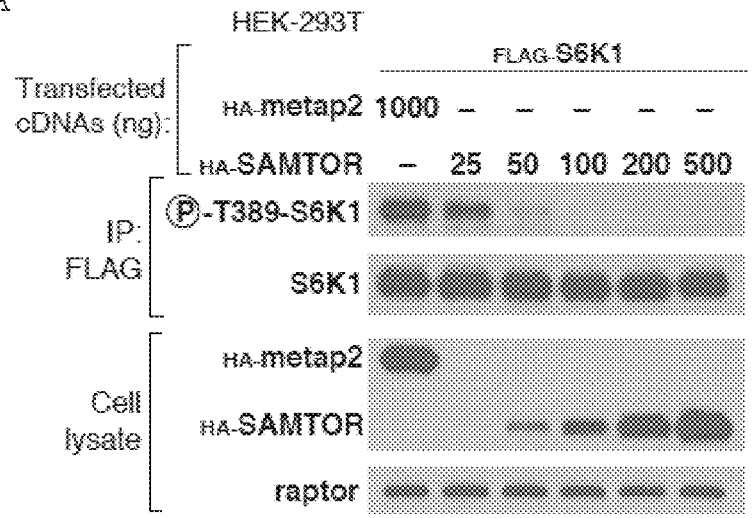
FIGS. 2A-2D depicts SAMTOR is a negative regulator of mTORC1 signaling that acts upstream of the Rag GTPases, GATOR1, and KICSTOR.
Figure 2B:
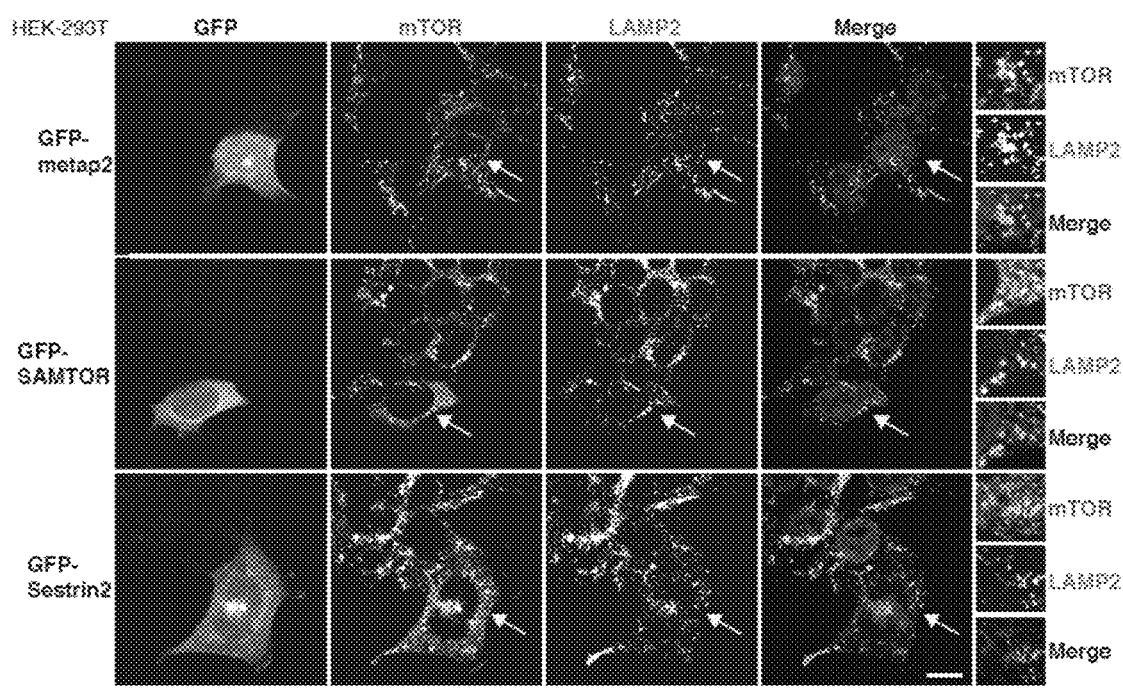
Figure 2C:
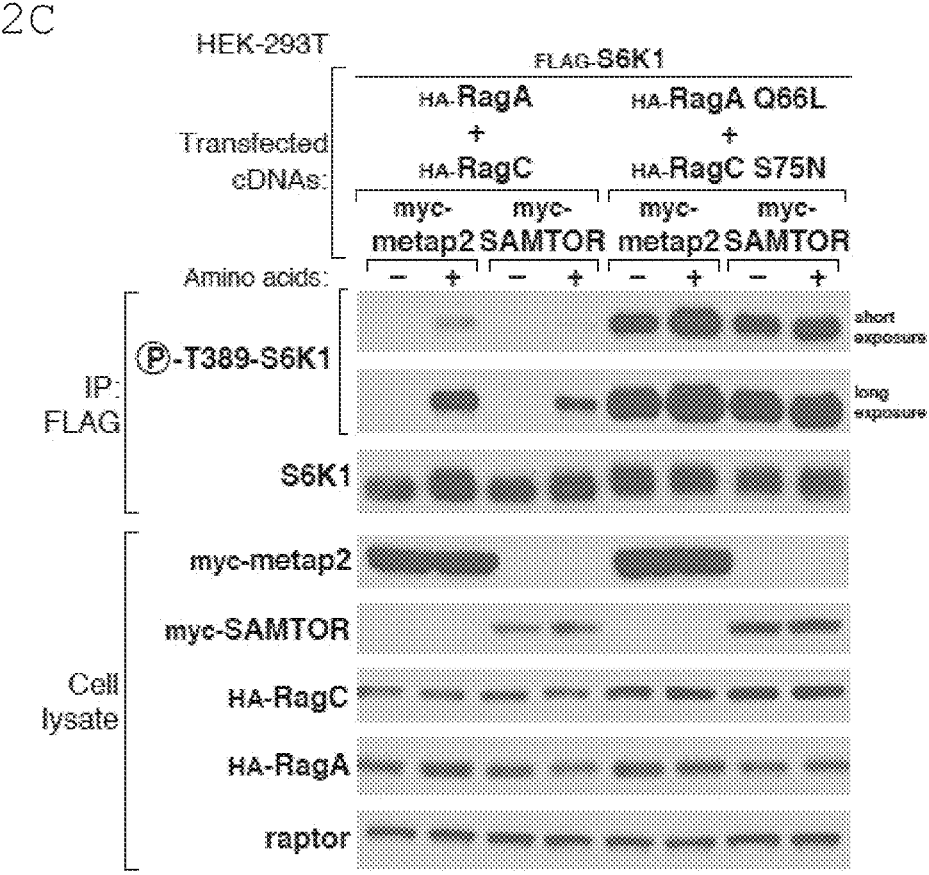
Figure 2D:
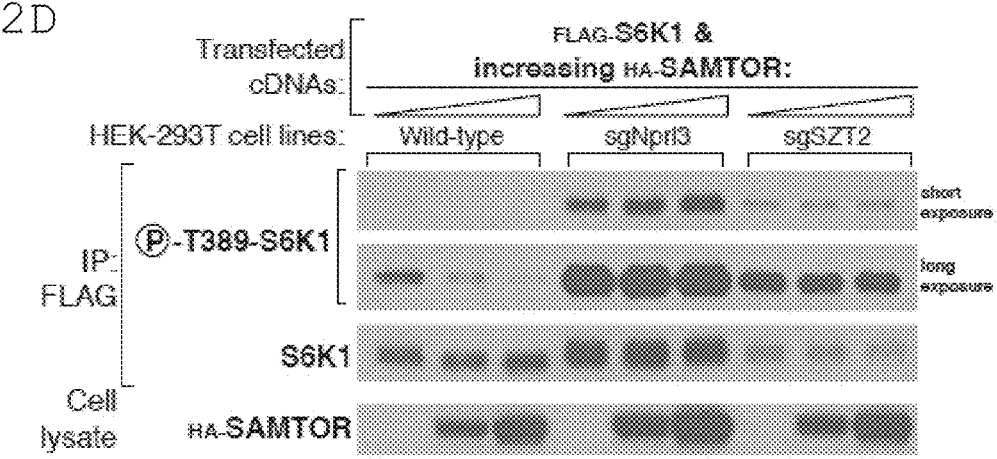

FIG. 1C: 250 ng FLAG-metap2, 250 ng FLAG-SAMTOR, 350 ng FLAG-DEPDC5, or 75 ng FLAG-KPTN;

FIG. 2A: 2 ng FLAG-S6K1 and the amounts as indicated in the figure for the HA-tagged constructs;

FIG. 2C: 2 ng FLAG-S6K1, 150 ng HA-RagA/C, or HA-RagA (Q66L) and HA-RagC (S75N);

FIG. 2D: 2 ng FLAG-S6K1 and 0 ng, 25 ng, or 50 ng HA-SAMTOR;

FIG. 3F: 150 ng HA-metap2, 150 ng HA-SAMTOR, 200 ng HA-SAMTOR (G172A), or 190 ng HA-SAMTOR (D190A);

FIG. 3G: 2 ng FLAG-S6K and 0 ng, 25 ng, or 100 ng HA-tagged SAMTOR wild-type or mutant;

FIG. 4B: 50 ng HA-metap2 or 25 ng HA-SAMTOR; and

FIG. 4F: 2 ng FLAG-S6K, 25 ng HA-metap2, 10 ng HA-SAMTOR, or 40 ng of HA-SAMTOR (G172A).

Lentiviral Production and Lentiviral Infections

HEK-293T cells were seeded at a density of 750,000 cells per well of a 6-well plate in DMEM with 20% IFS. 24 hours after seeding, VSV-G envelope and CMV AVPR packaging plasmids were co-transfected with either pLJM1 containing cDNAs, pLentiCRISPRv2 with indicated guide sequences, or pCW57.1_tTA with the MAT2A (sg1_resistant) cDNA, using XTremeGene 9 transfection reagent (Roche). 12 hours after transfection, the media was changed to DMEM 20% IFS. 36 hours after the media change, the virus-containing supernatant was collected and passed through a 0.45 µm filter. Target cells were plated in 6-well plates with 8 µg/mL polybrene and incubated with virus containing media. Infections with pLentiCRISPRv2 were spinfected at 2200 rpm for 45 minutes at 37° C. 24-48 hours later, the media was changed to fresh media containing either puromycin for pLJM1 or pLentiCRISPR or blasticidin for pCW57.1_tTA.

Cell Lysis and Immunoprecipitations

Cells were rinsed with cold PBS and lysed in lysis buffer (1% Triton, 10 mM β-glycerol phosphate, 10 mM pyrophosphate, 40 mM Hepes pH 7.4, 2.5 mM MgCl2 and 1 tablet of EDTA-free protease inhibitor [Roche] (per 25 ml buffer)). Cell lysates were cleared by centrifugation in microcentrifuge (15,000 rpm for 10 minutes at 4° C.). Cell lysate samples were prepared by addition of 5× sample buffer (0.242 M Tris, 10% SDS, 25% glycerol, 0.5 M DTT, and bromophenol blue), resolved by 8%-16% SDS-PAGE, and analyzed by immunoblotting.

For anti-FLAG immunoprecipitations, anti-FLAG M2 Affinity Gel (SIGMA A2220) was washed with lysis buffer three times then resuspended to a ratio of 50:50 affinity gel to lysis buffer. 25 µL of a well-mixed slurry was added to cleared lysates and incubated at 4° C. in a shaker for 90-120 minutes. For anti-HA immunoprecipitations, magnetic anti-HA beads (Pierce) were washed three times with lysis buffer. 30 µL of resuspended beads in lysis buffer was added to cleared lysates and incubated at 4° C. in a shaker for 90-120 minutes. Immunoprecipitates were then washed three times, once with lysis buffer and twice with lysis buffer with 500 mM NaCl. Immunoprecipitated proteins were denatured by addition of 50 µL of SDS-containing sample buffer (0.121 M Tris, 5% SDS, 12.5% glycerol, 0.25 M DTT, and bromophenol blue) and boiled for 5 minutes. Denatured samples were resolved by 8%-12% SDS-PAGE, and analyzed by immunoblotting.

RNAi in *Drosophila* S2R+ Cells and qPCR

The dsRNA against dSesn was designed as described in (7). To minimize off-target effects, we used the DRSC tool at flyrnai.org/RNAi_find_frag-free.html and excluded regions of 19-mer-or-greater identity to any other *Drosophila* transcripts. The dsRNA targeting GFP was used as a negative control. The dsRNA against dSamtor was picked from searching CG3570 at DRSC/TRiP Functional Genomics Resources website: flyrnai.org/cgi-bin/DRSC_gene_lookup.pl. DRSC24231 was used in this work. Primer sequences used to amplify DNA templates for dsRNA synthesis for GFP, dSamtor and dSesn, including underlined 5' and 3' T7 promoter sequences, are as follows:

F-dsGFP primer:
(SEQ ID NO: 1)
GAATTAATACGACTCACTATAGGGAGAAGCTGACCCTGAAGTTCATCTG;

R-dsGFP primer:
(SEQ ID NO: 2)
GAATTAATACGACTCACTATAGGGAGATATAGACGTTGTGGCTGTTGTAGTT;

F-dsdSamtor primer:
(SEQ ID NO: 3)
GAATTAATACGACTCACTATAGGGAGATGGAATCCTACAGAGCCGAGGG;

R-dsdSamtor primer:
(SEQ ID NO: 4)
GAATTAATACGACTCACTATAGGGAGACGTACCCGTAGCAGTCCAATCCTG;

F-dsdSesn primer:
(SEQ ID NO: 5)
GAATTAATACGACTCACTATAGGGAGAGACTACGACTATGGCGAAGTGAA;
and R-dsdSesn primer:
(SEQ ID NO: 6)
GAATTAATACGACTCACTATAGGGAGATCAAGTCATATAGCGCATTATCTCG.

On day one, 2 million S2R+ cells were plated in 6-well culture dishes in 1.5 ml of Schneider's media with 10% IFS. Cells were transfected with 2 µg of each dsRNA using Effectene transfection reagent (Qiagen) after 12-24 hours. On day three, a second round of dsRNA transfection was performed. On day five, 1.2 million cells were plated in 12-well culture dishes coated with fibronectin in advance. 3-4 hours later, cells were rinsed once with amino acid-free Schneider's media, and starved for either methionine or leucine by replacing the media with methionine or leucine-free media for 1 hour. To stimulate with methionine or leucine, the media was replaced with complete Schneider's media for 30 minutes. Cells were then rinsed with cold PBS once, lysed in lysis buffer, and subjected to immunoblotting for the levels of phospho-T398 dS6K and total dS6K.

To validate knockdown of dSamtor and dSesn, the following primer pairs were used in qPCR reactions due to the lack of available antibodies to these proteins. We used alpha-tubulin as internal standard control. The data were analyzed via the ΔΔCt method as described previously (20).

F-alpha-tubulin:
(SEQ ID NO: 7)
CAACCAGATGGTCAAGTGCG;

R-alpha-tubulin:
(SEQ ID NO: 8)
ACGTCCTTGGGCACAACATC;

F-dSamtor:
(SEQ ID NO: 9)
GACCAACGATGGGAAGGTGG;

R-dSamtor:
(SEQ ID NO: 10)
GCTCTGTAGGATTCCAGGAGT;

F-dSesn:
(SEQ ID NO: 11)
TCCGCTGCCTAACGATTACAG;
and

R-dSesn:
(SEQ ID NO: 12)
TTCACCAGATACGGACACTGA.

Sequence Analyses of SAMTOR

We assessed the sequence conservation of SAMTOR with the PHMMER online tool (ebi.ac.uk/Tools/hmmer/search/phmmer) and performed secondary structure predictions using the HHPred online tool (toolkit.tuebingen.mpg.de/#/tools/hhpred). Note: the name for SAMTOR in the BioPlex dataset is C7orf60. When we searched C7orf60 on multiple websites, including Genecards and Uniprot, we found that C7orf60 is also associated with another name: Probable BMT2 (Base Methyltransferase Of 25S rRNA 2) homolog. BMT2 is a nuclear RNA methyltransferase in *Saccharomy-* ces cerevisiae (39). However, in our own extensive analyses we could find no similarity between human C7orf60 (SAMTOR) and yeast BMT2 on the protein sequence level. We suspect that the BMT2 name was erroneously assigned in an automated fashion to C7orf60 because both contain a predicted Class I Rossmann fold methyltransferase domain.

Generation of CRISPR/Cas9 Genetically Modified Cells with Loss of SAMTOR or MAT2A To generate HEK-293T or HeLa cells with loss of SAMTOR, the following sense (S) and antisense (AS) oligonucleotides encoding the guide RNAs were cloned into pX330:

```
sgSAMTOR_guide1_S:
                                    (SEQ ID NO: 13)
caccgGAAATACTGCTCGTGCGCAG;
and sgSAMTOR_guide1_AS:
                                    (SEQ ID NO: 14)
aaacCTGCGCACGAGCAGTATTTCc.
```

Control cells were generated by targeting the AAVS1 locus as described before (10, 40). On day one, 2 million HEK-293T cells were seeded in a 10-cm plate. Twenty-four hours after seeding, each well was transfected with 1 µg shGFP pLKO, 1 µg of the pX330 guide construct and 3 µg of empty pRK5 using XtremeGene9. Two days after transfection, cells were moved to a new 10-cm plate into puromycin containing media. Forty-eight hours after selection, the media was switched to media not containing puromycin. Cells were allowed to recover for 1 week after selection prior to single-cell sorting with a flow cytometer into the wells of a 96-well plate containing 150 µl of DMEM supplemented with 30% IFS.

For HeLa cells, on day one, 1 million cells were plated in a 10-cm dish. 24 hours later, the cells were transfected with 1 µg shGFP pLKO and 1 µg of the pX330 guide construct using FuGENE. Selection with puromycin was started the following day to eliminate untransfected cells. 48 hours after selection, the medium was aspirated and replenished with fresh medium without puromycin and the cells were single-cell sorted as described above. Cells were grown for two weeks and the resultant colonies were trypsinized and expanded. Cell clones were validated via immunoblotting.

Human SAMTOR, mouse SAMTOR, and MAT2A were depleted using the lentiviral pLentiCRISPRv2 system. The following sense (S) and antisense (AS) oligonucleotides were cloned into pLentiCRISPRv2:

```
Human SAMTOR
sgSAMTOR_1 (S):
                                    (SEQ ID NO: 15)
caccgGAAATACTGCTCGTGCGCAG sgSAMTOR_1 (AS):
                                    (SEQ ID NO: 16)
aaacCTGCGCACGAGCAGTATTTCc sgSAMTOR_2 (S):
                                    (SEQ ID NO: 17)
caccgGATATGGAGCCAGGGGCCGG sgSAMTOR_2 (AS):
                                    (SEQ ID NO: 18)
aaacCCGGCCCCTGGCTCCATATCc Mouse Samtor
sgMmSamtor_1 (S):
                                    (SEQ ID NO: 19)
caccgGCAGGAGAAGCTGTCCGGGG sgMmSamtor_1 (AS):
                                    (SEQ ID NO: 20)
aaacCGCCACTAAGACCACTCCAGc sgMmSamtor_2 (S):
                                    (SEQ ID NO: 21)
caccgCTCCGCAAGAAGTACCGCGA sgMmSamtor_2 (AS):
                                    (SEQ ID NO: 22)
aaacTCGCGGTACTTCTTGCGGAGc sgMmSamtor_3 (S):
                                    (SEQ ID NO: 23)
caccgATGAACGCTCTTCACCACCC sgMmSamtor_3 (AS):
                                    (SEQ ID NO: 24)
aaacGGGTGGTGAAGAGCGTTCATc Human MAT2A
sgMAT2A_1 (S):
                                    (SEQ ID NO: 25)
caccgTTAAAGGAGGTCTGTGCCGG sgMAT2A_1 (AS):
                                    (SEQ ID NO: 26)
aaacCCGGCACAGACCTCCTTTAAc
```

Lentivirus was produced and used to infect cells as described above. To give Cas9 time to cut the targeted locus, experiments were performed at least one week after transduction.

Generation of the MAT2A Doxycycline-Repressible System

The MAT2A cDNA was amplified from cDNA prepared from total cell HEK-293T RNA. The following synonymous mutations were introduced by overhang extension PCR into the MAT2A coding sequence: 144G>A to remove a BamHI restriction site and 939G>A to mutate the protospacer adjacent motif of the sgMAT2A_1 sgRNA sequence. Using NheI and BamHI restriction sites, the MAT2A_sg1 cDNA was cloned downstream of the tetO element in the lentiviral pCW57.1 vector, which encodes the tet/dox-repressible tTA trans-factor and a blasticidin resistance gene. Lentivirus was produced as described above and was used to transduce wild-type HEK-293T cells. After 24 hours, blasticidin was added to the cells to remove untransduced cells. After 48 hours of selection, cells were transduced with lentivirus produced from pLentiCRISPRv2 with the MAT2A_sg1 guide sequence. After puromycin selection, cells were single cell sorted using flow cytometry into 96-well plates containing DMEM 30% IFS. Resulting clones were expanded and screened by replica plating for sensitivity to 30 ng/mL doxycycline. Positive clones were then screened by immunoblotting for MAT2A protein in whole cell lysates.

Immunofluorescence Assays

Immunofluorescence assays were performed as described previously (10). Briefly, for the experiment in FIG. 2B, 2 million cells growing in a 10 cm dish and plated 24 hours before were transfected with 150 ng of the cDNAs for GFP-metap2, GFP-SAMTOR, or GPF-Sestrin2 in pIC242. After 24 hours, 400,000 cells were counted and plated on fibronectin-coated glass coverslips (TED PELLA, Inc.) in 6-well tissue culture plates. For the experiment in FIG. 4E, 400,000 HEK-293T cells were plated on fibronectin-coated glass coverslips in 6-well tissue culture plates. After 24 hours, the slides were rinsed once with PBS and fixed with 4% paraformaldehyde in PBS for 15 minutes at room temperature. The slides were then rinsed three times with PBS and the cells permeabilized with 0.05% Triton X-100 in PBS for 5 minutes at room temperature. The slides were rinsed three times with PBS and then blocked for 1 hour in Odyssey blocking buffer at room temperature. The slides were incubated with primary antibody in Odyssey blocking buffer at 4° C. overnight, rinsed three times with PBS, and incubated with secondary antibodies produced in donkey (diluted 1:1000 in Odyssey blocking buffer) for 50 minutes at room temperature in the dark, and washed three times with PBS. The primary antibodies used were directed against mTOR (CST; 1:100-1:300 dilution), LAMP2 (Santa Cruz Biotechnology; 1:300 dilution). Slides were mounted on glass coverslips using Vectashield (Vector Laboratories) containing DAPI.

Images were acquired on a Zeiss AxioVert200M microscope with a 63× oil immersion objective and a Yokogawa CSU-22 spinning disk confocal head with a *Borealis* modification (Spectral Applied Research/Andor) and a Hamamatsu ORCA-ER CCD camera. The MetaMorph software package (Molecular Devices) was used to control the hardware and image acquisition. The excitation lasers used to capture the images were 405 nm, 488 nm, 561 nm and 640 nm. DAPI channel is not shown in the main images, but it is in the insets as a blue signal.

In the experiment in FIG. 2B, an Alexa568-conjugated secondary antibody was used for the mTOR staining and the excitation wavelength was 561 nm, while an Alexa647-conjugated secondary antibody was used for the LAMP2 staining and the excitation wavelength was 640 nm. The GFP signal was detected by excitation with the 488 nm laser without use of a primary or secondary antibody.

In the experiment in FIG. 4E, an Alexa488-conjugated secondary antibody was used for mTOR staining and the excitation wavelength was 488 nm, while an Alexa568-conjugated secondary antibody was used for the LAMP2 staining and the excitation wavelength was 561 nm.

Purification of Proteins Expressed in Human Cells for the SAM Binding Assay

For radiolabelled SAM binding assays using FLAG-tagged wild-type SAMTOR (FIG. 3B), suspension HEK-293F cells were seeded at 2.5 million cells/ml, and the pRK5-FLAG-SAMTOR cDNA was transfected using polyethylenimine. 72-96 hours after transfection, cells were rinsed one time in cold PBS and lysed in 1% Triton lysis buffer (1% Triton, 40 mM Hepes pH 7.4, 2.5 mM MgCl2 and 1 tablet of EDTA-free protease inhibitor [Roche] per 25 ml buffer). Following anti-FLAG immunoprecipitation, the beads were washed 4 times with lysis buffer containing 500 mM NaCl and the protein was eluted in FLAG Elution Buffer (40 mM Hepes pH 7.4, 150 mM NaCl, 2.5 mM MgCl2 and 0.5 mg/ml FLAG peptide) for 1 hour at 4° C. The eluted protein was further purified via size-exclusion chromatography on a Superdex S75 10/300 column (GE Healthcare) equilibrated in running buffer (20 mM Hepes pH 7.4, 150 mM NaCl, 1 mM DTT) and concentrated to approximately 1 mg/ml. 1 μl of the protein was examined by SDS-PAGE followed by Coomassie blue staining for purity analysis. 5 μg of purified FLAG-SAMTOR protein was used in each sample in the experiment in FIG. 3B.

For radiolabeled SAM binding assays using HA tagged SAMTOR (wild-type, D190A and G172A) (FIG. 3E), 6 million HEK-293T cells were plated in a 15 cm plate. 24 hours after plating, the cells were transfected using polyethylenimine with the pRK5-based cDNA expression plasmids indicated in the figures in the following amounts: 12 μg HA-GST Rap2A, 15 μg HA-SAMTOR wild-type or mutants. The total amount of plasmid DNA in each plate was normalized to 20 μg total DNA with empty-pRK5. In FIG. 3E, each plasmid was transfected to five plates. 48 hours after transfection, cells were lysed as previously described and the lysates with same plasmid transfected was mixed and combined.

SAM Binding Assay

Anti-FLAG (Sigma) or anti-HA magnetic beads (Pierce) were blocked by rotating in 1 μg/μl bovine serum albumin (BSA) for 30 minutes at 4° C., then washed three times in lysis buffer, and re-suspended in an equal volume of lysis buffer.

30 μl of a bead slurry was added to each of the purified proteins or clarified cell lysates and incubated for 90 minutes at 4° C. The beads were then washed as previously and incubated for one hour on ice in cytosolic buffer (0.1% Triton, 40 mM HEPES pH 7.4, 10 mM NaCl, 150 mM KCl, 2.5 mM MgCl2) with the indicated amount of [3H]-labeled SAM and unlabeled SAM or SAH. At the end of one hour, the beads were aspirated dry and rapidly washed four times with binding wash buffer (0.1% Triton, 40 mM HEPES pH 7.4, 300 mM NaCl, 2.5 mM MgCl2). The beads were aspirated dry again and resuspended in 80 μl of cytosolic buffer. Each sample was mixed well and then 15 μl aliquots were separately quantified using a TriCarb scintillation counter (Perkin Elmer). This process was repeated in pairs for each sample, to ensure similar incubation and wash times for all samples analyzed across different experiments.

For radiolabeled SAM binding assays using HA tagged SAMTOR (wild-type, D190A and G172A), an immunoprecipitation for each sample was performed in parallel. After washing three times as previously described, the proteins were eluted in lysis buffer with 500 mM NaCl and 1 mg/ml HA peptide for 1 hour at 30° C. The eluted proteins were denatured by the addition of sample buffer and boiled for 5 minutes at 95° C., resolved by 10% SDS-PAGE, and analyzed with Coomassie blue staining.

$K_d$ and $K_i$ Calculations

The affinities for SAM and SAH of human FLAG-SAMTOR were determined by first normalizing the bound [$^3$H]-labeled SAM concentrations across three separate binding assays performed with varying amounts of cold SAM or SAH. These values were plotted and fit to a hyperbolic equation (Cheng-Prusoff equation) to estimate the $IC_{50}$ value. $K_d$ or $K_i$ values were derived from the IC50 value using the equation: $K_d$ or $K_i = IC_{50}/(1+([^3H]SAM)/K_d)$.

In Vitro GATOR1-SAMTOR Dissociation Assay

HEK-293T cells stably expressing endogenous FLAG-tagged Depdc5 were lysed and subjected to anti-FLAG immunoprecipitations as described above. The GATOR1-SAMTOR complexes immobilized on the FLAG beads were washed twice in lysis buffer with 250 mM NaCl, and then incubated for 25 minutes in 0.3 ml of cytosolic buffer (0.1% Triton, 40 mM HEPES pH7.4, 10 mM NaCl, 150 mM KCl, 2.5 mM MgCl2) with the indicated concentrations of SAM or SAH in the cold. The amount of GATOR1, SAMTOR, GATOR2, and KICSTOR that remained bound was assayed by SDS-PAGE and immunoblotting as described previously.

LC/MS-Based Metabolomics and Quantification of Metabolite Abundance

LC/MS-based metabolomics were performed and analyzed as previously described (41, 42), with 500 nM isotope-labeled internal standards were used. SAM standards were purchased from Cayman Chemical (13956), and SAH from SIGMA (A9384). Briefly, 80% methanol extraction buffer with 500 nM isotope-labeled internal standards was used for whole cell metabolite extraction. Samples were briefly vortexed and dried by vacuum centrifugation. Samples were stored at −80° C. until analyzed. On the day of analysis, samples were resuspended in 100 μL of LC/MS grade water and the insoluble fraction was cleared by centrifugation at 15,000 rpm. The supernatant was then analyzed as previously described by LC/MS (41, 42).

Statistical Analysis

Two-tailed t tests were used for comparison between two groups. All comparisons were two-sided, and P values of less than 0.001 were considered to indicate statistical significance.

REFERENCES

1. R. A. Saxton, D. M. Sabatini, mTOR Signaling in Growth, Metabolism, and Disease. Cell 168, 960-976 (2017).
2. C. C. Dibble, B. D. Manning, Signal integration by mTORC1 coordinates nutrient input with biosynthetic output. Nat Cell Biol 15, 555-564 (2013).
3. J. L. Jewell, R. C. Russell, K. L. Guan, Amino acid signalling upstream of mTOR. Nature reviews. Molecular cell biology 14, 133-139 (2013).
4. Y. Sancak et al., The Rag GTPases bind raptor and mediate amino acid signaling to mTORC1. Science 320, 1496-1501 (2008).
5. E. Kim, P. Goraksha-Hicks, L. Li, T. P. Neufeld, K. L. Guan, Regulation of TORC1 by Rag GTPases in nutrient response. Nat Cell Biol 10, 935-945 (2008).
6. Z. Y. Tsun et al., The folliculin tumor suppressor is a GAP for the RagC/D GTPases that signal amino acid levels to mTORC1. Mol Cell 52, 495-505 (2013).
7. L. Bar-Peled et al., A Tumor suppressor complex with GAP activity for the Rag GTPases that signal amino acid sufficiency to mTORC1. Science 340, 1100-1106 (2013).
8. Y. Sancak et al., Ragulator-Rag complex targets mTORC1 to the lysosomal surface and is necessary for its activation by amino acids. Cell 141, 290-303 (2010).
9. L. Bar-Peled, L. D. Schweitzer, R. Zoncu, D. M. Sabatini, Ragulator is a GEF for the rag GTPases that signal amino acid levels to mTORC1. Cell 150, 1196-1208 (2012).
10. R. L. Wolfson et al., KICSTOR recruits GATOR1 to the lysosome and is necessary for nutrients to regulate mTORC1. Nature 543, 438-442 (2017).
11. M. Peng, N. Yin, M. O. Li, SZT2 dictates GATOR control of mTORC1 signalling. Nature 543, 433-437 (2017).
12. S. Wang et al., Metabolism. Lysosomal amino acid transporter SLC38A9 signals arginine sufficiency to mTORC1. Science 347, 188-194 (2015).
13. M. Rebsamen et al., SLC38A9 is a component of the lysosomal amino acid sensing machinery that controls mTORC1. Nature 519, 477-481 (2015).
14. J. Jung, H. M. Genau, C. Behrends, Amino Acid-Dependent mTORC1 Regulation by the Lysosomal Membrane Protein SLC38A9. Mol Cell Biol 35, 2479-2494 (2015).
15. R. L. Wolfson et al., Sestrin2 is a leucine sensor for the mTORC1 pathway. Science 351, 43-48 (2016).
16. R. A. Saxton et al., Structural basis for leucine sensing by the Sestrin2-mTORC1 pathway. Science 351, 53-58 (2016).
17. R. A. Saxton, L. Chantranupong, K. E. Knockenhauer, T. U. Schwartz, D. M. Sabatini, Mechanism of arginine sensing by CASTOR1 upstream of mTORC1. Nature 536, 229-233 (2016).
18. L. Chantranupong et al., The CASTOR Proteins Are Arginine Sensors for the mTORC1 Pathway. Cell 165, 153-164 (2016).
19. E. L. Huttlin et al., Architecture of the human interactome defines protein communities and disease networks. Nature 545, 505-509 (2017).
20. L. Chantranupong et al., The Sestrins interact with GATOR2 to negatively regulate the amino-acid-sensing pathway upstream of mTORC1. Cell Rep 9, 1-8 (2014).
21. A. Parmigiani et al., Sestrins inhibit mTORC1 kinase activation through the GATOR complex. Cell Rep 9, 1281-1291 (2014).
22. A. Hildebrand, M. Remmert, A. Biegert, J. Soding, Fast and accurate automatic structure prediction with HHpred. Proteins 77 Suppl 9, 128-132 (2009).
23. P. Z. Kozbial, A. R. Mushegian, Natural history of S-adenosylmethionine-binding proteins. BMC Struct Biol 5, 19 (2005).
24. S. J. Mentch et al., Histone Methylation Dynamics and Gene Regulation Occur through the Sensing of One-Carbon Metabolism. Cell Metab 22, 861-873 (2015).
25. C. L. Quinlan et al., Targeting S-adenosylmethionine biosynthesis with a novel allosteric inhibitor of Mat2A. Nat Chem Biol 13, 785-792 (2017).
26. T. Wang et al., Gene Essentiality Profiling Reveals Gene Networks and Synthetic Lethal Interactions with Oncogenic Ras. Cell 168, 890-903 e815 (2017).
27. T. Wang et al., Identification and characterization of essential genes in the human genome. Science 350, 1096-1101 (2015).
28. M. Gossen, H. Bujard, Tight control of gene expression in mammalian cells by tetracycline-responsive promoters. Proc Natl Acad Sci USA 89, 5547-5551 (1992).
29. J. W. Locasale, Serine, glycine and one-carbon units: cancer metabolism in full circle. Nat Rev Cancer 13, 572-583 (2013).
30. J. A. Law, S. E. Jacobsen, Establishing, maintaining and modifying DNA methylation patterns in plants and animals. Nat Rev Genet 11, 204-220 (2010).
31. C. Ye, B. M. Sutter, Y. Wang, Z. Kuang, B. P. Tu, A Metabolic Function for Phospholipid and Histone Methylation. Mol Cell 66, 180-193 e188 (2017).
32. B. M. Sutter, X. Wu, S. Laxman, B. P. Tu, Methionine inhibits autophagy and promotes growth by inducing the SAM-responsive methylation of PP2A. Cell 154, 403-415 (2013).
33. N. Orentreich, J. R. Matias, A. DeFelice, J. A. Zimmerman, Low methionine ingestion by rats extends life span. J Nutr 123, 269-274 (1993).
34. R. A. Miller et al., Methionine-deficient diet extends mouse lifespan, slows immune and lens aging, alters glucose, T4, IGF-I and insulin levels, and increases hepatocyte MIF levels and stress resistance. Aging Cell 4, 119-125 (2005).
35. L. Sun, A. A. Sadighi Akha, R. A. Miller, J. M. Harper, Life-span extension in mice by preweaning food restriction and by methionine restriction in middle age. J Gerontol A Biol Sci Med Sci 64, 711-722 (2009).
36. H. M. Brown-Borg et al., Growth hormone signaling is necessary for lifespan extension by dietary methionine. Aging Cell 13, 1019-1027 (2014).
37. D. Wanders et al., Role of GCN2-Independent Signaling Through a Noncanonical PERK/NRF2 Pathway in the Physiological Responses to Dietary Methionine Restriction. Diabetes 65, 1499-1510 (2016).
38. O. Boussif et al., A versatile vector for gene and oligonucleotide transfer into cells in culture and in vivo: polyethylenimine. Proc Natl Acad Sci USA 92, 7297-7301 (1995).

39. S. Sharma, P. Watzinger, P. Kotter, K. D. Entian, Identification of a novel methyltransferase, Bmt2, responsible for the N-1-methyl-adenosine base modification of 25S rRNA in *Saccharomyces cerevisiae*. Nucleic Acids Res 41, 5428-5443 (2013).
40. D. H. Kim et al., mTOR interacts with raptor to form a nutrient-sensitive complex that signals to the cell growth machinery. Cell 110, 163-175 (2002).
41. K. Birsoy et al., An Essential Role of the Mitochondrial Electron Transport Chain in Cell Proliferation Is to Enable Aspartate Synthesis. Cell 162, 540-551 (2015).
42. W. W. Chen, E. Freinkman, T. Wang, K. Birsoy, D. M. Sabatini, Absolute Quantification of Matrix Metabolites Reveals the Dynamics of Mitochondrial Metabolism. Cell 166, 1324-1337 e1311 (2016).

What is claimed is:

1. A method of identifying a test compound as an inhibitor of mTORC1 activity comprising the steps of:
   a) providing a mixture comprising:
      (i) a polypeptide comprising SAMTOR;
      (ii) a GATOR1-KICSTOR complex; and
      (iii) a test compound,
   under conditions that prevent the polypeptide from associating with the GATOR1-KICSTOR complex; and
   b) determining whether the amount of the polypeptide associated with the GATOR1-KICSTOR complex is altered in the presence of the test compound as compared to either the absence of the test compound or the presence of a negative control, wherein if the amount of association is increased the test compound is identified as an inhibitor of mTORC1 activity.

2. The method of claim 1, wherein the conditions that prevent the polypeptide from associating with the GATOR1-KICSTOR complex comprises the presence of S-adenosylmethionine (SAM).

3. The method of claim 1, wherein:
   (i) the polypeptide is bound to a first tag;
   (ii) the GATOR1-KICSTOR complex is bound to a second tag; or
   (iii) each of the polypeptide and the GATOR1-KICSTOR complex is bound to its corresponding tag; and
   wherein the step of determining the amount of the polypeptide associated with the GATOR1-KICSTOR complex: (a) comprises detecting at least one of the first or second tag or a product of the first and second tag; and (b) distinguishes between the polypeptide associated with the GATOR1-KICSTOR complex and the polypeptide not associated with the GATOR1-KICSTOR complex.

4. The method of claim 3, wherein:
   the first tag is present and comprises a first epitope not naturally present in SAMTOR;
   the second tag is present and comprises a second epitope not naturally present in any GATOR1-KICSTOR complex;
   detecting the first tag comprises binding a first antibody specific for the first epitope; and
   detecting the second tag comprises binding a second antibody specific for the second epitope.

5. The method of claim 1, wherein:
   one of the polypeptide or GATOR1-KICSTOR complex is bound to a solid support; and
   detecting the association of the polypeptide with the GATOR1-KICSTOR complex comprises surface plasmon resonance.

6. A method of identifying a test compound as a modulator of mTORC1 by determining if the test compound can decrease or increase the affinity of SAMTOR for S-adenosylmethionine comprising the steps of:
   a. providing a mixture comprising:
      i. a SAMTOR polypeptide;
      ii. S-adenosylmethionine; and
      iii. a test compound,
   under conditions that allow S-adenosylmethionine to bind to the polypeptide; and
   b. determining whether the amount of S-adenosylmethionine bound to the polypeptide is altered in the presence of the test compound as compared to either the absence of the test compound or the presence of a negative control, wherein if the amount of binding is decreased in the presence of test compound, the test compound is identified as an inhibitor of mTORC1 activity; and if the amount of binding is increased in the presence of the test compound, the test compound is identified as an activator of mTORC1 activity.

7. The method of claim 6, wherein the S-adenosylmethionine is tagged with a detectable label.

8. The method of claim 7, wherein the S-adenosylmethionine is tagged with a radiolabel.

9. The method of claim 6, comprising the additional step of separating polypeptide-bound S-adenosylmethionine from unbound S-adenosylmethionine prior to determining the amount of S-adenosylmethionine bound to the polypeptide.

* * * * *